US008389745B2

(12) United States Patent
Lukhtanov et al.

(10) Patent No.: US 8,389,745 B2
(45) Date of Patent: *Mar. 5, 2013

(54) PHOSPHONATE FLUORESCENT DYES AND CONJUGATES

(75) Inventors: Eugeny Lukhtanov, Bothell, WA (US); Alexei Vorobiev, Redmond, WA (US)

(73) Assignee: Elitech Holding B.V., Spankeren (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/220,467

(22) Filed: Aug. 29, 2011

(65) Prior Publication Data

US 2012/0116079 A1 May 10, 2012

Related U.S. Application Data

(62) Division of application No. 12/683,305, filed on Jan. 6, 2010, now Pat. No. 8,008,522, which is a division of application No. 11/202,635, filed on Aug. 12, 2005, now Pat. No. 7,671,218.

(60) Provisional application No. 60/601,599, filed on Aug. 13, 2004.

(51) Int. Cl.
*C07D 311/78* (2006.01)

(52) U.S. Cl. ............ 549/224; 549/223; 435/6; 436/172; 536/26.6

(58) Field of Classification Search .................. None
See application file for complete search history.

(56) References Cited

U.S. PATENT DOCUMENTS

| | | | |
|---|---|---|---|
| 3,809,694 A | 5/1974 | Redmore | |
| 5,106,762 A | 4/1992 | Bredehorst et al. | |
| 5,227,487 A | 7/1993 | Haugland et al. | |
| 5,231,191 A | 7/1993 | Woo et al. | |
| 5,366,860 A | 11/1994 | Bergot et al. | |
| 5,637,509 A | 6/1997 | Hemmila et al. | |
| 5,750,409 A | 5/1998 | Herrmann et al. | |
| 5,756,771 A | 5/1998 | Mattingly | |
| 5,916,877 A | 6/1999 | Powers et al. | |
| 6,008,373 A | 12/1999 | Waggoner et al. | |
| 6,008,379 A | 12/1999 | Benson et al. | |
| 6,130,101 A | 10/2000 | Mao et al. | |
| 6,184,379 B1 | 2/2001 | Josel et al. | |
| 6,191,278 B1 | 2/2001 | Lee et al. | |
| 6,221,604 B1 | 4/2001 | Upadhya et al. | |
| 6,238,838 B1 | 5/2001 | Gaschler | |
| 6,248,884 B1 | 6/2001 | Lam et al. | |
| 6,348,596 B1 | 2/2002 | Lee et al. | |
| 6,372,907 B1 | 4/2002 | Lee et al. | |
| 6,432,642 B1 | 8/2002 | Livak et al. | |
| 6,448,407 B1 | 9/2002 | Lee et al. | |
| 6,465,644 B1 | 10/2002 | Yan et al. | |
| 6,583,168 B1 | 6/2003 | Menchen | |
| 6,649,769 B2 | 11/2003 | Lee et al. | |
| 6,673,550 B2 | 1/2004 | Matray et al. | |
| 6,673,943 B2 | 1/2004 | Waggoner et al. | |
| 6,706,879 B2 | 3/2004 | Anderson et al. | |
| 6,716,994 B1 | 4/2004 | Menchen et al. | |
| 6,781,001 B2 | 8/2004 | Lam et al. | |
| 6,811,979 B2 | 11/2004 | Taing et al. | |
| 6,897,036 B2 | 5/2005 | Akhavan-Tafti et al. | |
| 6,972,339 B2 | 12/2005 | Lukhtanov et al. | |
| 7,018,840 B2 | 3/2006 | Lippard et al. | |
| 7,038,063 B2 | 5/2006 | Lee et al. | |
| 7,671,218 B2 * | 3/2010 | Lukhtanov et al. | 549/223 |
| 7,767,834 B2 * | 8/2010 | Lukhtanov et al. | 549/223 |
| 2002/0146726 A1 | 10/2002 | Maltray et al. | |
| 2003/0008405 A1 | 1/2003 | Lippard et al. | |
| 2003/0055243 A1 | 3/2003 | Lee et al. | |
| 2003/0088109 A1 | 5/2003 | Anderson et al. | |
| 2003/0186348 A1 | 10/2003 | Thomas et al. | |
| 2003/0196214 A1 | 10/2003 | Sharma et al. | |
| 2003/0220502 A1 | 11/2003 | Waggoner et al. | |
| 2003/0232405 A1 | 12/2003 | Akhavan-Tafti et al. | |
| 2004/0029290 A1 | 2/2004 | Scott et al. | |
| 2004/0146959 A1 | 7/2004 | Graham et al. | |
| 2004/0147728 A1 | 7/2004 | Meltola et al. | |
| 2004/0191792 A1 | 9/2004 | Smith et al. | |
| 2004/0229235 A1 | 11/2004 | Lee et al. | |
| 2004/0260093 A1 | 12/2004 | Czerney et al. | |
| 2005/0026235 A1 | 2/2005 | Graham et al. | |
| 2005/0214833 A1 | 9/2005 | Carter et al. | |
| 2005/0251923 A1 | 11/2005 | Greaves et al. | |

FOREIGN PATENT DOCUMENTS

| | | |
|---|---|---|
| JP | 2003-34695 | 2/2003 |
| WO | 9951702 A1 | 10/1999 |
| WO | 2003023357 | 3/2003 |
| WO | 2004037907 A2 | 5/2004 |
| WO | 2004101579 | 11/2004 |
| WO | 2005/044923 | 5/2005 |
| WO | 2005118839 | 12/2005 |

OTHER PUBLICATIONS

CAS Online Registry No. 70987-08-1 (1 pg.).
CAS Online Registry No. 78752-19-9 (1 pg.).
European Patent Office, Office Action, European Application No. 05786453.0, Nov. 15, 2011.
Japanese Patent Office, Written Argument in Japanese, Japanese Application No. 2007-525859, Nov. 22, 2011.
Japanese Patent Office, Written Amendment in English, Japanese Application No. 2007-525859, Nov. 22, 2011.
European Patent Office, Extended Search Report, European Application No. 07751231.7, Dec. 29, 2011.
European Patent Office, Response to Search Opinion, Marked up claims, Clean claims as amended, European Application No. 07751231.7, Jul. 20, 2012.
Japanese Patent Office, Decision of Rejection and Pending Claims, Japanese Application No. 2007-525859, Aug. 1, 2012.
Japanese Patent Office, Notice of Reasons for Rejection in Japanese, Japanese Application No. 2008-556399, Oct. 22, 2012.

(Continued)

*Primary Examiner* — Sudhakar Katakam
(74) *Attorney, Agent, or Firm* — Jackson Walker L.L.P.

(57) ABSTRACT

Reagents are provided for the introduction of phosphonate groups into fluorescent dyes. Methods are also provided for preparing dye conjugates.

12 Claims, 4 Drawing Sheets

OTHER PUBLICATIONS

Japanese Patent Office, Notice of Reasons for Rejection in English, Japanese Application No. 2008-556399, Oct. 22, 2012.

International Search Report for PCT Application No. PCT/US2005/028892 mailed Jun. 5, 2008 (2 pgs.).

European Search Report, mailed Mar. 30, 2010 (12 pgs.).

Johnson et al., "Fluorescent Membrane Probes Incorporating Dipyrrometheneboron Difluoride Fluorophores," Analytical Biochemistry, vol. 198, 1991, pp. 228-237.

Mattjus et al., "A Fluorescence Resonance Energy Transfer Approach for Monitoring Protein-Mediated Glycolipid Transfer Between Vesicle Membranes," Analytical Biochemistry, vol. 268, 1999, pp. 297-304.

Monti et al., "Uptake and Metabolism of a Fluorescent Sulfatide Analogue in Cultured Skin Fibroblasts," Biochemica et Biophysica Acta, vol. 1124, 1992, pp. 80-87.

Xu et al., "Multiphoton Excitation Cross-Sections of Molecular Fluorophores," Bioimaging, vol. 4, 1996, pp. 198-207.

Yang et al., "Two-Photon Absorption Properties of 2,6-Bis-(styryl)anthracene Derivatives: Effects of Donor-Acceptor Substituents and the $\pi$ Center," Chem. Eur. J. vol. 11, 2005, pp. 4191-4198.

Written Opinion of the International Searching Authority for PCT/US2005/028892 mailed Nov. 7, 2008.

International Preliminary Report on Patentability for PCT/US2005/028892 mailed Nov. 24, 2008.

\* cited by examiner

Benzo[a]phenoxazines (X)

and

Benzo[b]phenoxazines (XI)

Benzo[c]phenoxazines (XII)

a)

b)

PHOSPHONATE FLUORESCENT DYES AND CONJUGATES

CROSS-REFERENCES TO RELATED APPLICATIONS

This application is a divisional application and claims the benefit of U.S. patent application Ser. No. 12/683,305, entitled Phosphonate Fluorescent Dyes and Conjugates, filed Jan. 6, 2010, which is expressly incorporated herein by reference in its entirety, and which claims the benefit of U.S. patent application Ser. No. 11/202,635, entitled "Phosphonate Fluorescent Dyes and Conjugates," filed Aug. 12, 2005, which is expressly incorporated herein by reference in its entirety, and which claims the benefit of U.S. Provisional application Ser. No. 60/601,599 filed Aug. 13, 2004, the content of which is incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention provides a number of modified dyes, such as xanthene dyes, including rhodamines, rhodols and fluoresceins that are substituted with one or two phosphonate groups that are either zwitterionic or a protected form thereof. The dyes of the invention, including chemically reactive dyes and dye-conjugates are useful as fluorescent probes, particularly in biological samples.

Fluorescent dyes are known to be particularly useful in biological applications where a highly sensitive detection reagent is required. Fluorescent dyes are used to label both visible color and fluorescence to other materials. The dyes of this invention are phosphonate derivatives of xanthene-based dyes that are typically fluorescein, rhodamine or rhodol derivatives

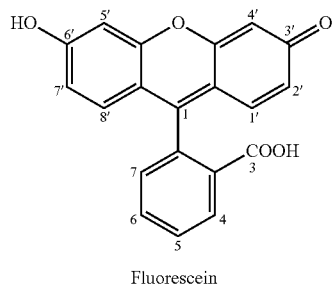

Fluorescein

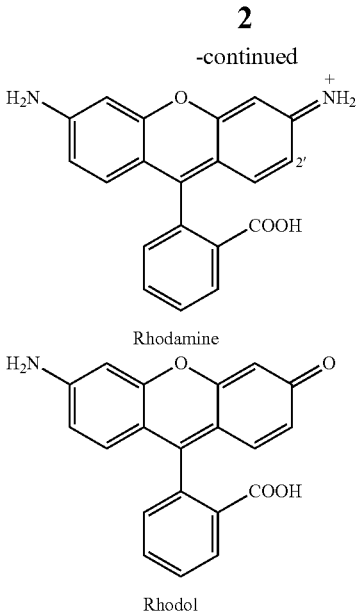

Rhodamine

Rhodol

"Fluorescein" dyes include derivatives of 3H-xanthen-6-ol-3-one that are typically substituted at the 9-position by a 2-carboxyphenyl group. "Rhodamine" dyes include derivatives of 6-amino-3H-xanthen-3-imine that are typically substituted at the 9-position by a 2-carboxyphenyl group. "Rhode" dyes include derivatives of 6-amino-3H-xanthen-3-one that are typically substituted at the 9-position by a 2-carboxyphenyl group. Fluoresceins, rhodamines and rhodols are typically substituted by a derivative capable of forming a 5- or 6-membered lactone or lactam ring. For example in the case of fluorescein the spirolactone form of the dye has the following structure:

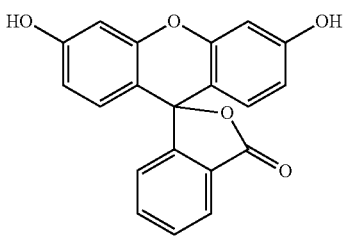 [SMILES: O=C1OC2(c3ccc(O)cc3Oc3cc(O)ccc32)c2ccccc21]

Many commercial fluorescent dyes have a polycyclic aromatic nature and are hydrophobic. Those molecules are also prone to minimize exposure to any hydrophilic environment through interactions with nearby hydrophobic surfaces and residues. These interactions include dye-dye interaction and dye-biomolecule (e.g. proteins, lipids, oligonucleoties) interactions. Hydrophobic interactions can cause substantial quenching effect for fluorescent dyes (see for example Randolph, J. B.; Waggoner, A. S. *Nucleic Acids Res.* 1997, 25(14), 2923-2929 and references cited therein). One method to overcome this problem is to improve the hydrophilic character of the dye by, for example, introducing a sultanate substituent into the dye molecule (sulfonated carbocyanine dyes are disclosed in U.S. Pat. No. 5,268,486 and sulfonated xanthene dyes are disclosed in U.S. Pat. No. 6,130,101).

The present invention describes dyes, including fluorescein, rhodol and rhodamine dyes that are substituted by at least one phosphonate moiety. The phosphonate-substituted dyes of the invention possess considerable advantages over their unsubstituted hydrophobic analogs. Being ionized, the phosphonate group brings additional hydrophilicity to the dye molecules, increasing their solubility in aqueous solutions. Importantly, the quantum yield of the new dyes is not decreased by introduction of a phosphonate moiety. In contrast to the sulfonated dyes, the dyes of the invention are compatible with the synthetic conditions used on commercial oligonucleotide synthesizers.

BRIEF SUMMARY OF THE INVENTION

In one aspect, the present invention provides a fluorescent dye reagent having the formula:

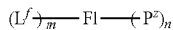

wherein Fl is a fluorescent dye component; $L^f$ is a linking group having an attached member selected from the group consisting of a protected or unprotected functional group, a reactive group, a polyfunctional linking moiety, a phosphoramidite moiety and a solid support; the subscript m is an integer of from 0 to 1; $P^z$ is a zwitterionic phosphonate group having the formula (a) or a protected phosphonate group having formula (b) or (c):

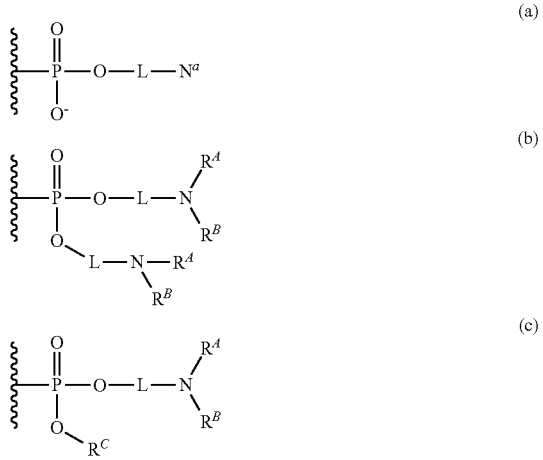

wherein the wavy line indicates the direct attachment to a $sp^2$ carbon of said fluorescent dye component; L is a linking group; $N^a$ is an ammonium ion group; each of $R^A$ and $R^B$ is independently selected from the group consisting of H, $(C_1-C_8)$alkyl and a labile protecting group, such as $C(O)CF_3$, FMOC, tButyl, tBOC, phthalimide and monomethoxytrityl; the subscript n is an integer of from 1 to 4, preferably 1 to 2; $R^C$ is H, $(C_1-C_8)$alkyl, aryl, aryl$(C_1-C_4)$alkyl, a labile protecting group or an alkylene linking group having a distal hydroxy or protected hydroxy group; and salts thereof.

In another aspect, the present invention provides fluorescent dye reagent having the formula:

$$Fl-P^1$$

wherein Fl is a fluorescent dye component; and $P^1$ is functionalized phosphonate group having the formula:

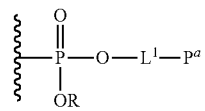

wherein the wavy line indicates the direct attachment to a $sp^2$ carbon of said fluorescent dye component; $L^1$ is a linking group; R is a member selected from the group consisting of H, $C_1-C_8$ alkyl, aryl, aryl $C_1-C_4$ alkyl, $-L^A-N^a$, and $-L^a-NR^AR^B$; wherein $L^a$ is an alkylene linking group, $N^a$ is an ammonium ion group, and each of $R^A$ and $R^B$ is independently selected from the group consisting of $(C_1-C_8)$alkyl and a labile protecting group; and $P^a$ is a functional group component selected from the group consisting of a phosphoramidite moiety, a mono-, di- or tri-functional linking group having at least one terminal functional group or protected functional group, a solid support and a reactive group; and salts thereof.

In other aspects, the present invention provides methods of preparing phosphonate fluorescent dye reagents as well as methods of using probes (e.g., oligonucleotide probes) having attached phosphonate fluorescent dyes as provided herein.

DETAILED DESCRIPTION OF THE INVENTION

Abbreviations and Definitions

Figure 1:
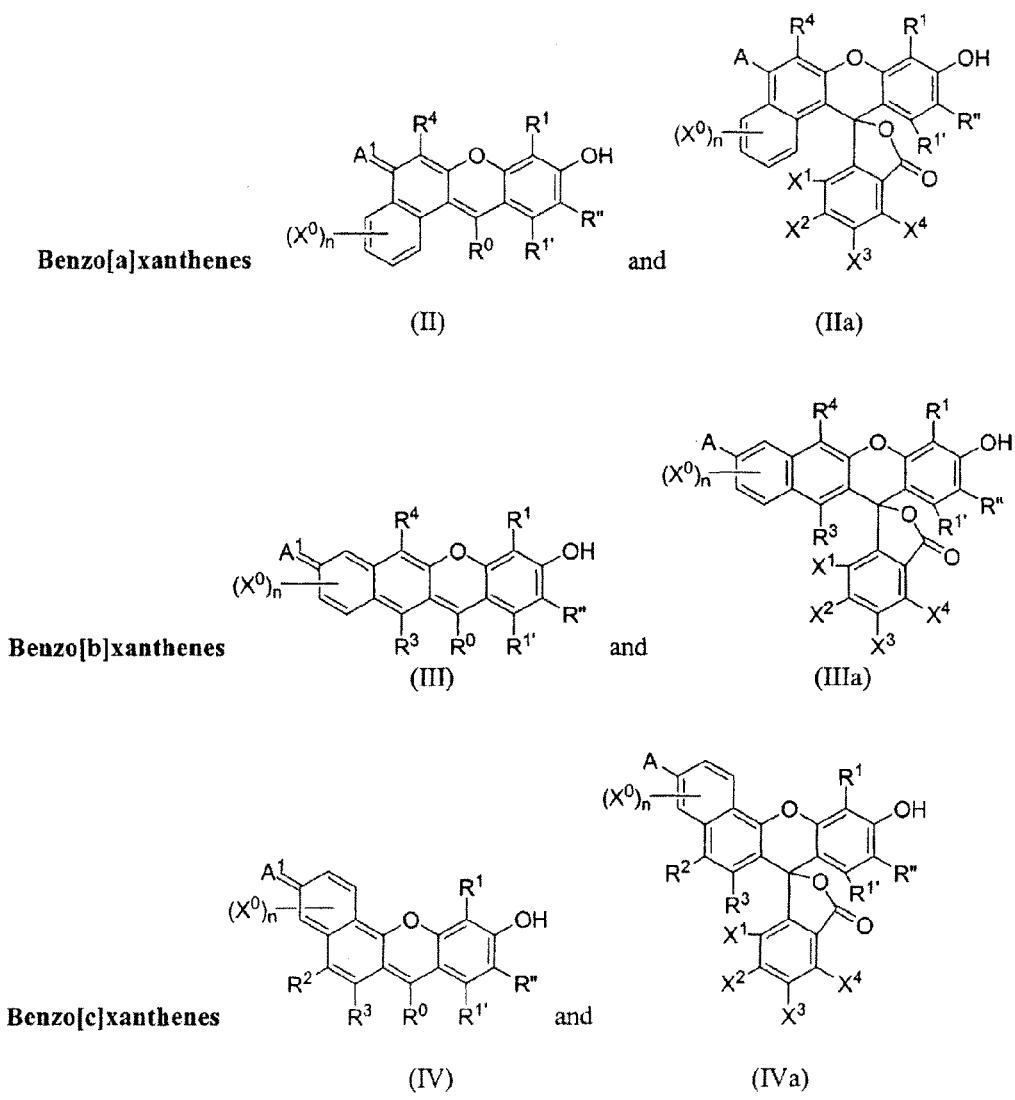
FIG. 1 illustrates the structures of selected classes of benzoxanthene dyes of the present invention.

Unless otherwise stated, the following terms used in the specification and claims have the meanings given below:

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, arylalkoxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, $(C_2-C_6)$ alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, $(C_2-C_6)$ alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "aryl" means a monovalent monocyclic or bicyclic aromatic hydrocarbon radical of 6 to 10 ring atoms which is =substituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl cut, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one or more heteroatoms or heteroatom functional groups have replaced a ring carbon, while retaining aromatic properties, e.g., pyridyl, quinolinyl, quinazolinyl, thienyl, and the like. For brevity, the term aryl, when used in combination with other radicals (e.g., aryloxy, arylalkyl) is meant to include both aryl groups and heteroaryl ups as described above.

The term "arylalkyl" refers to a radical —R$^a$R$^b$ where R$^a$ is an alkylene group (having the indicated number of carbon atoms, or if unspecified having six or fewer main chain carbon atoms) and R$^b$ is an aryl group as defined herein. Examples of arylalkyl groups include benzyl, phenylethyl, 3-(3-chlorophenyl)-2-methylpentyl, and the like.

Similarly the term "arylalkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group (having the indicated number of carbon atoms) and R$^b$ is an aryl group as defined herein, e.g., 2-hydroxy-2-phenyethyl, 2-hydroxy-1-hydroxymethyl-2-phenyl-ethyl, and the like.

The term "aryloxy", refers a radical —OR where R is an aryl group, phenoxy, naphthyloxy and the like.

The prefix "halo" and the term "halogen" when used to describe a substituent, refer to —F, —Cl, —Br and —I.

The term "heteroalkyl" refers to an alkyl radical as defined herein with one, two or three substituents independently selected from cyano, OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, aryl, arylalkyl, alkoxycarbonyl, aryloxycarbonyl, carboxamido, or mono- or di-alkylcarbamoyl. R$^b$ is hydrogen, alkyl, aryl or arylalkyl. R$^c$ is hydrogen, alkyl, aryl, arylalkyl, alkoxycarbonyl, aryloxycarbonyl, carboxamido, mono- or di-alkylcarbamoyl or alkylsulfonyl. R$^d$ is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^a$, R$^b$, R$^c$, and R$^d$ can be further substituted by NH$_2$, fluorine, alkylamino, di-alkylamino, OH or alkoxy. Additionally, the prefix indicating the number of carbon atoms (e.g., $C_1-C_{10}$) refers to the total number of carbon atoms in the portion of the heteroalkyl group exclusive of the cyano, —OR$^a$, —NR$^b$R$^c$, or —S(O)$_n$R$^d$ portions.

The term "heterocyclic" refers to a saturated or unsaturated non-aromatic cyclic radical of 3 to 8 ring atoms in which one or two ring atoms are heteroatoms selected from O, NR (where R is independently hydrogen or alkyl) or S(O)$_n$ (where n is an integer from 0 to 2), the remaining ring atoms being C, where one or two C atoms may optionally be replaced by a carbonyl group. The heterocyclic ring may be optionally substituted independently with one, two, or three substituents selected from alkyl, halo, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, phenyl or phenylalkyl). More specifically the term heterocyclic includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3-C_{10}$) refers to the total number of carbon atoms in the portion of the heterocyclic group exclusive of the number of heteroatoms.

The terms "heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, R$^b$, R$^c$ and R$^d$ are as defined herein for a heteroalkyl radical. Examples include, 2-hydroxyethan-1, 2-diyl, 2-hydroxypropan-1,3-diyl and the like.

Each of the above terms (e.g., "alkyl," "heteroalkyl," and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, NR'C(NH$_2$)=NH, —NH—C(NH$_2$)=NR', —S(O)R', —S(O)$_2$R', —S(O)$_2$NR'R", —CN and —NO$_2$ in a number ranging from zero to four, preferably, zero, one, two or three substituents. R', R" and R'" each independently refer to hydrogen, unsubstituted ($C_1-C_8$)alkyl and heteroalkyl, unsubstituted aryl, aryl substituted with 1-3 halogens, unsubstituted alkyl, alkoxy or thioalkoxy groups, or aryl-($C_1-C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0-3 substituents, more preferably 0, 1, or 2 substituents, unless otherwise specified.

Similarly, substituents for the aryl groups are varied and are selected from: -halogen, —OR', —OC(O)R', —NR'R'', —SR', —R', —CN, —NO$_2$, —CO$_2$R', —CONR'R'', —C(O)R', OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of ADVANCED ORGANIC CHEMISTRY, 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W, Greene and P. G. Wuts, PROTECTIVE GROUPS IN ORGANIC CHEMISTRY, (Wiley, 2nd ed. 1991), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000). Representative hydroxy protecting groups include those where the hydroxy group is either acylated or alkylated such as benzyl and trityl ethers as well as alkyl ethers, tetrahydropyranyl ethers, trialkylsilyl ethers and allyl ethers, Additionally, hydroxy groups can be protected by photoremovable groups such as α-methyl-6-nitropiperonyloxycarbonyl (McGall, G. H. and Fidanza, J. A., Photolithographic synthesis of high-density oligonucleotide arrays, in DNA ARRAYS METHODS AND PROTOCOLS, Edited by Rampal J. B., METHODS IN MOLECULAR BIOLOGY, 170:71-101 (2001), Humana Press, Inc., NY; Boyle, Ann L. (Editor), Current Protocols in Nucleic Acid Chemistry, John Wiley and Sons, New York, Volume 1, 2000).

The term "labile protecting group" refers to those protecting groups that are removeable under mild conditions that do not significantly impact the remainder of the molecule.

As used herein, the term "reactive group" refers to an electrophilic group or a nucleophilic group that can be used to form a covalent linkage with another component. Examples of nucleophilic groups include —NH$_2$, —NHNH$_2$, —ONH$_2$, —NHC═(O)NHNH$_2$, —OH, —COOH, or —SH. The electrophilic groups can be activated esters, acrylamides, acyl azides, acyl halides, aldehyde or ketones, alkyl halides, alkyl sulfonates, anhydrides, aryl halides, aziridines, boranates, carboxylic acids, carbodiimides, diazoalkanes, epoxides, haloacetamides, halotriazines, imidoesters, isocyanates, isothiocyanates, maleimides, phosphoramidites, silyl halides, sulfonate ester and sulfonyl halides. Additionally, a spacer can include hetero atoms in linear or acyclic portions, cyclic portions, aromatic rings or combinations thereof. Within the above, an "activated ester group" refers to a carboxylic acid ester which is more reactive than an alkyl ester (e.g., methyl ester) in reactions in which the carbonyl moiety is an electrophilic center toward, for example, amide formation. Examples of activated esters include pentafluomphenyl (PFP) esters, N-hydroxysuccinimide esters, and the like.

A "polyfunctional linking moiety" is a linking group having two or more functional groups that can be used to attach or conjugate two or more components that can be the same or different. Polyfunctional linking moieties include, for example, trivalent linking groups and tetravalenet linking groups (see, for example, U.S. Pat. Nos. 5,512,677; 5,419,966; 5,585,481; 5,942,610 and 5,736,626).

A "phosphoramidite" is a term of art used to refer to a trivalent phosphorus group typically used in oligonucleotide synthesis. Detailed descriptions of the chemistry used to form oligonucleotides by the phosphoramidite method are provided in Caruthers et al., U.S. Pat. Nos. 4,458,066 and 4,415,732; Caruthers et al., Genetic Engineering, 4:1-17 (1982); Users Manual Model 392 and 394 Polynucleotide Synthesizers, pages 6-1 through 6-22, Applied Biosystems, Part No 901237 (1991), each of which are incorporated by reference in their entirety. Labeled oligonucleotides can be synthesized enzymatically. e.g., using a DNA polymerase or ligase, e.g., Stryer, Biochemistry, Chapter 24, W.H. Freeman and Company (1981), or by chemical synthesis, e.g., by a phosphoramidite method, a phosphite-triester method, and the like, e.g., Gait, OLIGONUCLEOTIDE SYNTHESIS, IRL Press (1990). Labels can be introduced during enzymatic synthesis utilizing labeled nucleoside triphosphate monomers, or introduced during chemical synthesis using labeled non-nucleotide or nucleotide phosphoramidites, or may be introduced subsequent to synthesis. A typical phosphoramidite reagent used in oligonucleotide synthesis is represented by the structure below:

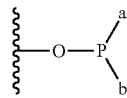

wherein the wavy line indicates the attachment to the remainder of the reagent and the substituents "a" and "b" are each independently isopropyl amino, diisopropylamino, 2-cyanoethyloxy, methoxy or morpholino and "a" and "b" are not the same.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

The term "biological agent" refers to essentially any nucleoside, oligonucleotide, peptide, protein, aminocarbohydrate or ligand, as well as analogs thereof (e.g., oligonucleotides having modified or non-natural bases).

The term "conjugate" refers to a molecule formed by the covalent attachment of two or more components such as oligonucleotides, fluorophores, quenchers, minor groove hinders, and the like, "Oligonucleotide" and "polynucleotide" are used interchangeably and refers to a polymer of nucleotides, either natural or synthetic including, but not limited to those nucleotides having modified bases, sugar analogs, and the like. As noted groove oligonucleotide conjugate will refer to an oligonucleotide as defined, having at least one covalently attached fluorophore, quencher, minor groove binder (MGB) or other useful fragments, as well as combinations of the recited components.

The term "solid support" refers to essentially any solid or semisolid matrix that is useful for, and compatible with, automated oligonucleotide techniques and includes, glass, polystyrene, nylon, plastic, combinations and the like, Examples of useful solid supports have been described in, for example, U.S. Pat. Nos. 5,262,530, 5,419,966, 5,512,667 and 5,589,586.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sans (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

The present invention resides in the discovery that a wide variety of fluorescent dyes (or fluorophores) can be prepared having a zwitterionic phosphonate group (or a protected form thereof), providing reagents that are shelf-stable and that can be used to label essentially any biological agent (e.g., oligonucleotides, peptides, proteins, probes, and the like). Accordingly, the invention provides new "phosphonate dyes" as well as methods of labeling biological agents using these "phosphonate dyes". The invention further provides reagents such as phosphoramidite-derivatized dyes that can be prepared from the phosphonate dyes described herein. Additionally, support-bound dyes, similarly prepared from the phosphonate dyes are also described.

The "phosphonate dyes" (e.g., dyes having a zwitterionic phosphonate group or a protected form thereof), as well as reagents incorporating those dyes (e.g., support-bound dyes and phosphoramidites) have been found to be compatible with, for example, coumarin dyes, benzocoumarin dyes, fluorescein dyes, rhodol dyes, phenoxazine dyes, benzophenoxazine dyes, xanthene dyes, benzoxanthene dyes, and cyanine dyes.

Examples of these and other suitable dye classes can be found in Haugland, et al., HANDBOOK OF FLUORESCENT PROBES AND RESEARCH CHEMICALS, SIXTH ED., Molecular Probes, Eugene, Ore. 1996; U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP 1408366; Smith, et al., J. Chem. Soc. Perkin Trans. 2, 1993, 1195-1204; Whitaker, et al., *Anal. Biochem.* 207:267-279 (1992); Krasoviskii and Bolotin, ORGANIC LUMINESCENT MATERIALS, VCH Publishers, NY., 1988; Zolliger, COLOR CHEMISTRY, 2$^{nd}$ Edition, VCH Publishers, NY., 1991; Hirschberg, et al., *Biochemistry* 37:10381-10385 (1998); Fieser and Fieser, REAGENTS FOR ORGANIC SYNTHESIS, Volumes 1 to 17, Wiley, US, 1995. Geiger, et al., *Nature* 359:859-861 (1992). Still other dyes are provided via online sites such as http://www.zeiss.com.

EMBODIMENTS OF THE INVENTION

In one aspect, the present invention provides fluorescent dye reagents having the general formula (A):

(A)

wherein Fl is a fluorescent dye component; $L^f$ is a linking group having an attached member selected from the group consisting of a protected or unprotected functional group, a reactive group, a polyfunctional linking moiety, a phosphoramidite moiety and a solid support; the subscript in is an integer of from 0 to 1; $P^z$ is a zwitterionic phosphonate group having the formula (a) or a protected phosphonate group having formula (b) or (c):

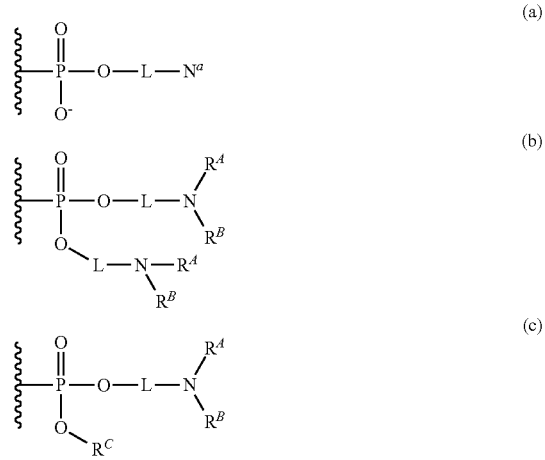

wherein the wavy line indicates the direct attachment to a sp$^2$ carbon of said fluorescent dye component; L is a linking group; $N^a$ is an ammonium ion group; each of $R^A$ and $R^B$ is independently selected from the group consisting of H, (C$_1$-C$_8$)alkyl and a labile protecting group, such as C(O)CF$_3$, FMOC, tButyl, tBOC, phthalimide and monomethoxytrityl; the subscript n is an integer of from 1 to 4, preferably 1 to 2; $R^C$ is H, (C$_1$-C$_8$)alkyl, aryl, aryl(C$_1$-C$_4$)alkyl, a labile protecting group or an alkylene linking group having a distal hydroxy or protected hydroxy group; and salts thereof.

In the context of the present invention, essentially any fluorescent dye can be modified to include either of $L^f$ and $P^z$.

Typically, $P^z$ is attached to an sp$^2$-hybridized carbon atom on an aromatic ring of the fluorescent dye using synthetic methods as described below. Similarly, $L^f$ can be attached to an existing functional group on the dye or can be a vestige of, for example, a lactone dye (see co-pending application Ser. No. 10/026,374).

Suitable dyes can be selected from, for example, coumarins, benzocoumarins, xanthenes, benzo[a]xanthenes, benzo[b]xanthenes, benzo[c]xanthenes, cyanines, acridines, dipyrrometheneboron di fluorides, phenoxazines, benzo[a]phenoxazines, benzo[b]phenoxazines and benzo[c]phenoxazines. Still other types of useful dyes are ruthenium bipyridyl dyes, energy transfer dyes, thiazole orange dyes, N-aryl-1,8-naphthalimide dyes, and other dyes shown in the present application.

In one group of embodiments, the fluorescent dye reagents are those in which the subscript m is 1 and the subscript n is 1. Within this group of embodiments, $P^z$ can have formula (a) or (b). Preferably, as a reagent that will be subject to additional manipulations or synthetic methods, the phosphonate ester groups are protected (e.g., as in formula (b)). When the reagent is incorporated into a probe (see embodiments discussed below) and used in assays, the phosphonate is in a zwitterionic form (e.g., as in formula (a)).

In another group of embodiments, the fluorescent dye reagents are those in which the subscript in is 0 and the subscript n is 1. Within this group of embodiments, $P^z$ can have formula (a) or (b). Preferably, as a reagent that will be subject to additional manipulations or synthetic methods, the phosphonate ester groups are protected as in formula (b) and (c).

In still another group of embodiments, the fluorescent dye reagents are those in which the subscript m is 0 and the subscript n is 2. Within this group of embodiments, each of the $P^z$ groups can be the same or different and can have formula (a), (b) or (c). As above, when the reagent is to be subjected to additional manipulations or synthetic methods, the phosphonate ester groups are preferably protected (e.g., as in formula (b) and (c)).

In a number of embodiments, L is C$_2$-C$_8$ alkylene. In other embodiments of the general formula above, $N^a$ is an ammonium ion group having the formula —N$^+$(R$^D$)$_3$ wherein each R$^D$ is independently selected from H, C$_1$-C$_8$ alkyl, aryl and aryl C$_1$-C$_4$ alkyl. Still more preferably, each R$^D$ is independently selected from H or C$_1$-C$_8$ alkyl.

Returning to the general formula above, $L^f$ can be a variety of linking groups known to those skilled in the art. Many linking groups are available from commercial sources and can be utilized in the reagents above by coupling one end of the linker to the fluorescent dye and the other end of the linker to a protecting group. In one group of embodiments, $L^f$ is a (C$_2$-C$_{20}$)alkylene group, terminating in a functional group such as hydroxy, protected hydroxy, amino, protected amino, carboxy, carboxylate ester, carboxamide, urea, and the like. In other embodiments, $L^f$ is an alkylene group having an attached phosphoramidite moiety, preferably 2-cyanoethyl-N,N-diisopropylphosphoramidite. Similarly, the linking group L can be selected from a variety of linking groups having from 2 to 50 main chain atoms (e.g., alkylene linking groups, heteroalkylene linking groups, polyether linking groups and the like).

In sections below, a number of dyes and dye groups are discussed specifically and represent embodiments of particular interest. One of skill in the art, however, will appreciate that the invention is not limited to those embodiments, Xanthene Dyes In one group of embodiments, FL is selected from the family of xanthene dyes, including benzoxanthenes, and more specifically, fluorescein dyes, rhodamine dyes and rhodol dyes.

In a particular group of embodiments, the fluorescent dye reagent has formula

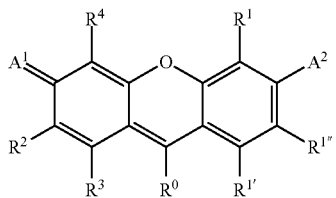

(I)

wherein $A^1$ represents O, N—Z or $N^+(Z)_2$ in which each Z is H or $(C_1-C_8)$allyl, or is optionally combined with $R^2$ or $R^4$ to form a 5- or 6-membered ring or is combined with each of $R^2$ and $R^4$ to form two fused 6-membered rings;

$A^2$ represents OR or $N(Z)_2$ in which each Z is H or $(C_1-C_8)$ alkyl, or is optionally combined with $R^1$ or $R^{1'''}$ to form a 5- or 6-membered ring or is combined, with each of $R^1$ and $R^{1'''}$ to form two fused 6-membered rings; and R is selected from H, $(C_1-C_8)$alkyl, aryl, aryl$(C_1-C_4)$allyl and $L^f$.

$R^{1'}$, $R^{1'''}$, $R^2$, $R^3$ and $R^4$ are each independently selected from H, halogen, cyano, $CF_3$, $(C_1-C_8)$alkyl, $(C_1-C_8)$alkylthio, $(C_1-C_8)$alkoxy, aryl, heteroaryl, $L^f$ and $P^z$; or optionally two adjacent members of $R^{1'}$, $R^{1'''}$, $R^2$ and $R^3$ are combined to form a five or six membered fused ring that is aromatic, non-aromatic or heteroaromatic and with is optionally substituted with $P^z$; wherein the alkyl portions of any of $R^{1'}$, $R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^{1'''}$ and $R^1$ through $R^4$ are optionally substituted with from one to four substituents selected from the group consisting of halogen, cyano, carboxy, sulfo, hydroxy, amino, mono- or di$(C_1-C_6)$alkylamino, $(C_1-C_6)$ alkyl, $(C_1-C_6)$alkylthio, $(C_1-C_6)$alkoxy, $L^f$ and $P^z$.

$R^0$ is halogen, cyano, $CF_3$, $(C_1-C_8)$alkyl, $(C_2-C_8)$alkenyl, $(C_2-C_8)$alkynyl, substituted or unsubstituted heteroaryl or aryl having the formula:

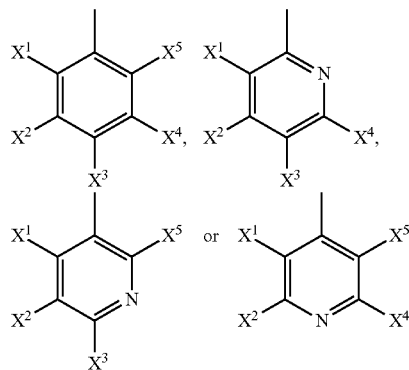

wherein $X^1$, $X^2$, $X^3$, $X^4$ and $X^5$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$, $PO_3H_2$, $CO_2H$, $L^f$ and $P^z$ and optionally, any two adjacent $X^1$ through $X^5$ are combined to form an aromatic or heteroaromatic ring. As above, any aryl or heteroaryl portions of $R^0$ are optionally substituted with from one to four substituents selected from the group consisting of halogen, cyano, carboxy, sulfo, hydroxy, amino, mono- or di$(C_1-C_6)$alkylamino, $(C_1-C_6)$ alkyl, $(C_1-C_6)$alkylthio, $(C_1-C_6)$alkoxy, $L^f$ and $P^z$. Within the above formula there will be from 0 to 1 $L^f$ groups and from 1 to 4 $P^z$ groups, preferably 1 to 2 $P^z$ groups.

In related embodiments, the fluorescent dye reagents utilize a fluorescent dye which is a protected fluorescent dye. Examples of such protected fluorescent dyes are well known to those of skill in the art, and will be apparent from the description of particular embodiments below.

In some embodiments, the fluorescent dye is a protected xanthene dye having formula (Ia) or (Ib):

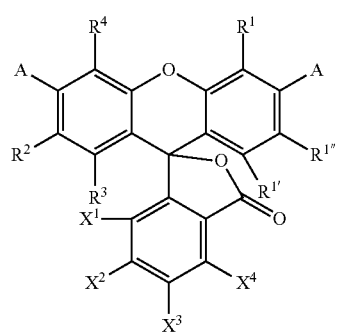

(Ia)

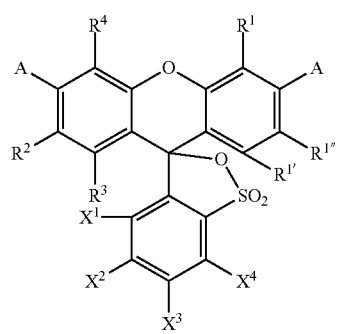

(Ib)

wherein each A is hydroxy, amino, protected hydroxy, or protected amino; $R^{1'}$, $R^{1'''}$, $R^1$, $R^2$, $R^3$ and $R^4$ are each independently selected from H, halogen, cyano, aryl, heteroaryl, $CF_3$, $(C_1-C_8)$alkyl, $(C_1-C_8)$alkylthio, $(C_1-C_8)$alkoxy, $L^f$ and $P^z$, or optionally two adjacent members of $R^{1'}$, $R^{1'''}$, $R^2$ and $R^3$ are combined to form a five or six membered fused ring that is aromatic, non-aromatic or heteroaromatic and which is optionally substituted with $P^z$, wherein the alkyl portions of any of $R^{1'}$, $R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms. The symbols $X^1$, $X^2$, $X^3$ and $X^4$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkynyl, aryl, heteroaryl, $SO_3H$, $PO_3H_2$, $CO_2H$, $L^f$ and $P^z$ and optionally, any two adjacent $X^1$ through $X^4$ are combined to form an aromatic or heteroaromatic ring that is optionally further substituted with from one to four substituents selected from halogen, cyano, carboxy, sulfo, hydroxy, amino, mono- or di$(C_1-C_6)$ alkylamino, $(C_1-C_6)$alkyl, $(C_1-C_6)$alkylthio and $(C_1-C_6)$alkoxy. Within the above formulae (Ia and Ib), there will be from 0 to 1 $L^f$ groups and from 1 to 2 $P^z$ groups. Preferred groups for A are —O—C(O)-tButyl and —O—C(O)-isopropyl.

In still other embodiments, the present invention provides compounds wherein FL is a benzoxanthene dye such as, for example, a benzo[a]xanthene, a benzo[b]xanthene or a benzo[c]xanthene (see formulae II, IIa, III, IIIa, IV and IVa in FIG. 1 wherein the substituents have the meanings provided above, and in addition subscript n in each of the formulae is an integer of from 0 to 3 and each $X^o$ is selected from the group consisting of halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$, $PO_3H_2$, $CO_2H$, $L^f$ and $P^z$ and any aryl or heteroaryl portions of $X^o$ are optionally substituted with from one to four substituents selected from the group consisting of halogen, cyano, carboxy, sulfa, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$).

Coumarin Dyes

In yet another group of embodiments, the fluorescent dye reagent has the formula:

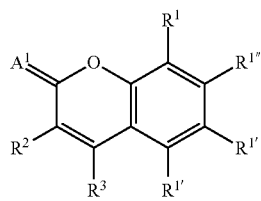

(V)

wherein $R^1$, $R^{1'}$, $R^{1''}$, $R^{1'''}$, $R^2$ and $R^3$ are each independently selected from the group consisting of H, halogen, cyano, $CF_3$, $(C_1-C_8)$alkyl, $(C_1-C_8)$alkylthio, $(C_1-C_8)$alkoxy, aryl, heteroaryl, $L^f$ and $P^z$; wherein the alkyl portions of any of $R^{1'}$, $R^{1''}$, $R^{1'''}$ and $R^1$ through $R^3$ are optionally substituted with halogen, carboxy, sulfa, amino, mono- or dialkylamino, alkoxy, cyano, haloacetyl or hydroxy, and the alkyl portions of the substituents have from 1 to 6 carbon atoms; and the aryl and heteroaryl portions of any of $R^{1'}$, $R^{1''}$, $R^{1'''}$ and $R^1$ through $R^3$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$; and $A^1$ represents O or N—Z, in which Z is H or $(C_1-C_8)$alkyl.

The benzocoumarin series (VI) of dyes are those of formula V in which $R^2$ and $R^3$ are combined to form a fused benzene ring, optionally substituted with one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy.

Cyanine Dyes

In still other embodiments, the present invention provides cyanine dye reagents having the general formula above wherein FL is a cyanine dye component.

A variety of cyanine dyes are useful in the present invention and generally have the a formula as provided below.

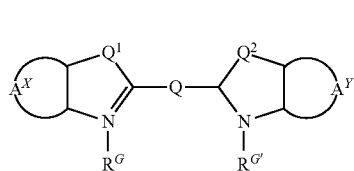

(VII)

In the above formula, each of $Q^1$ and $Q^2$ are independently selected from O, S, N and $CR^aR^b$ or —C(=$CH_2$)— wherein $R^a$ and $R^b$ are independently H, methyl, ethyl or a linking group (e.g., $L^f$). The rings $A^x$ and $A^y$ independently represent condensed substituted or unsubstituted aryl or heteroaryl rings (see Table 1 below), wherein the aryl or heteroaryl rings are optionally substituted as provided in formula (I) above. The letter Q represents a conjugated linking system. Suitable conjugated linking systems are those below (wherein R is H, lower alkyl or $L^f$) as well as the conjugated systems provided in the table of cyanine dyes.

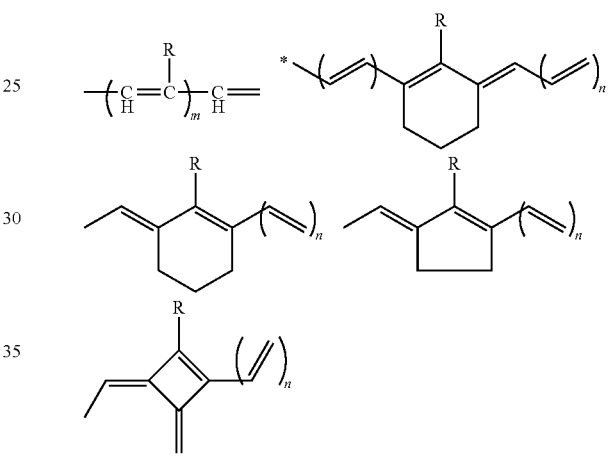

Returning to the cyanine dye formula above, the symbols $R^G$ and $R^{G'}$ are independently selected from H, $C_1-C_8$ alkyl, heteroalkyl, alkylene sulfonic acid, alkylene carboxylic acid, a linking group (e.g., $L^f$) and $P^z$ and wherein one or two aryl or heteroaryl zwitterionic phosphonate groups ($P^z$) are present and wherein a linker moiety present in $R^a$, $R^b$, R, $A^X$ or $A^Y$ contains a functional group such as a N, O or S nucleophile, or contains a functionality capable of reacting with N, O or S nucleophiles.

While the above formula is intended to convey the scope of cyanine dyes that can be modified according to the methods described herein, the term "cyanine dyes" or "cyanines" refers to any of the cyanine dyes that are well known in the art. Synthetic approaches have been disclosed in EP 1,065,250; WO 05/014723; WO 99/31181; U.S. Pat. Nos. 5,268,486; 5,658,751; 5,808,044; 5,981,747; 5,658,751; 4,937,198; 4,937,198; 6,080,868; 6,110,630; 6,225,050; 6,238,838; 6,716,994 and 6,207,464, as well as U.S. Publication No. 2003/0113755. Representative examples of known cyanine dyes are shown in Table 1. It will be appreciated by those of skill in the art that the synthesis of dyes of Table 1 can be modified to yield halogenated dyes which can be converted to the zwitterionic phosphonate dyes using the general methods described herein. In addition, substituents, linkers or linking groups with appropriate reactive functional groups can be incorporated in these dyes or dye analogs by other standard methods known in the art.

TABLE 1
Known Cyanine Dyes
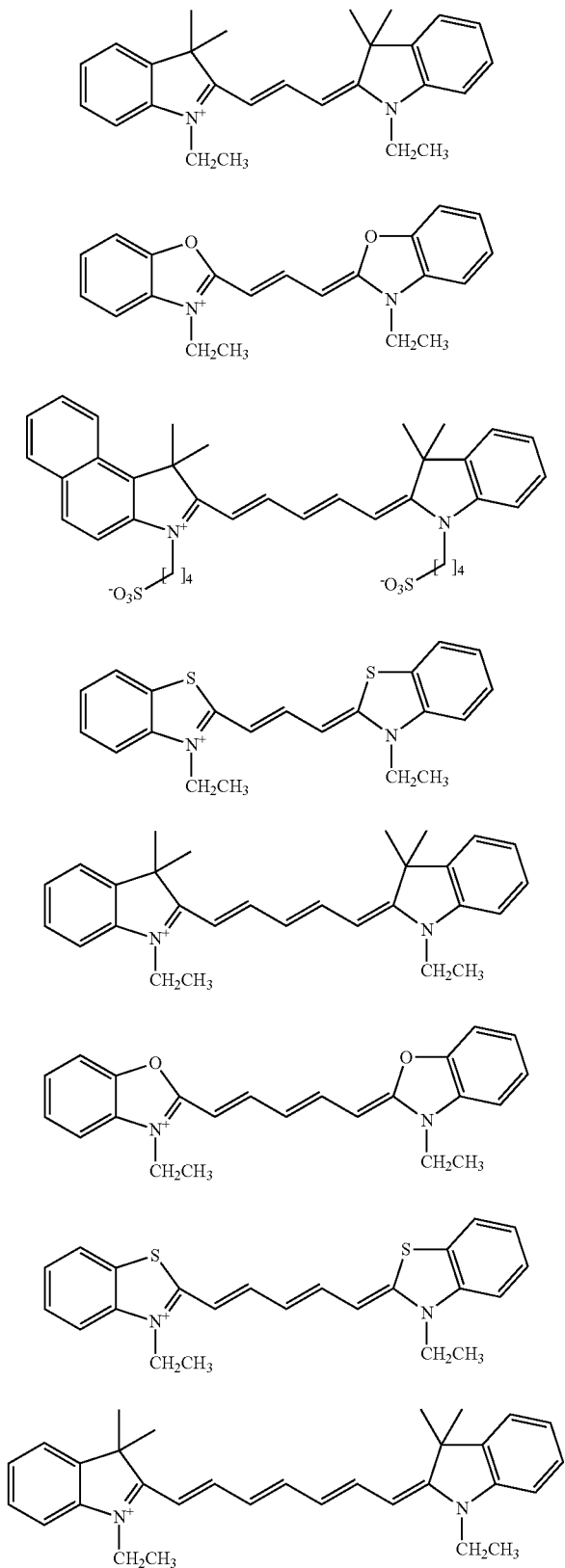

TABLE 1-continued
Known Cyanine Dyes
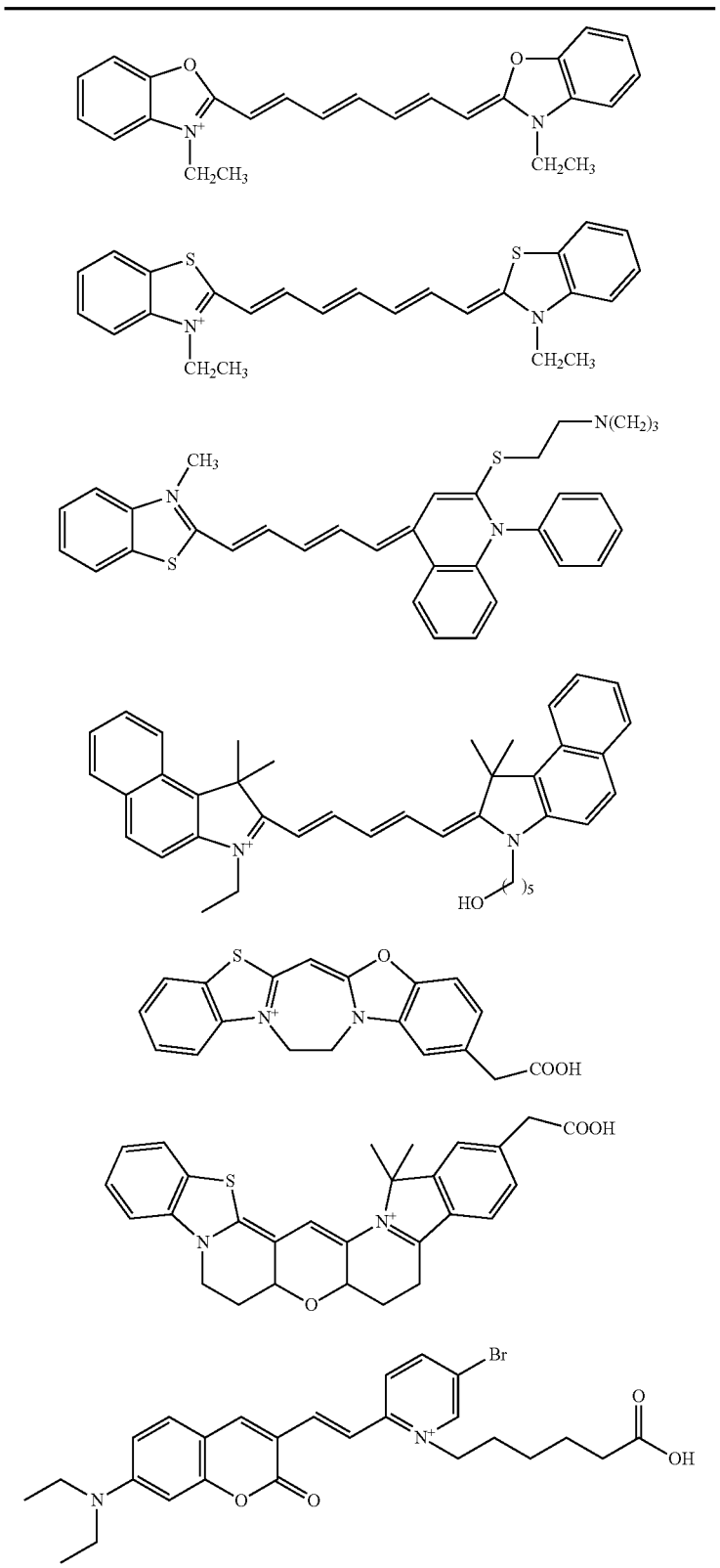

TABLE 1-continued

Known Cyanine Dyes

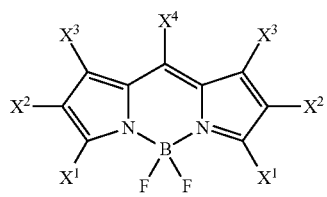

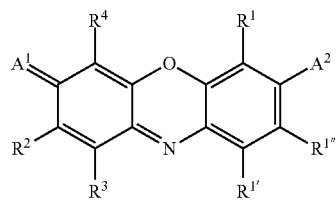

Dipyrromethenboron Difluoride Dyes (Bodipy Dyes)

Phosphonate dipyrrometheneboron difluoride dyes are provided as shown in the formula:

(VIII)

wherein $X^1$, $X^2$, $X^3$, and $X^4$, are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$, $PO_3H_2$, $CO_2H$, $L^f$ and $P^z$ and optionally, any two adjacent $X^1$ through $X^4$ are combined to form a non-aromatic, aromatic or hetero aromatic five or six-membered ring that is optionally further substituted with from one to four substituents selected from halogen, cyano, carboxy, sulfo, hydroxy, amino, mono- or di($C_1-C_6$)alkylamino, ($C_1-C_6$)alkyl, ($C_1-C_6$)alkylthio and ($C_1-C_6$)alkoxy. Within the above formulae (VIII), there are from 0 to 1 $L^f$ groups and from 1 to 2 $P^z$ groups.

Phenoxazine Dyes

In still another group of embodiments, the fluorescent dye reagents have the formula:

(IX)

wherein $A^1$ represents O or N—Z in which Z is H or $(C_1-C_8)$ alkyl, or is optionally combined with $R^2$ or $R^4$ to form a 5- or 6-membered ring or is combined with each of $R^2$ and $R^4$ to form two fused 6-membered rings; $A^2$ represents OR or $N(Z)_2$ in which each Z and R is H or $(C_1-C_8)$alkyl, or is optionally combined with $R^1$ or $R^{1'''}$ to form a 5- or 6-membered ring or is combined with each of $R^1$ and $R^{1'''}$ to form two fused 6-membered rings.

The symbols $R^{1'}$, $R^{1''}$, $R^1$, $R^2$, $R^3$ and $R^4$ are each independently selected from H, halogen, cyano, $CF_3$, $(C_1-C_8)$alkyl, $(C_1-C_8)$alkylthio, $(C_1-C_8)$alkoxy, aryl, heteroaryl, $L^f$ and $P^z$; wherein the alkyl portions of any of $R^{1'}$, $R^{1''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$, $R^{1''}$ and $R^1$ through $R^4$ are optionally substituted with from one to four substituents selected from the group consisting of halogen, cyano, carboxy, sulfo, hydroxy, amino, mono- or di($C_1-C_6$)alkylamino, ($C_1-C_6$)alkyl, ($C_1-C_6$)alkylthio, ($C_1-C_6$)alkoxy, $L^f$ and $P^z$, such that within the above formula there will be from 0 to 1 $L^f$ groups and from 1 to 4 $P^z$ groups, preferably 1 to 2 $P^z$ groups.

Figure 2:
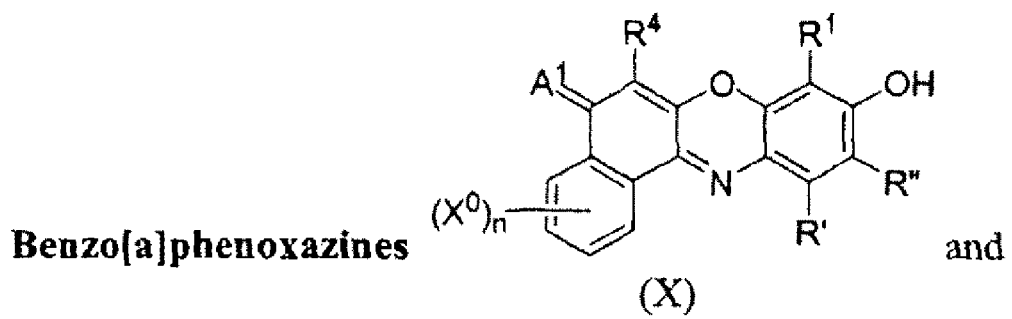
FIG. 2 illustrates the structures selected classes of benzophenoxazine dyes of the present invention.
Figure 2:
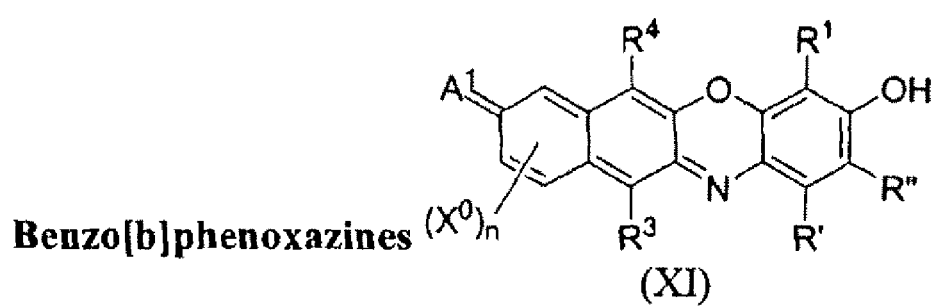
Figure 2:
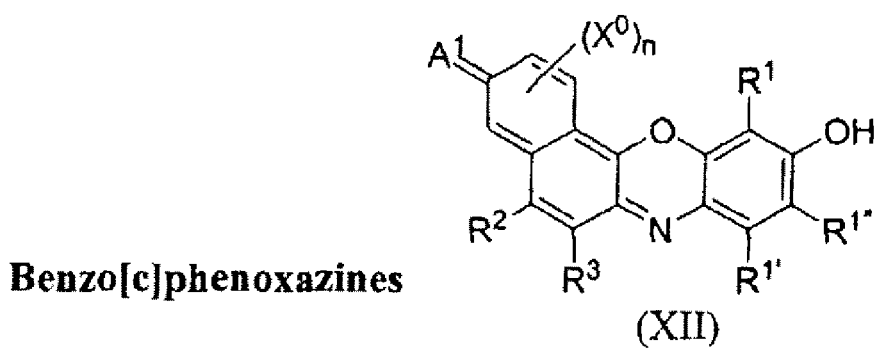

In still other embodiments of the invention. FL is a phenoxazine dye such as, for example, a benzo[a]phenoxazine dye, a benzo[b]phenoxazine dye, or a benzo[c]phenoxazine dye (see formula X, XI and XII in FIG. 2 wherein the substituents have the meanings provided above, and in addition the subscript n in each of the formulae is an integer of from 0 to 3 and each $X^0$ is selected from the group consisting of halogen, cyano, $CF_3$, $(C_1\text{-}C_8)$alkyl, $(C_1\text{-}C_8)$alkoxy, $(C_1\text{-}C_8)$alkylthio, $(C_2\text{-}C_8)$alkenyl, $(C_2\text{-}C_8)$alkynyl, aryl, heteroaryl, $SO_3H$, $PO_3H_2$, $CO_2H$, $L^f$ and $P^z$ and any aryl or heteroaryl portions of $X^0$ are optionally substituted with from one to four substituents selected from the group consisting of halogen, cyano, carboxy, sulfo, hydroxy, amino, mono- or di($C_1\text{-}C_6$)alkylamino, $(C_1\text{-}C_6)$alkyl, $(C_1\text{-}C_6)$alkylthio, $(C_1\text{-}C_6)$alkoxy, $L^f$ and $P^z$).

Transition Metal Complexes

Phosphonate metal complexes such as 2,2'-dipyryl-based ruthenium (II) complexed dyes are provided as shown in the formula:

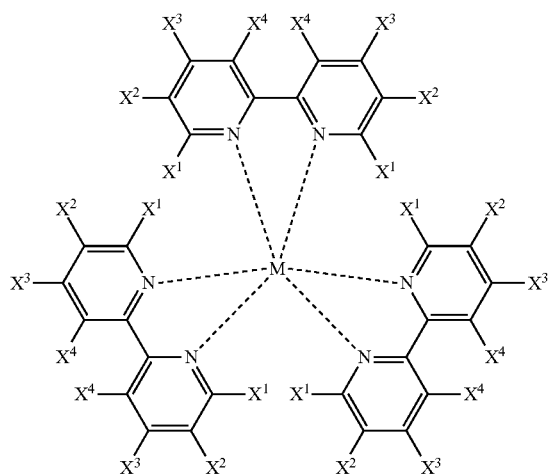

(XIII)

wherein each of $X^1$, $X^2$, $X^3$ and $X^4$ is independently selected from H, OH, halogen, cyano, $CF_3$, $(C_1\text{-}C_8)$alkyl, $(C_1\text{-}C_8)$alkylthio, $(C_1\text{-}C_8)$alkoxy, aryl, heteroaryl, $L^f$ and $P^z$; wherein the alkyl portions of any of $X^1$, $X^2$, $X^3$ and $X^4$ are optionally substituted with halogen, carboxy, carboxy esters, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $X^1$, $X^2$, $X^3$ and $X^4$ are optionally substituted with from one to four substituents selected from the group consisting of halogen, cyano, carboxy, sulfo, hydroxy, amino, mono- or di($C_1\text{-}C_6$)alkylamino, $(C_1\text{-}C_6)$alkyl, $(C_1\text{-}C_6)$alkylthio, $(C_1\text{-}C_6)$alkoxy, $L^f$ and $P^z$; or optionally, any adjacent combination of two $X^{1\text{-}4}$ form saturated or unsaturated substituted or unsubstituted 5- or 6-member rings which contain 0, 1 or more heterocyclic ring atoms selected from N or S. M is a metal ion selected from a lanthanide metal and a transition metal. Within the above formula (XIII), there will be from 0 to 1 $L^f$ groups and from 1 to 2 $P^z$ groups.

In another related embodiment one of $X^{1\text{-}4}$ is $L^f$ or $P^z$ and the remainder of $X^{1\text{-}4}$ are hydrogen.

In a still another related embodiment, M is horn ruthenium, rhenium or selected osmium.

In another exemplary embodiment, the metal ion complex is stable to nucleic acid synthesis conditions, as well as nucleic acid deprotection and cleavage reagents.

Other Phosphonate Dyes

A variety of other dyes can be modified into the dye reagents of the present invention, employing the methods described herein, Still other synthetic methods useful in the transformations are known to one skilled in the art. In particular, the dye can be prepared by, a) halogenation to allow introduction of the phosphonate group and b) be made reactive to various functional groups on biological agents or material proteins, peptides, oligonucleotides, substrates and the like (see Table 2). Known fluorescent dye structures are shown in Table 2 in the left column. An example of a halogenated dye precursor based on the dye structure in the left column is shown in the right column of Table 2. Those skilled in the art will appreciate that the phosphonate group can be introduced into any of the halogenated rings or where halogenation is possible. In addition, groups to attach the phosphonate dyes to biological materials can be introduced in various positions in dyes of Table 2. It will further be appreciated that the proposed dyes of Table 2 not only contain one or more phosphonate group, a group for the attachment of the dye to a biological or other substrate, but can optionally contain one or more substituents on any of the rings to modulate the fluorescence emission properties.

TABLE 2

Structure and Physical Properties of Known Dyes and the Structure of Halogenated Dyes

| Known Dye | Halogenated Dye Precursor |
|---|---|
| 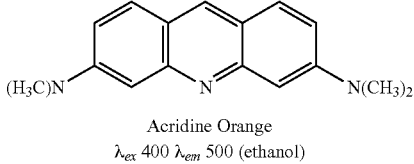 Acridine Orange $\lambda_{ex}$ 400 $\lambda_{em}$ 500 (ethanol) | 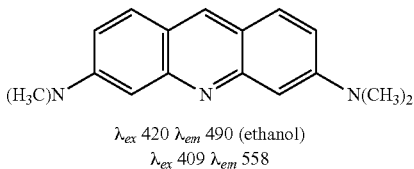 $\lambda_{ex}$ 420 $\lambda_{em}$ 490 (ethanol) $\lambda_{ex}$ 409 $\lambda_{em}$ 558 |
| 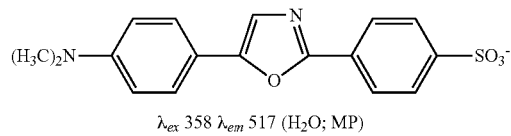 $\lambda_{ex}$ 358 $\lambda_{em}$ 517 ($H_2O$; MP) | 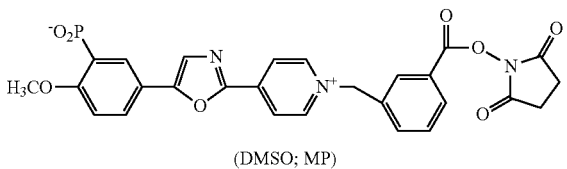 (DMSO; MP) |

TABLE 2-continued

Structure and Physical Properties of Known Dyes
and the Structure of Halogenated Dyes

| Known Dye | Halogenated Dye Precursor |
|---|---|

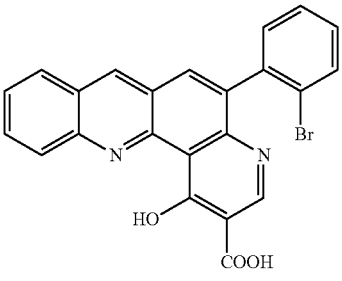

U.S. Pat. No. 4,060,527

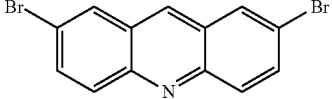

Zeitschrift fuer Angewandte Physik, 14: 43-8 (1962)

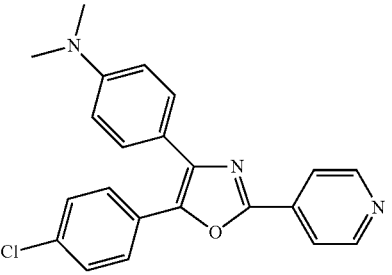

U.S. Pat. No. 3,257,203

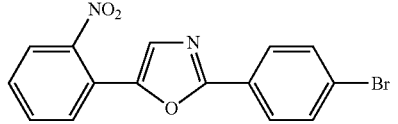

Tetrahedron Letters 1321-1324 (1976)

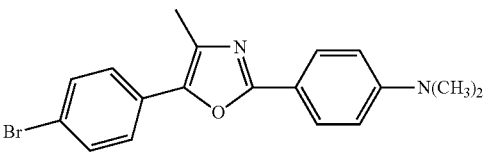

J. Combinatorial Chemistry 7: 463-473 (2005)

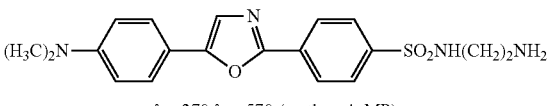

$\lambda_{ex}$ 370 $\lambda_{em}$ 570 (methanol; MP)

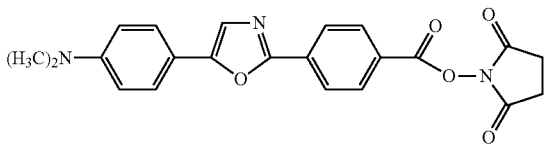

$\lambda_{ex}$ 395 $\lambda_{em}$ 601 (methanol; MP)

TABLE 2-continued

Structure and Physical Properties of Known Dyes
and the Structure of Halogenated Dyes

| Known Dye | Halogenated Dye Precursor |
|---|---|

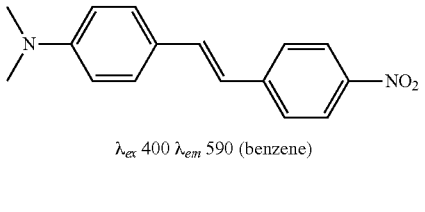

$\lambda_{ex}$ 420 $\lambda_{em}$ 620 (methanol)

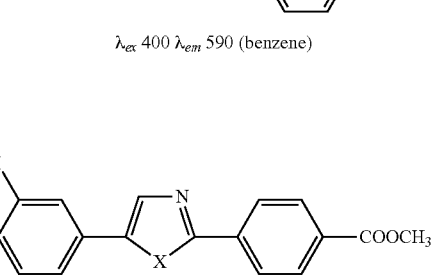

$\lambda_{ex}$ 400 $\lambda_{em}$ 590 (benzene)

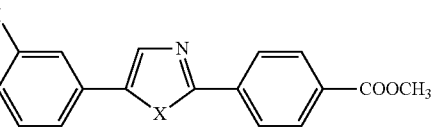

X = O or S
WO 04014366

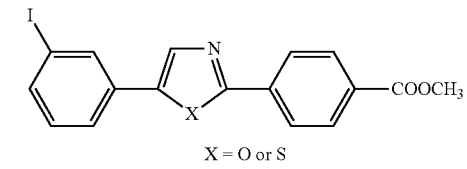

n = 0 or 2
Gaodeng Xuexiao Huaxue Xuebao 13: 1251-4 (1992) or
CAN 119: 8716

J de Chimie Phys. et de Physico-Chimie Biol., 75: 961-8 (1978)

TABLE 2-continued

Structure and Physical Properties of Known Dyes
and the Structure of Halogenated Dyes

| Known Dye | Halogenated Dye Precursor |
|---|---|

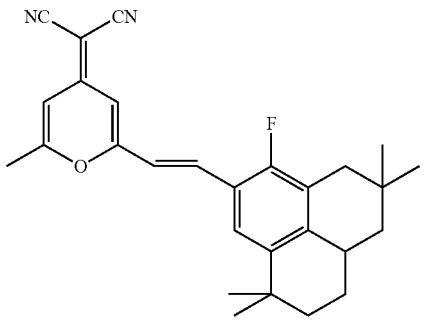

Materials Res. Soc. Symp. Proceed. (2001), 677

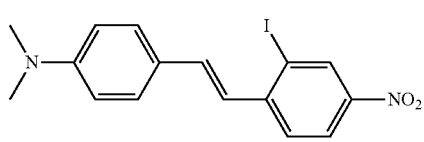

Helvitica Chim. Acta, 23: 292-302 (1940)

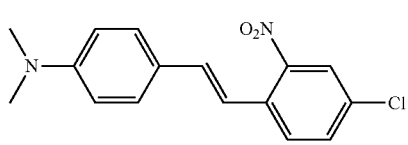

Helvitica Chim. Acta, 23: 292-302 (1940)

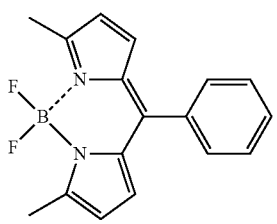

$\lambda_{ex}$ 485 $\lambda_{em}$ 530 (toluene)

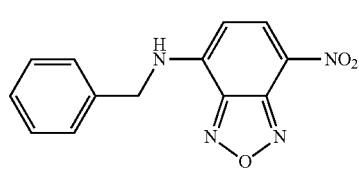

$\lambda_{ex}$ 410 $\lambda_{em}$ 520 (Ethanol)

TABLE 2-continued

Structure and Physical Properties of Known Dyes
and the Structure of Halogenated Dyes

| Known Dye | Halogenated Dye Precursor |
|---|---|

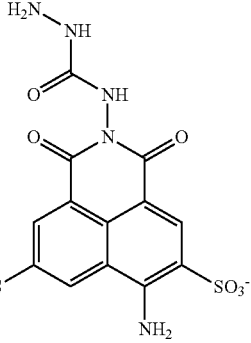

$\lambda_{ex}$ 380 $\lambda_{em}$ 540 (water)

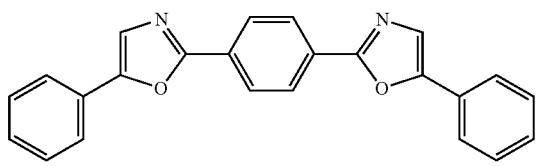

$\lambda_{ex}$ 350 $\lambda_{em}$ 410, 470 (hexane)

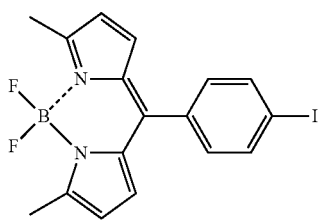

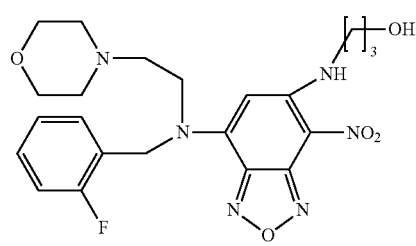

http://www.interchim.com

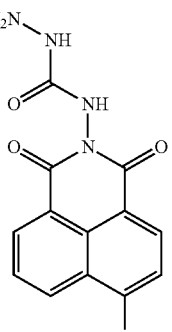

J. Org. Chem., 42: 2426 (1997)

TABLE 2-continued

Structure and Physical Properties of Known Dyes and the Structure of Halogenated Dyes

| Known Dye | Halogenated Dye Precursor |
|---|---|
| U.S. Pat. No. 3,843,632 | |
| U.S. Pat. No. 3,843,632 | |
| $\lambda_{ex}$ 410 $\lambda_{em}$ 430, 460, 490 (cyclohexane) | |
| $\lambda_{ex}$ 350 $\lambda_{em}$ 500 (water) | |
| $\lambda_{ex}$ 336 $\lambda_{em}$ 450 (cyclohexane) | |
| Ber., 73B: 1187-92 (1940) | |
| Monalsh. 52: 1-6 (1929) (CAN 23: 36005) | |
| | Internat. J. of Radiat. Biol., 66: 517-21 (1994) |
| | Tetrahedron Letters, 915-920 (1963) |
| | Zhurnal Obshchei Khimtl, 49: 167-1670 (1979) |
| | EP 1408366 |

Unless otherwise indicated, the excitation and emission wavelengths were taken from the chemical spectra from the PhotochemCAD package by Jonathan Lindsey. (http://omlc.ogi.edu/spectra/PhotochemCAD/html/).

The emission wavelengths were estimated from the emission spectra.

The halogenated dye intermediates shown in Table 2 can be converted to the phosphonate dyes by the methods of the invention. It will be apparent to those skilled in the art that fluorescent dyes reported in the art can be converted to the corresponding halogenated dye by a variety of methods. One such method is to start with a halogenated dye intermediate or in some instances it will be possible to introduce a halogen substituent into one of its aromatic rings. It will be further apparent that a linker moiety can be introduced into the dye molecule by methods known in the art or those taught by this invention. Halogenation of aromatic rings with chlorine and bromine is well known in the art, for a review see Breandlin and McBee, in Olah, "FRIEDEL-CRAFTS AND RELATED REACTIONS" Vol 3, pp 1517-1593, Interscience Publishers, Inc. NY, 1964 and Berliner, *J. Chem. Ethic.* 43:124-132 (1966)). Alternatively the halide group can be introduced into a aromatic ring via diazotization of an amino group using the Sandmeyer reaction (Hodgson, *Chem. Rev.,* 40:251-277 (1947)). It will further be apparent to those skilled in the art that aryl and heteroaryl moieties present in the dyes of Table 2 can be substituted. Substituents can be introduced in the dyes by methods known in the art. As a result, the structure analogs (e.g., those optionally incorporating $L^f$ and $P^z$) of the dyes of Table 2 are also contemplated as specific embodiments of the present invention.

Energy Transfer Dyes

Phosphonate energy transfer dyes are another example of the dye reagents of the present invention. One example of such energy transfer dyes is the electron-donating and electron-accepting xanthene dye couple shown below. One of skill in the art will appreciate that other dye combinations are also part of the present invention.

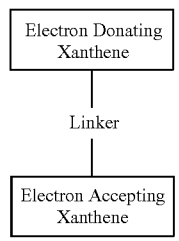

More particularly, the electron transfer dyes employing xanthene moieties can include essentially any of the xanthene dyes (e.g. those provided above in Formulae I, Ia and Ib) or the benzoxanthene dyes. The linker portion can be a variety of linkers, generally having from about 3 to 50 main atoms selected from C, N, O, P and S which is either cyclic, acyclic, aromatic or a combination thereof, and having additional hydrogen atoms to fill available valences. Examples of energy transfer dyes have been disclosed in U.S. Pat. Nos. 5,800,996; 5,863,727 and 5,565,554; and in European Patent No. 0 747 700. Table 4 illustrates a few examples of energy transfer dyes that can be modified according to the methods described herein to attach a phosphonate moiety (and optionally a further linking group as provided in the general formula above).

TABLE 4

Examples of Dimeric Fluorescence Energy Transfer Dyes

Example $4^1$ $4^2$

TABLE 4-continued
Examples of Dimeric Fluorescence Energy Transfer Dyes
Example
4³
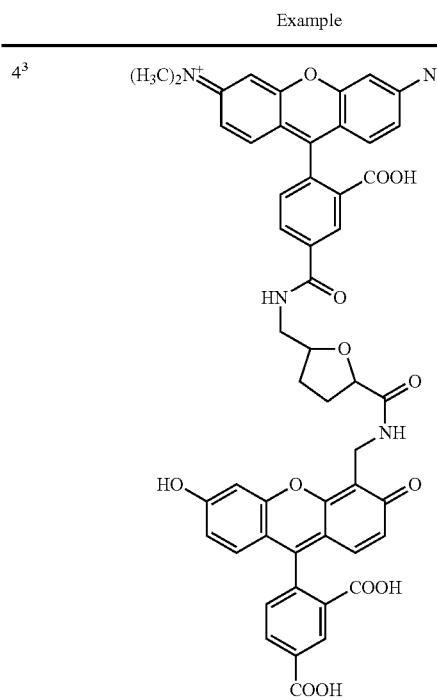
4⁴
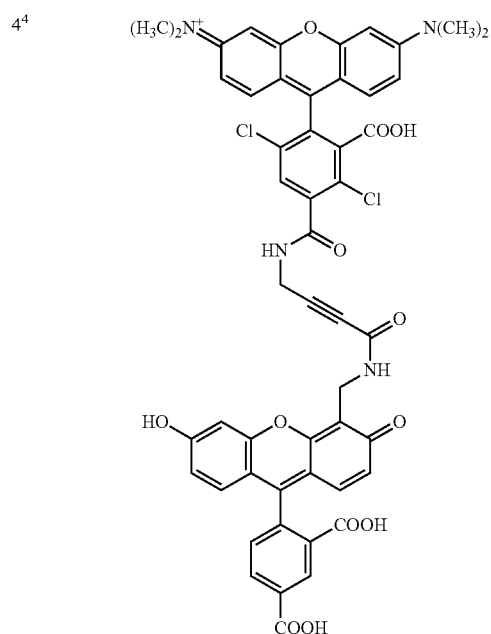
4⁵
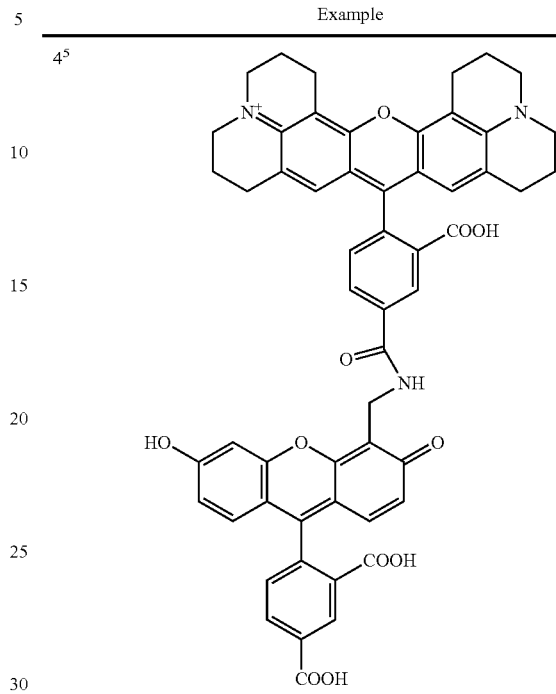
4⁶

TABLE 4-continued

Examples of Dimeric Fluorescence Energy Transfer Dyes

Example

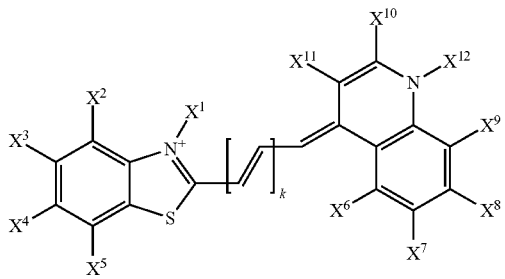

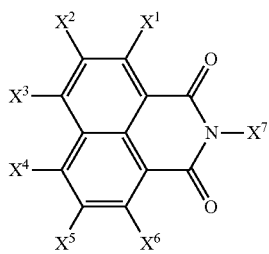

Synthetic procedures for the dimeric energy transfer dyes shown in Table 4 have been described in, for example, U.S. Pat. Nos. 5,800,996, 5,863,727 and 5,565,554, and in European Patent. No. 0 747 700. Fluorescent energy transfer tags that contain more than two fluorescent moieties are described in U.S. Pat. No. 6,627,748. The dyes in Table 4 contain at least one xanthene moiety or at least one cyanine moiety and the introduction of a phosphonate group into the xanthene- or cyanine-dyes can be readily accomplished by the methods described herein.

Thiazole Orange Analogs

In still other embodiments, phosphonate thiazole orange fluorescent dye reagents are provided as shown in the formula (XIV)

wherein $X^2$, $X^3$, $X^4$, $X^5$, X, $X^7$, $X^8$, $X^9$, $X^{10}$ and $X^{11}$ are each independently selected from H, halogen, cyano, $CF_3$, $(C_1\text{-}C_8)$ alkyl, $(C_1\text{-}C_8)$alkylthio, $(C_1\text{-}C_8)$alkoxy, aryl, heteroaryl, $L^f$ and $P^z$; or optionally two adjacent members of $X^2$ through $X^{11}$ are combined to form a five or six membered fused ring that is aromatic, non-aromatic or heteroaromatic and with is optionally substituted with $P^z$; and $X^1$ and $X^{12}$ are each independently H, $(C_1\text{-}C_6)$alkyl, aryl and substituted aryl; wherein the alkyl portions of any of $X^1$ through $X^{12}$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $X^1$ through $X^{12}$ are optionally substituted with from one to four substituents selected from the group consisting of halogen, cyano, carboxy, sulfo, hydroxy, amino, mono- or di$(C_1\text{-}C_6)$alkylamino, $(C_1\text{-}C_6)$alkyl, $(C_1\text{-}C_6)$alkylthio, $(C_1\text{-}C_6)$alkoxy, $L^f$ and $P^z$.

N-Aryl-1,8-naphthalimides

Phosphonate-Aryl-1,8-naphthalimides analogs are provided as show in the formula XV (XV)

wherein $X^1$, $X^2$, $X^3$, $X^4$, $X^5$, $X^6$ are each independently selected from H, halogen, cyano, $CF_3$, $(C_1\text{-}C_8)$alkyl, $(C_1\text{-}C_8)$ alkylthio, $(C_1\text{-}C_8)$alkoxy, aryl, heteroaryl, $L^f$ and $P^z$; or optionally two adjacent members of $X^1$ through $X^6$ are combined to form a five or six membered fused ring that is aromatic, non-aromatic or heteroaromatic and with is optionally substituted with P$^z$; and X$^7$ is aryl or heteroaryl; wherein the alkyl portions of any of X$^1$ through X$^6$ are optionally substituted with halogen, carboxy, sun, amino, mono- or dialkylamino, alkoxy, cyano, haloacetyl or hydroxy, and the alkyl portions of the substituents have from 1 to 6 carbon atoms; and the aryl or heteroaryl portions of any of X$^1$ through X$^7$ are optionally substituted with from one to four substituents selected from the group consisting of halogen, cyano, carboxy, sulfo, hydroxy, amino, mono- or di(C$_1$-C$_6$)alkylamino, (C$_1$-C$_6$)alkyl, (C$_1$-C$_6$)alkylthio, (C$_1$-C$_6$)alkoxy, L$^f$ and P$^z$.

In a related aspect, the present invention provides fluorescent dye reagents having the general formula (B):

 (B)

wherein Fl is a fluorescent dye component; and P$^1$ is functionalized phosphonate group having the formula:

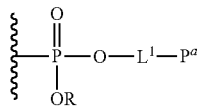

wherein the wavy line indicates the direct attachment to a sp$^2$ carbon of the fluorescent dye component; L$^1$ is a linking group; R is selected from H, (C$_1$-C$_8$)alkyl, aryl, aryl(C$_1$-C$_4$) alkyl, -L$^a$-N$^a$, and -L$^a$-NR$^A$R$^B$; wherein L$^a$ is an alkylene linking group, N$^a$ is an ammonium ion group, and each of R$^A$ and R$^B$ is independently selected from the group consisting of H, (C$_1$-C$_8$)alkyl and a labile protecting group, such as C(O) CF$_3$, FMOC, C(O)t-Butyl, phthalimide and monomethoxytrityl; and P$^a$ is a functional group component selected from the group consisting of a phosphoramidite moiety, a mono-, di- or tri-functional linking group having at least one terminal functional group or protected functional group, a solid support and a reactive group (e.g., an electrophilic or nucleophilic group as described below); and salts thereof. For those embodiments in which R is alkyl, preferred alkyl groups are those that can be removed in the presence of other functional groups in the molecule (e.g., tert-butyl, tert-amyl, methyl)

As with the fluorescent dye reagents described initially, this aspect of the invention includes a variety of fluorescent dye components (Fl) that are typically selected from coumarins, benzocoumarins, xanthenes, benzo[a]xanthenes, benzo[b]xanthenes, benzo[c]xanthenes, cyanines, acridines, dipyrrometheneboron difluorides, phenoxazines, benzo[a]phenoxazines, benzo[b]phenoxazines and benzo[c]phenoxazines. In some embodiments, the fluorescent dye component is selected from coumarin dyes, resorufin dyes, dipyrrometheneboron difluoride dyes, ruthenium bipyridyl dyes, energy transfer dyes, thiazole orange dyes, N-aryl-1,8-naphthalimide dyes, merocyanines, stilbenes, styryl-based dyes and dipyrrins. In still other embodiments, the fluorescent dye component is selected from fluorescein dyes, rhodamine dyes and rhodol dyes. More particularly, the fluorescent dye can be any of the dyes provides in formulae I, Ia, Ib, II, IIa, III, IIIa, IV, IVa, V, VI, VII, VIII, IX, X, XI, XII, XIII or the dyes of Tables 1 or 2, wherein P$^1$ is attached to an sp$^2$-hybridized carbon atom at a position as described above for P.

The phosphonate moiety can be attached to the dye component using methods described herein (e.g., via phosphonylation of a halogen-dye component intermediate) followed by suitable synthesis steps in which the phosphonate is provided with a linkage to terminal group (e.g., P$^a$).

General Synthesis of Phosphonate Dyes

In still another aspect, the present invention provides a method of preparing a phosphonate-fluorescent dye derivative, the method comprising contacting a halo-fluorescent dye substrate having at least one halogen atom attached to an aromatic ring carbon atom, with a phosphite reagent under conditions sufficient to remove the halogen atom and covalently attach a phosphonate group to the aromatic ring carbon atom to form the phosphonate-fluorescent dye derivative.

In a number of embodiments, the halo-fluorescent dye substrate is selected from halo coumarins, halo benzocoumarins, halo xanthenes, halo benzo[a]xanthenes, halo benzo[b]xanthenes, halo benzo[c]xanthenes, halo cyanines, halo acridines, halo dipyrrometheneboron difluorides, halo phenoxazines, halo benzo[a]phenoxazines, halo benzo[b]phenoxazines and halo benzo[c]phenoxazines.

The phosphite reagents of the invention can be symmetric or unsymmetric. Symmetric phosphite reagents are those having the formula: HP(=O)(OR)$_2$, wherein each of the phosphite ester R groups is -L$^a$-NR$^A$R$^B$; wherein L$^a$ is an alkylene linking group, and each of R$^A$ and R$^B$ is independently selected from the group consisting of H, (C$_1$-C$_8$)alkyl and a labile protecting group; and at least one of R$^A$ and R$^B$ is a protecting group. Examples of such protecting groups are C(O)CF$_3$, phthalimide, C(O)Ot-Bu, C(O)OBn, monomethoxytrityl, FMOC, and the like.

Unsymmetric phosphite reagents are those having the formula: HP(=O)(OR)(OR'), wherein the phosphite ester R' group is a protecting group that can be removed in the presence of R or is -L$^a$-NR$^A$R$^B$; and the R group is -L$^1$-P$^a$ or -L$^a$-NR$^A$R$^B$; wherein L$^1$ is an alkylene linking group, and P$^a$ is a protected or unprotected functional group. For each of R and R', L$^a$ is an alkylene linking group, and each of R$^A$ and R$^B$ is independently selected from the group consisting of H, (C$_1$-C$_8$)alkyl and a labile protecting group; and at least one of R$^A$ and R$^B$ is a protecting group. Examples of useful R' ester groups are t-butyl, benzyl, phenyl, and the like. For those embodiments in which R is also -L$^a$-NR$^A$R$^B$; wherein each of R$^A$ and R$^B$ is independently H, (C$_1$-C$_8$)alkyl or a labile protecting group; and at least one of R$^A$ and R$^B$ is a protection group, examples of such protecting groups are C(O)CF$_3$, phthalimide, C(O)Ot-Bu, C(O)OBn, monomethoxytrityl, Fmoc and the like. One of skill in the art will appreciate that for those embodiments in which R$^A$ or R$^B$ is a protecting group, and the R' group is an ester (or protecting group) and the R$^A$ or R$^B$ groups are orthogonal protecting groups (i.e., protecting groups that can be selectively removed in the presence of the other protecting group).

In view of the above, the present invention provides compound having the formula:

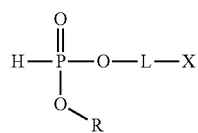

wherein L is a member selected from the group consisting of a (C$_1$-C$_8$)alkylene and (C$_1$-C$_8$)heteroalkylene linking group; X is a member selected from the group consisting of a functional group and a protected functional group wherein said functional group is hydroxy or amino having the formula NR$^A$R$^B$; R is a member selected from the group consisting of a labile protecting group and -L-NR$^A$R$^B$; and each of R$^A$ and R$^B$ is independently selected from H, (C$_1$-C$_8$)alkyl and a labile protecting group and at least one of R$^A$ and R$^B$ is other than H. In some embodiments, R is tertiary butyl. In other embodiments, R is -L-NR$^A$R$^B$, and X is —NR$^A$R$^B$. More preferably, each R$^A$ is H and each R$^B$ is a protecting group, preferably selected from —C(O)CF$_3$, —C(O)OtBu, FMOC, phthalimide and —C(O)O-benzyl. In other embodiments, X is —O-dimethoxytrityl. In the most preferred embodiments, the compound is selected from

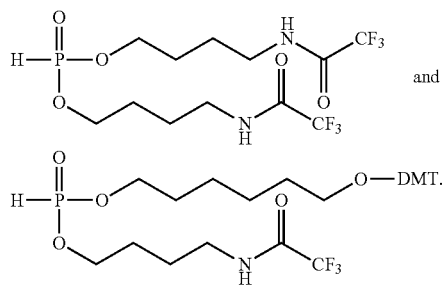

and

While the above structures are provided in a single tautomeric form, one of skill in the art will appreciate the recitation is further meant to include all forms, including the commonly used trivalent phosphite form.

More specific schemes for the preparation of selected phosphite reagents and for their use in preparing fluorescent dye reagents of the present invention are provided in the schemes below.

Reagents for Phosphonate Dye Synthesis and Preparation of Phosphonate Dyes

Reaction Scheme 1 illustrates the synthesis of a symmetric phosphite reagent bis(4-(2,2,2-trifluoroacetamido)butyl) phosphite 3).

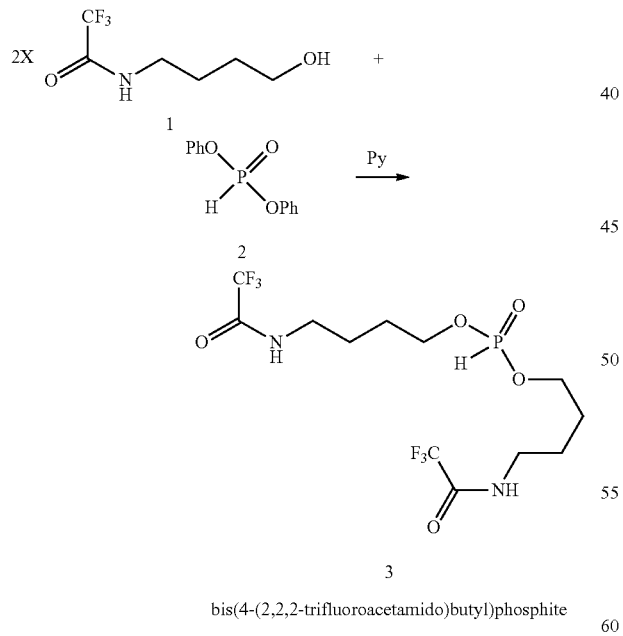

bis(4-(2,2,2-trifluoroacetamido)butyl)phosphite 2,2,2-Trifluoro-N-(4-hydroxybutyl)acetamide (1) was reacted with diphenyl phosphite (2) in pyridine to yield (3). This reagent was used to prepare aromatic bis-trifluoroacetamidophosphonate dyes of the invention. Deprotection of the diester in concentrated NH$_4$OH generates the zwitter ionic 4-aminobutylphosphonate group.

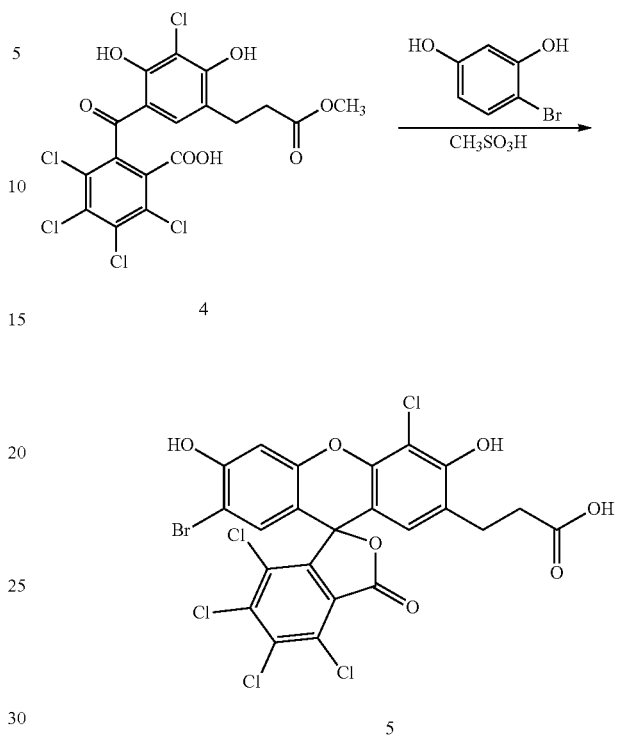

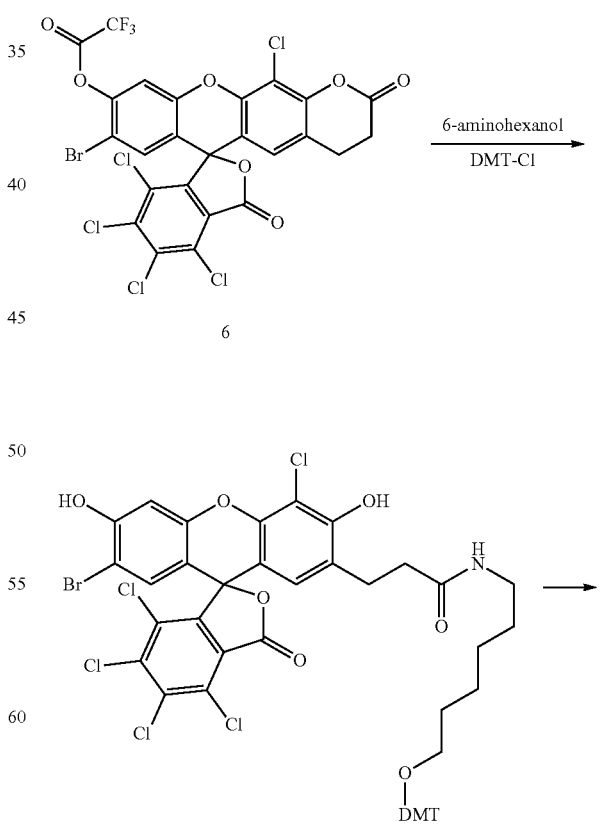

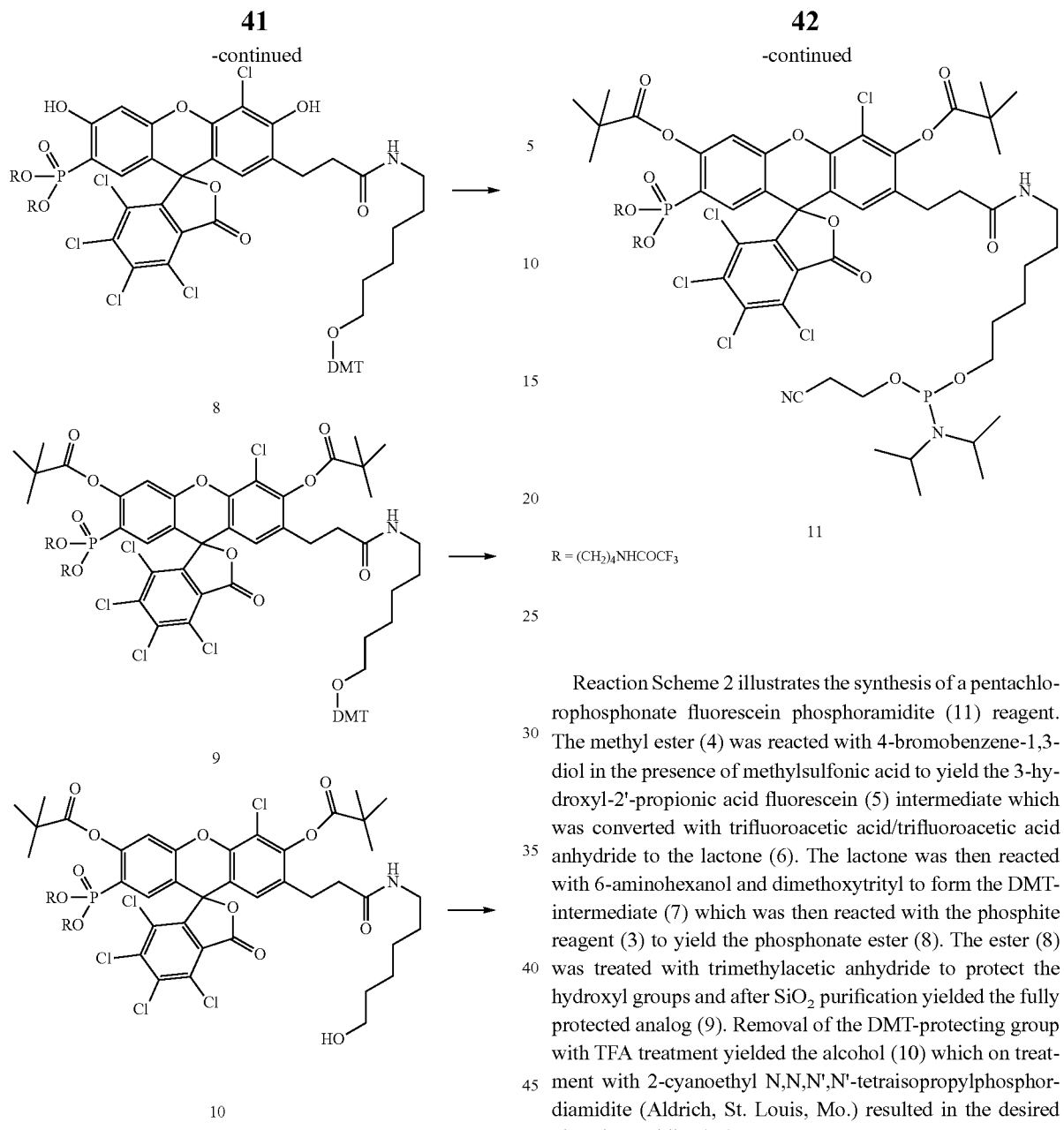

R = (CH₂)₄NHCOCF₃

Reaction Scheme 2 illustrates the synthesis of a pentachlorophosphonate fluorescein phosphoramidite (11) reagent. The methyl ester (4) was reacted with 4-bromobenzene-1,3-diol in the presence of methylsulfonic acid to yield the 3-hydroxyl-2'-propionic acid fluorescein (5) intermediate which was converted with trifluoroacetic acid/trifluoroacetic acid anhydride to the lactone (6). The lactone was then reacted with 6-aminohexanol and dimethoxytrityl to form the DMT-intermediate (7) which was then reacted with the phosphite reagent (3) to yield the phosphonate ester (8). The ester (8) was treated with trimethylacetic anhydride to protect the hydroxyl groups and after $SiO_2$ purification yielded the fully protected analog (9). Removal of the DMT-protecting group with TFA treatment yielded the alcohol (10) which on treatment with 2-cyanoethyl N,N,N',N'-tetraisopropylphosphordiamidite (Aldrich, St. Louis, Mo.) resulted in the desired phosphoramidite (11).

Reaction Scheme 3

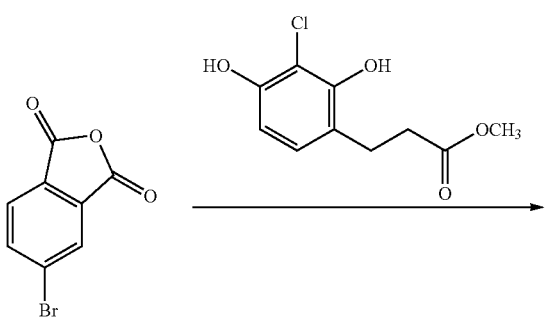

-continued
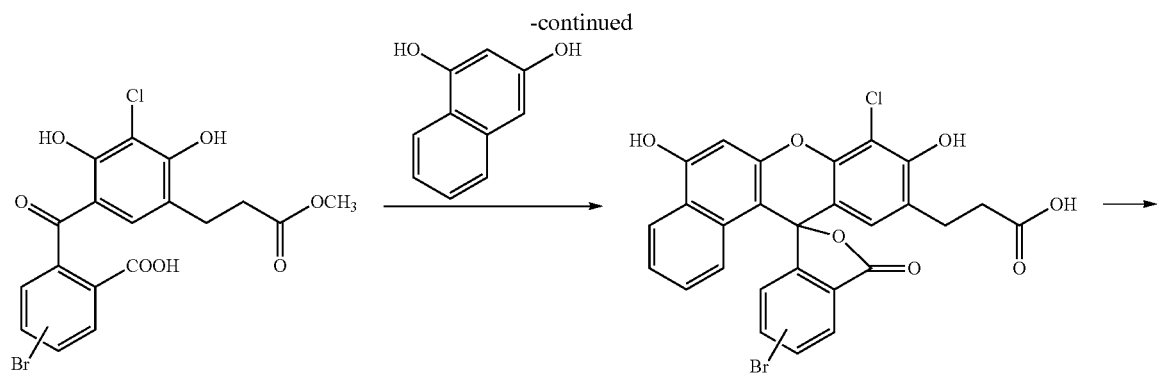
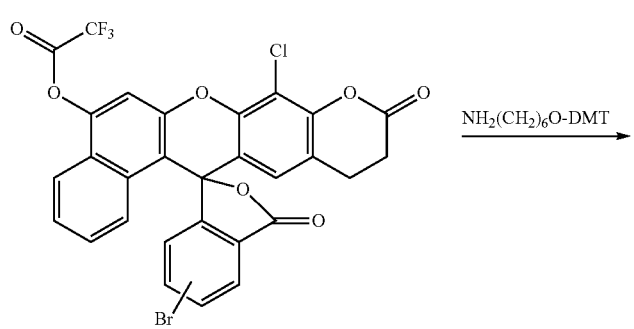
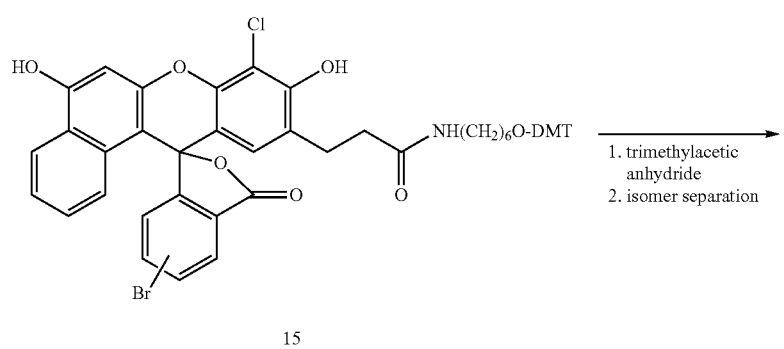
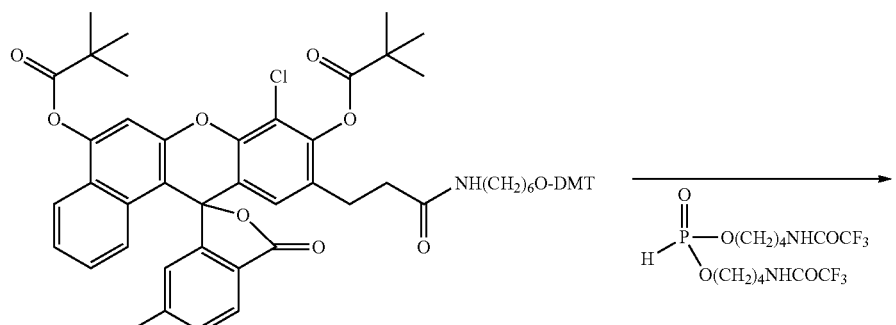

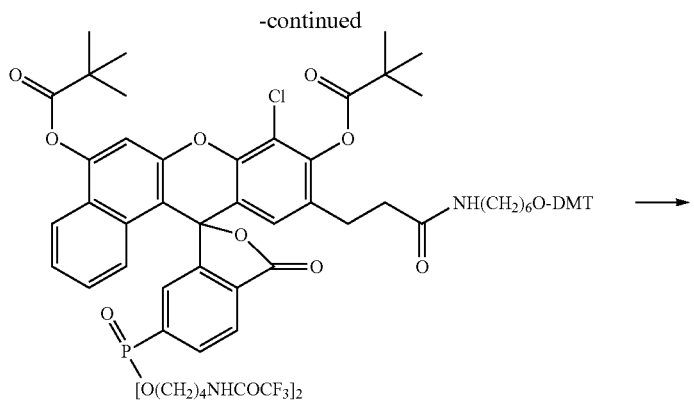

17

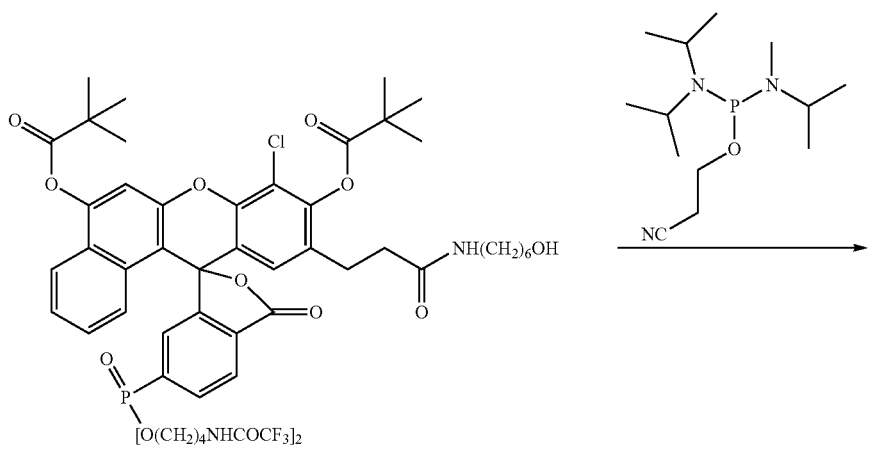

18

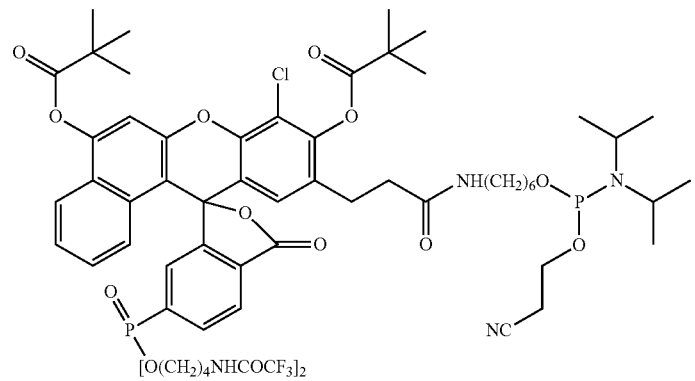

19

Reaction Scheme 3 illustrates the synthesis of a fully protected 4'-chloro-6-phosphonatefluorescein analog (19). 4-Bromophthalic anhydride and methyl-3-(3-chloro-2,4-dihydroxyphenyl)propionate in the presence of AlCl₃ yielded the benzophenone which was reacted to with 1,3-dihydroxynaphthalene to form two isomers of the fluorescein analog (13). Intermediate (13) converted with trifluoroacetic acid/trifluoroacetic acid anhydride to the lactone (14). The lactone was then reacted with O-dimethoxytrityl-6-aminohexanol (*Tetrahedron Letters*, 2004, 45(2):317-320) to form the DMT-intermediate isomers which were separated on silica gel to yield the pure major 6-isomer (15). The 6-isomer was then reacted with trimethyl acetic anhydride to yield the fully protected analog (16) which was reacted with the phosphite reagent (3) to yield the phosphonate ester (17). Removal of the DMT-protecting group with TFA treatment yielded the alcohol (18) which on treatment with 2-cyanoethyl N,N,N', N'-tetraisopropylphosphordiamidite resulted in the desired phosphoramidite (19).
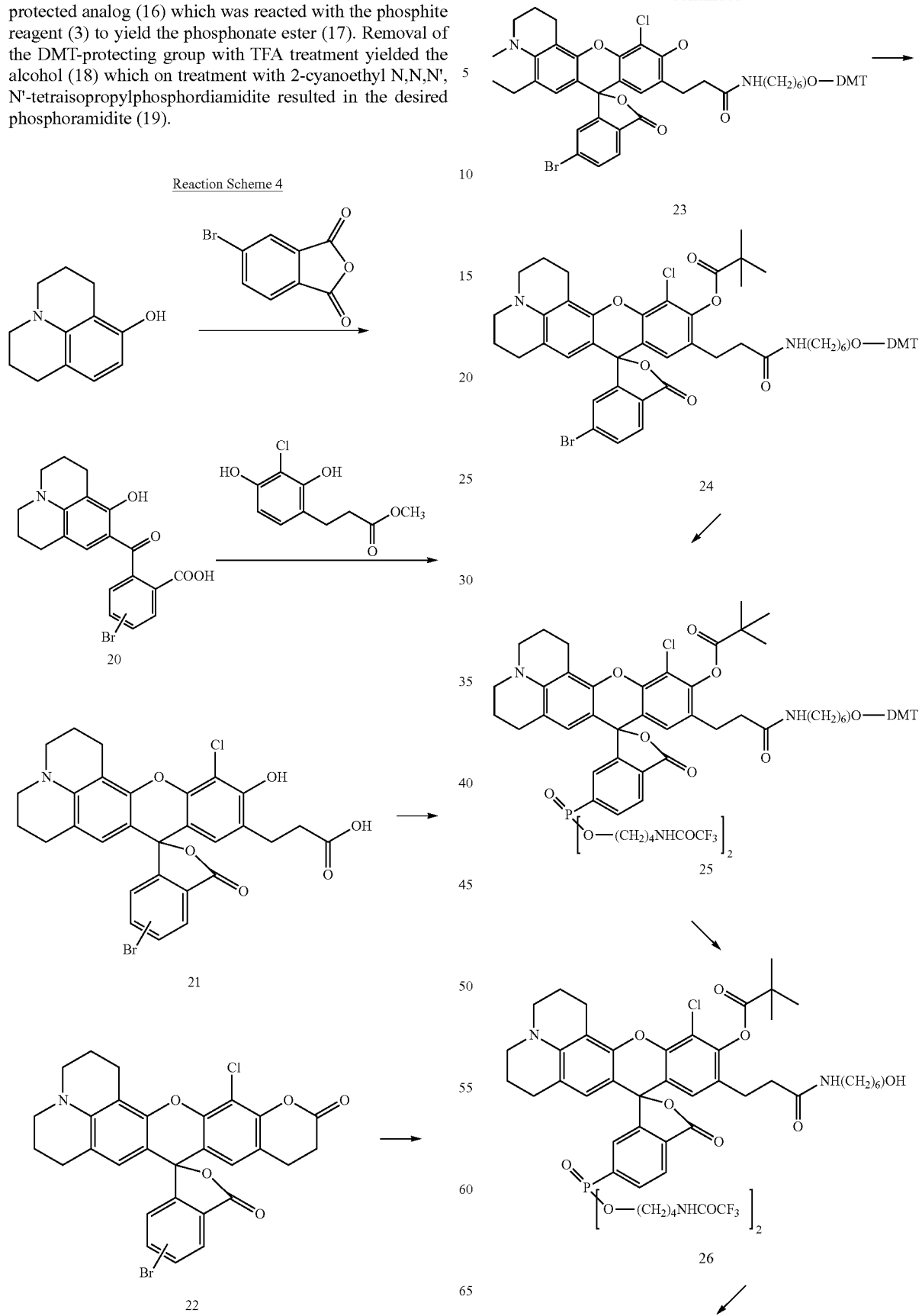

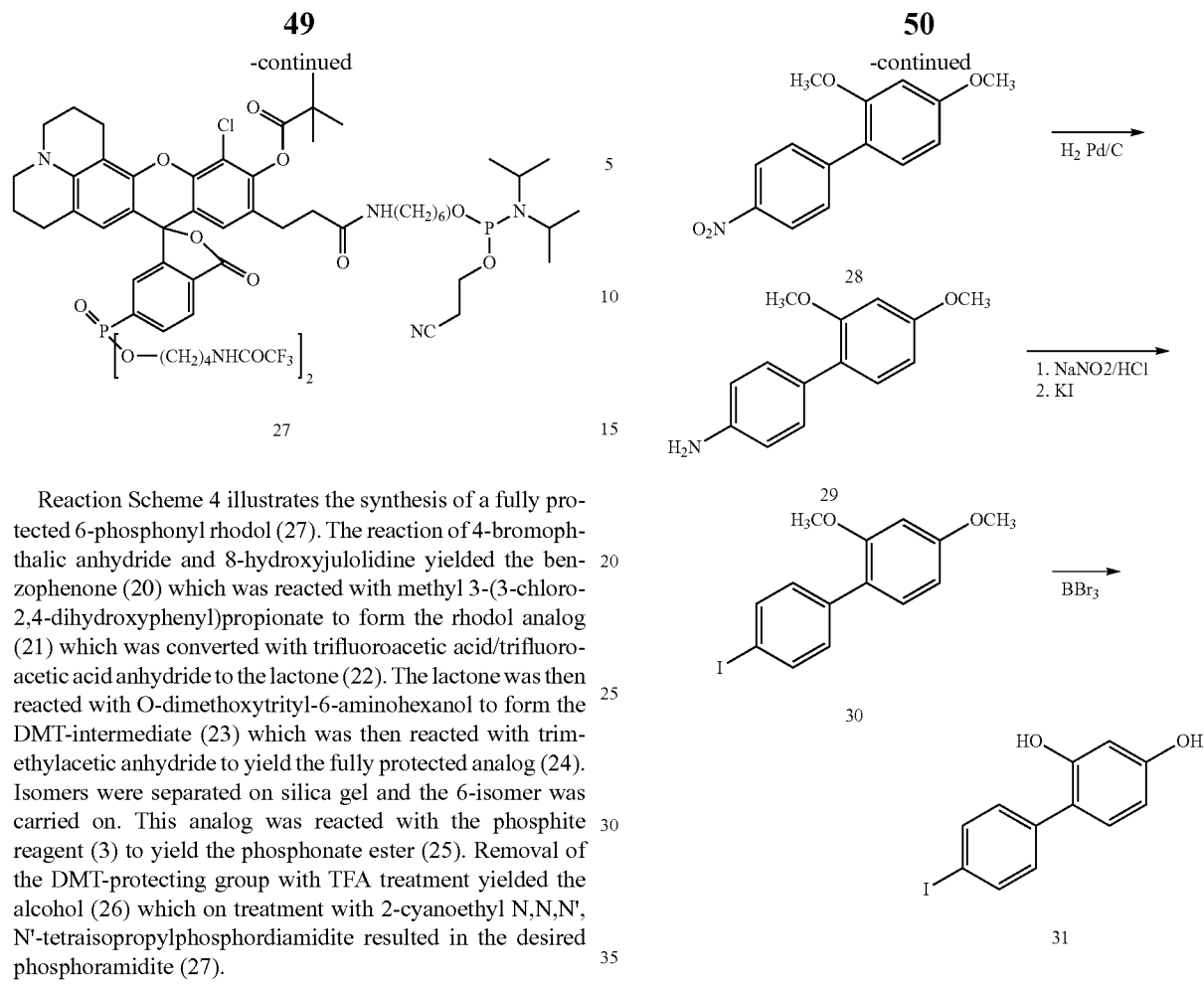

Reaction Scheme 4 illustrates the synthesis of a fully protected 6-phosphonyl rhodol (27). The reaction of 4-bromophthalic anhydride and 8-hydroxyjulolidine yielded the benzophenone (20) which was reacted with methyl 3-(3-chloro-2,4-dihydroxyphenyl)propionate to form the rhodol analog (21) which was converted with trifluoroacetic acid/trifluoroacetic acid anhydride to the lactone (22). The lactone was then reacted with O-dimethoxytrityl-6-aminohexanol to form the DMT-intermediate (23) which was then reacted with trimethylacetic anhydride to yield the fully protected analog (24). Isomers were separated on silica gel and the 6-isomer was carried on. This analog was reacted with the phosphite reagent (3) to yield the phosphonate ester (25). Removal of the DMT-protecting group with TFA treatment yielded the alcohol (26) which on treatment with 2-cyanoethyl N,N,N',N'-tetraisopropylphosphordiamidite resulted in the desired phosphoramidite (27).

Reaction Scheme 5

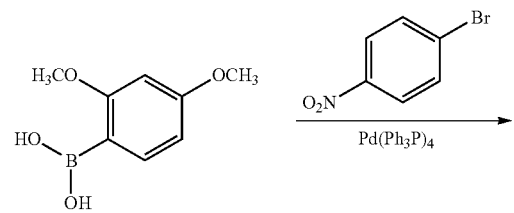

Reaction Scheme 5 illustrates the synthesis of 4-(4-Iodophenyl)resorcinol (31). 2,4-Dimethoxyphenylboronic acid and 1-bromo-4-nitrobenzene in the presence of tetrakis(triphenylphosphine) palladium yielded 4-(4-nitrophenyl)-2,4-methoxybenzene (28). Hydrogenation of 28 in the presence of a palladium catalyst yielded the crude amine (29) which without purification was diazotized and treated with KI solution to yield the desired 4-(4-iodophenyl)-2,4-dimethoxybenzene (30). The dimethoxy analog (30) was treated with boron tribromide to yield the desired 4-(4-iodophenyl)resorcinol (31).

Reaction Scheme 6

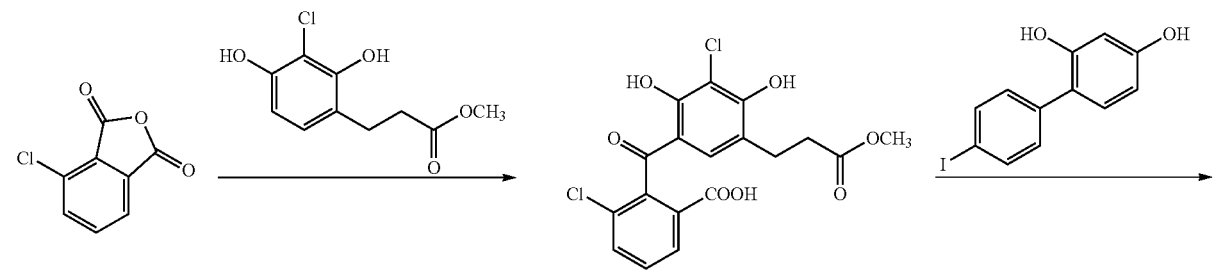

-continued
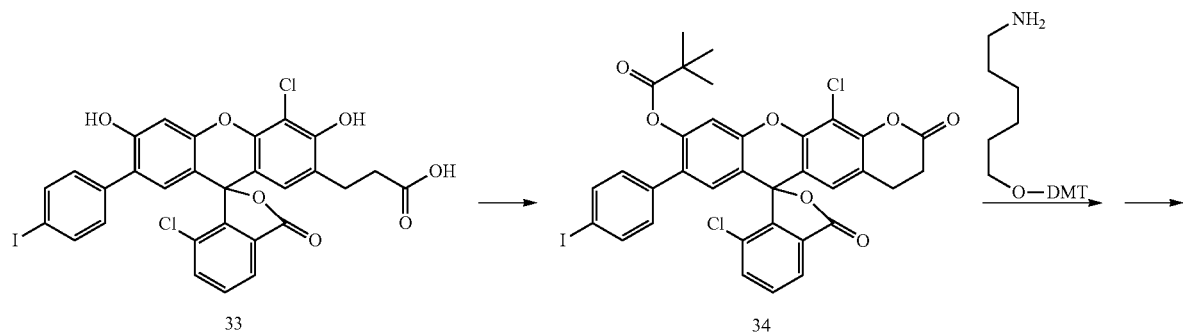
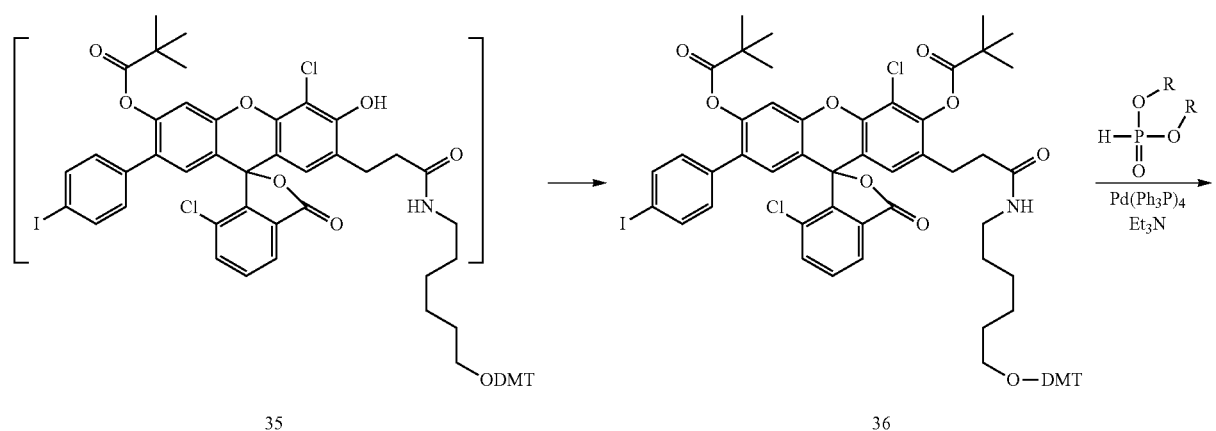
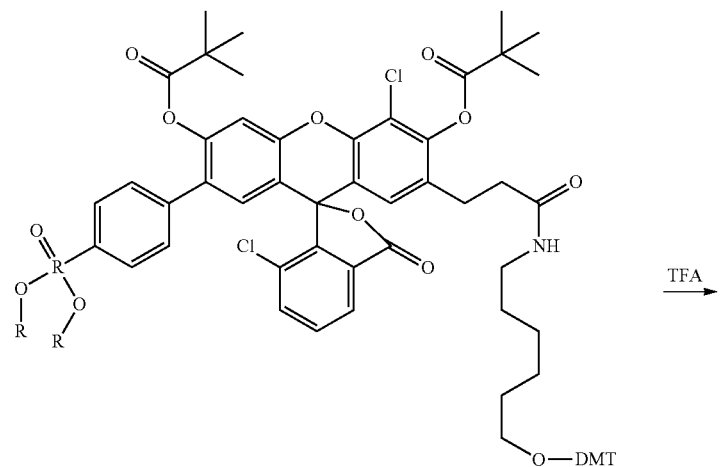

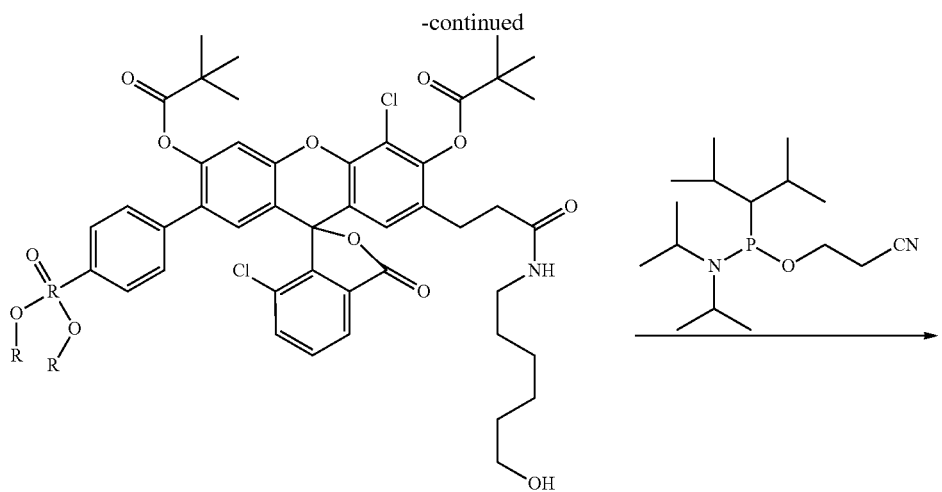

38

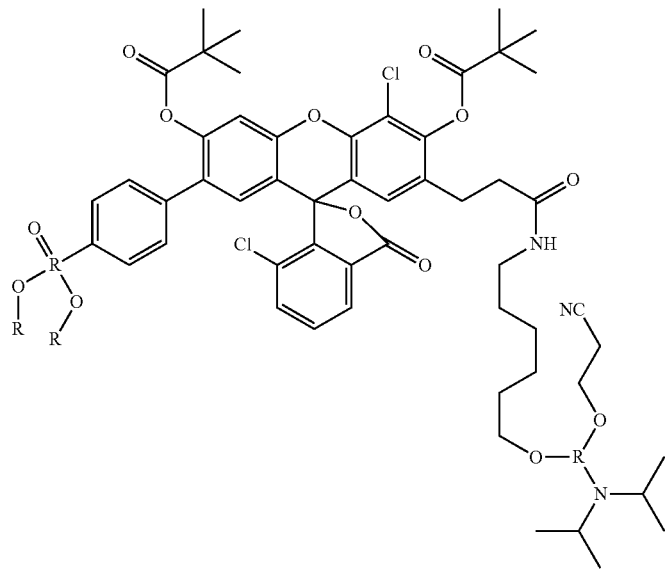

39

Reaction Scheme 6 illustrates the synthesis of phosphoramidite (39). The reaction of 3-chlorophthalic anhydride and methyl 3-(3-chloro-2,4-dihydroxyphenyl)propionate in the presence of $AlCl_3$ to form the benzophenone analog, which on crystallization yielded the pure 6-chloroisomer (32). This isomer was reacted with 31 to yield the 7'-(4-iodophenyl) substituted fluorescein analog (33) which was treated with trimethyl acetic anhydride and N-methylimidazole to give the lactone (34). The lactone was then reacted with O-dimethoxytrityl-6-aminohexanol to form the DMT-intermediate (35) which was then reacted with trimethylacetic anhydride to yield the fully protected analog (36). This analog was reacted with the phosphite reagent (3) to yield the phosphonate ester (37). Removal of the DMT-protecting group with TFA treatment yielded the alcohol (38) which on treatment with 2-cyanoethyl N,N,N',N'-tetraisopropylphosphordiamidite resulted in the desired phosphoramidite (39).

Synthesis of a useful unsymmetric phosphite reagent 41 is shown in React Scheme 7. Reagent 41 allows introduction of reactive linking groups such as phosphoramidite through the phosphonate moiety.

Reaction Scheme 7

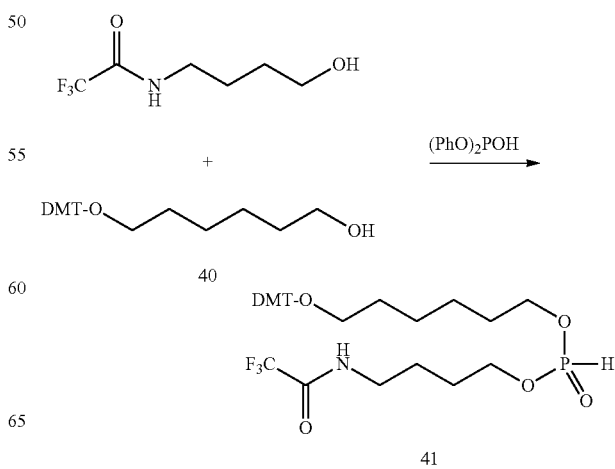

In an example, phosphite 41 was used for the preparation of a fluorescein phosphoramidite (16) as shown in Reaction Scheme 8.
Reaction Scheme 8
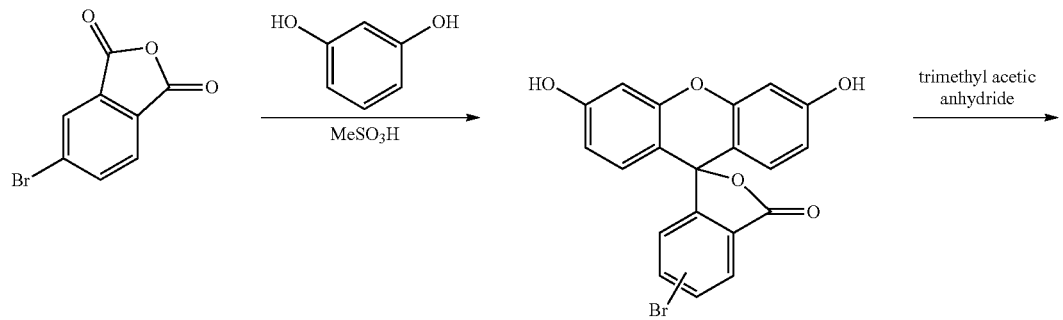
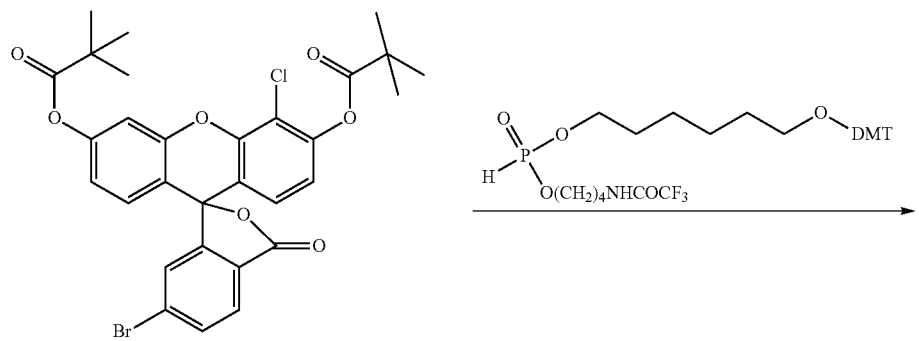
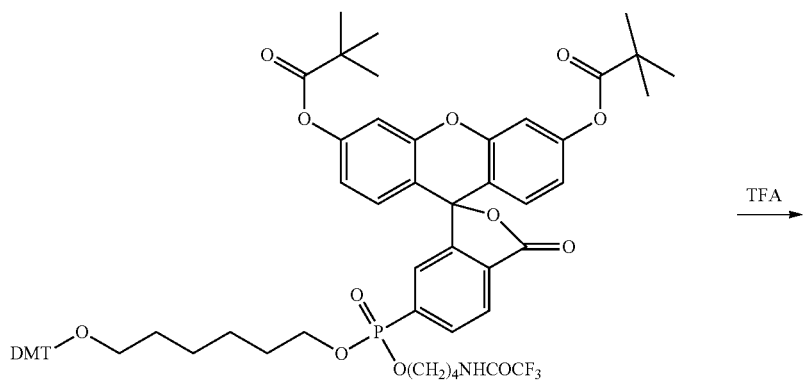

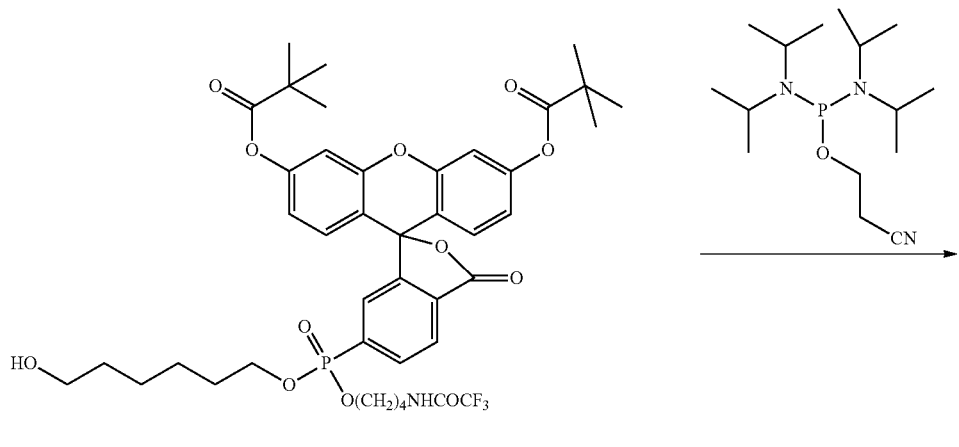

45

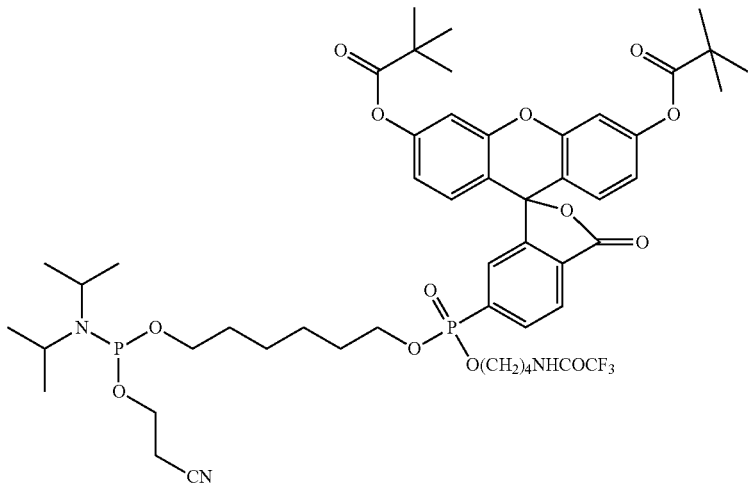

46

Reaction Scheme 8 illustrates the synthesis of phosphoramidite (46). The reaction of 4-bromophthalic anhydride and resorcinol in the presence of methanesulfonic acid yielded a mixture of 5- and 6-isomers of bromofluorescein (42) which was treated with trimethylacetic anhydride and N-methylimidazole to give after silica gel chromatography, the pure 6-isomer of the blocked diester (43). Intermediate (42) was reacted with intermediate 41 to yield the phosphonate (44) which was then treated trifluoroacetic acid to yield the alcohol (45). The alcohol on treatment with 2-cyanoethyl N,N,N',N'-tetraisopropylphosphordiamidite resulted in the desired phosphoramidite (46)

Synthesis of Phosphonate Cyanine Dye Reagents

Reaction Scheme 9 illustrates the synthesis of a phosphonate cyanine phosphoramidite (53).

Reaction Scheme 9
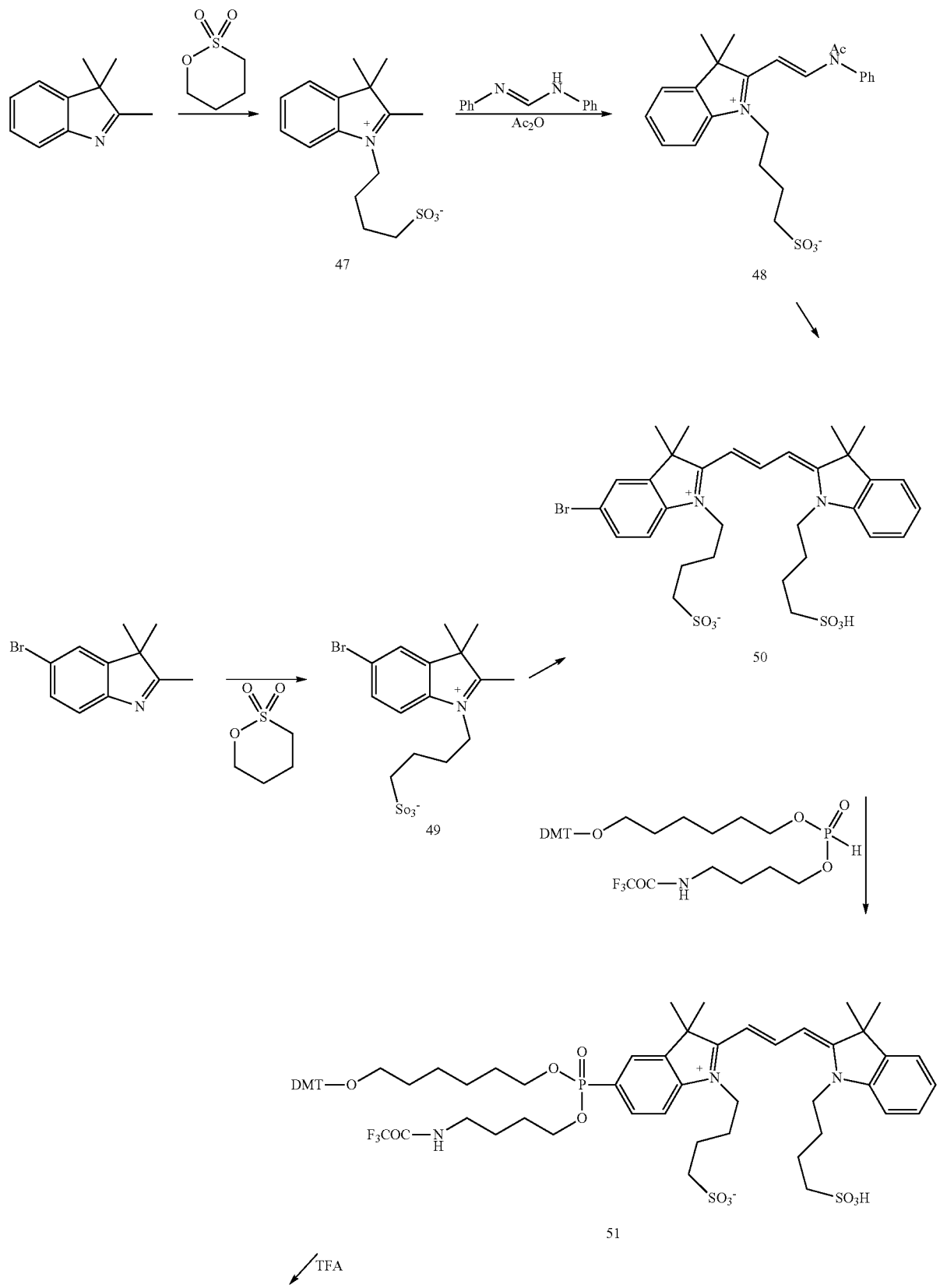

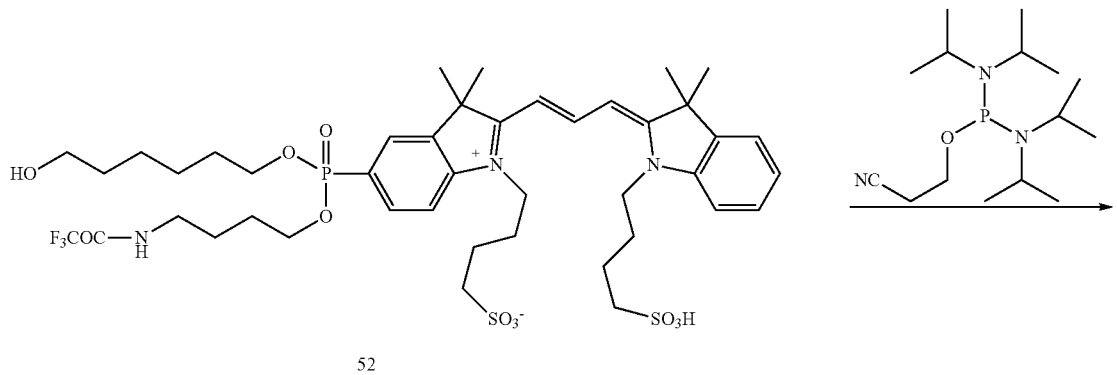

52

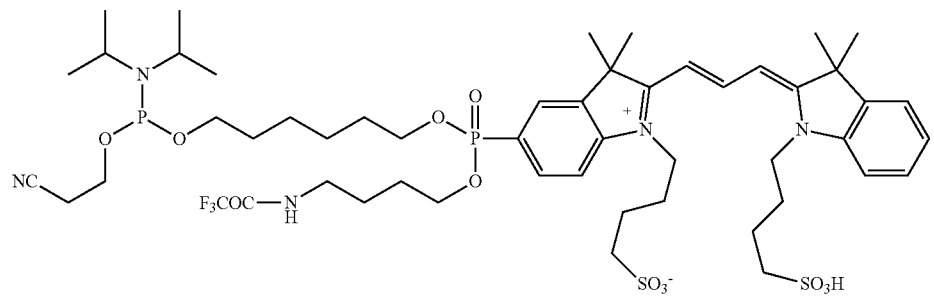

53

The reaction of 2,3,3-trimethylindolenine and 1,4-butane sultone (5.4 g, 40 mmol) yielded the desired indolinum salt (47) which reacted with N,N'-diphenylformamidine to afford formamidine (48). Reaction of 48 with 1-(sulfobutyl)-2,3,3-trimethyl-5-bromoindolinum, inner salt (49) (see, *J. Heterocycle Chem.*, 39:263-269 (2002)) afforded the cyanine intermediate (50). Intermediate (50) was reacted with the phosphite 41 to yield the phosphonate (51) which was then treated with trifluoroacetic acid to yield the alcohol (52). The alcohol on treatment with 2-cyanoethyl N,N, diisopropyl-chlorophosphoramidite resulted in the desired phosphoramidite (53).

Reaction Scheme 10 shows the preparation of a solid support-bound dye reagent of the present invention.

Reaction Scheme 10

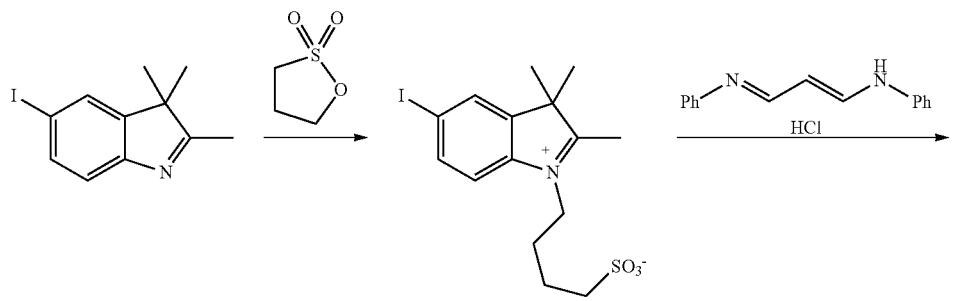

54

-continued
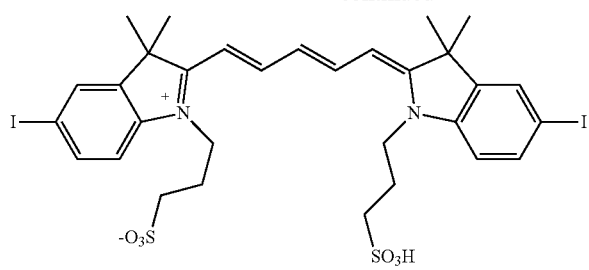
55
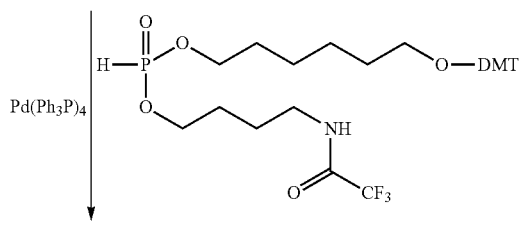
Pd(Ph₃P)₄
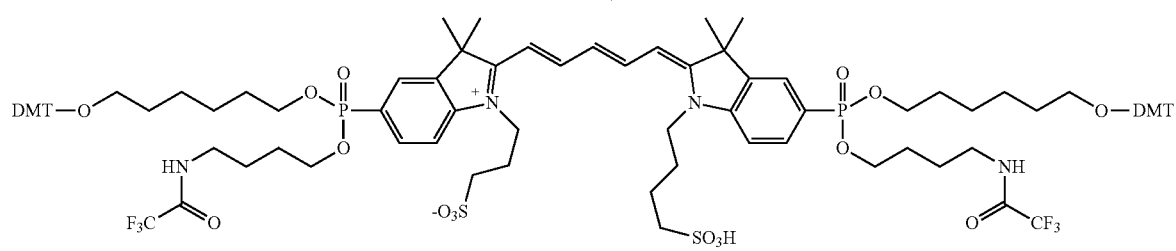
56
TFA
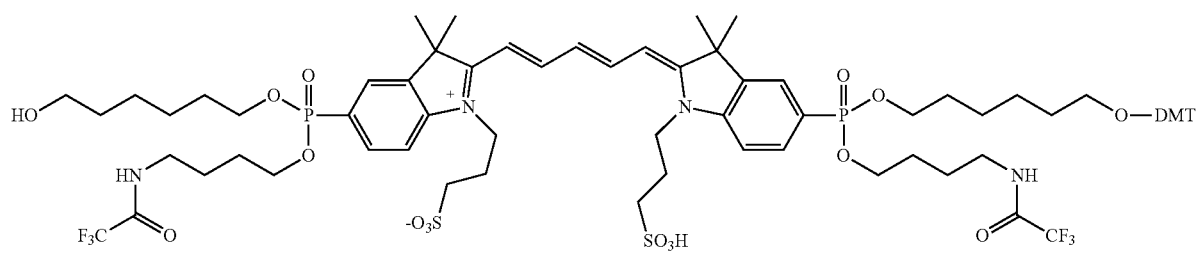
57
1. succinic anhydride
2. PFP-TFA
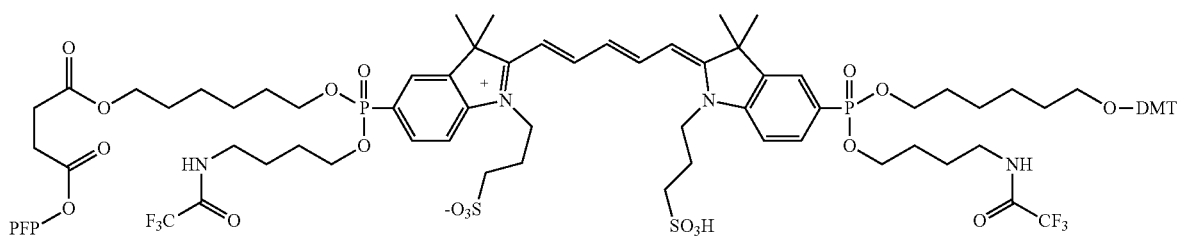
58
CPG-NH2

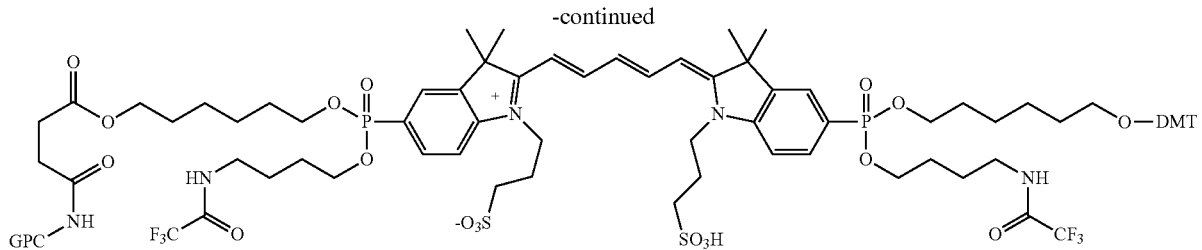

59

Reaction Scheme 10 illustrates the synthesis of the cyanine solid support (59). The reaction of 5-iodo-2,3,3-trimethyl-3H-indole with 1,3-propanesultone provided the desired indolinum salt (54), which reacted with N,N'-diphenylformamidine to afford cyanine intermediate (55). Intermediate (55) was reacted with the phosphite 41 to yield the dimethoxytrityl-phosphonate (56) which was then treated with trifluoro- acetic acid to yield the monomethoxytritylphosphonate intermediate (57). Intermediate 57 was first reacted with succinic anhydride and then with PFP-TFA to yield the PFP-active ester (58). The PFP ester was then reacted with $NH_2$-CPG to give the desired solid support (59).

Reaction Scheme 11 shows the preparation of an activated ester-phosphonate cyanine dye reagent of the present invention.

Reaction Scheme 11

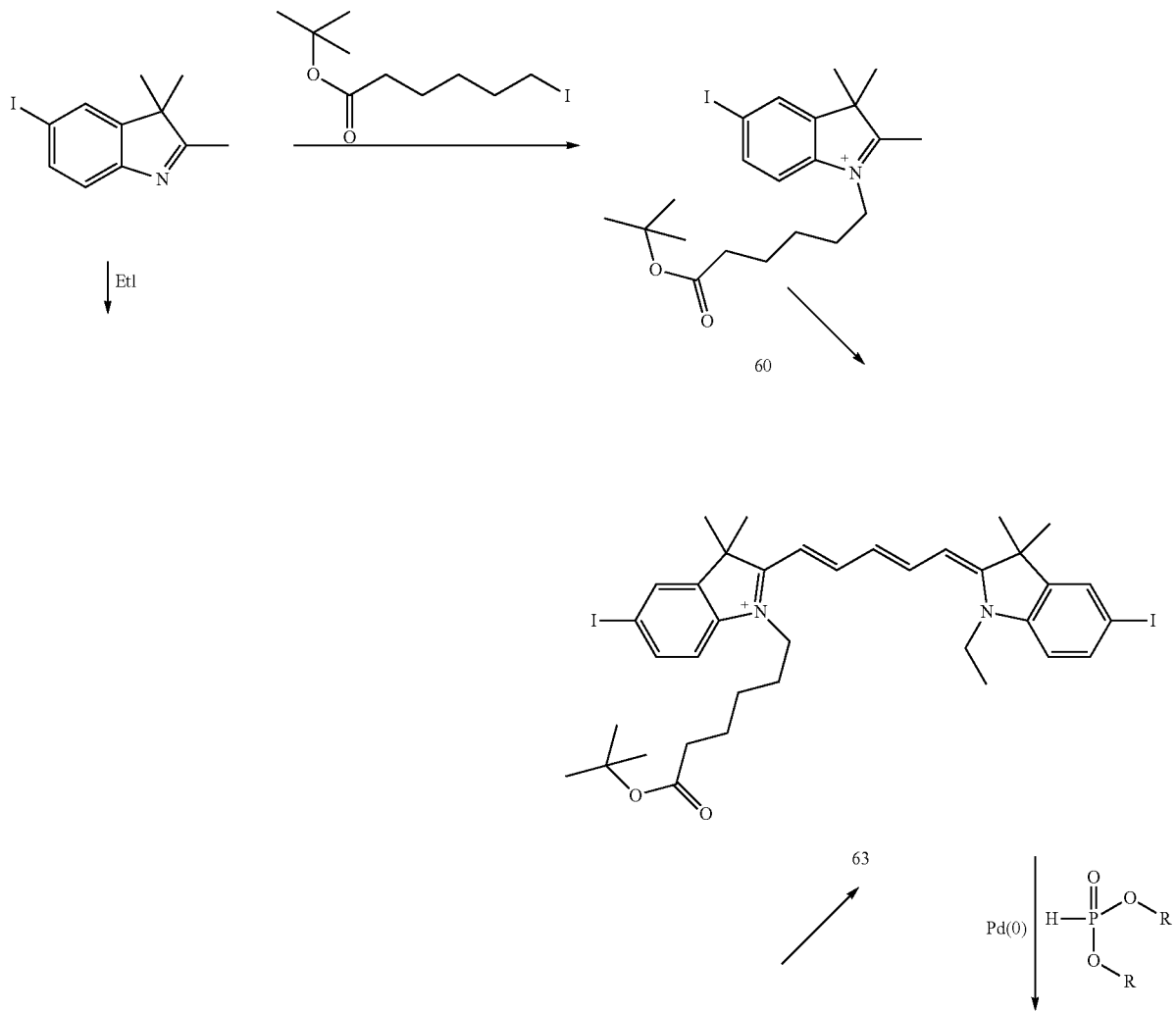

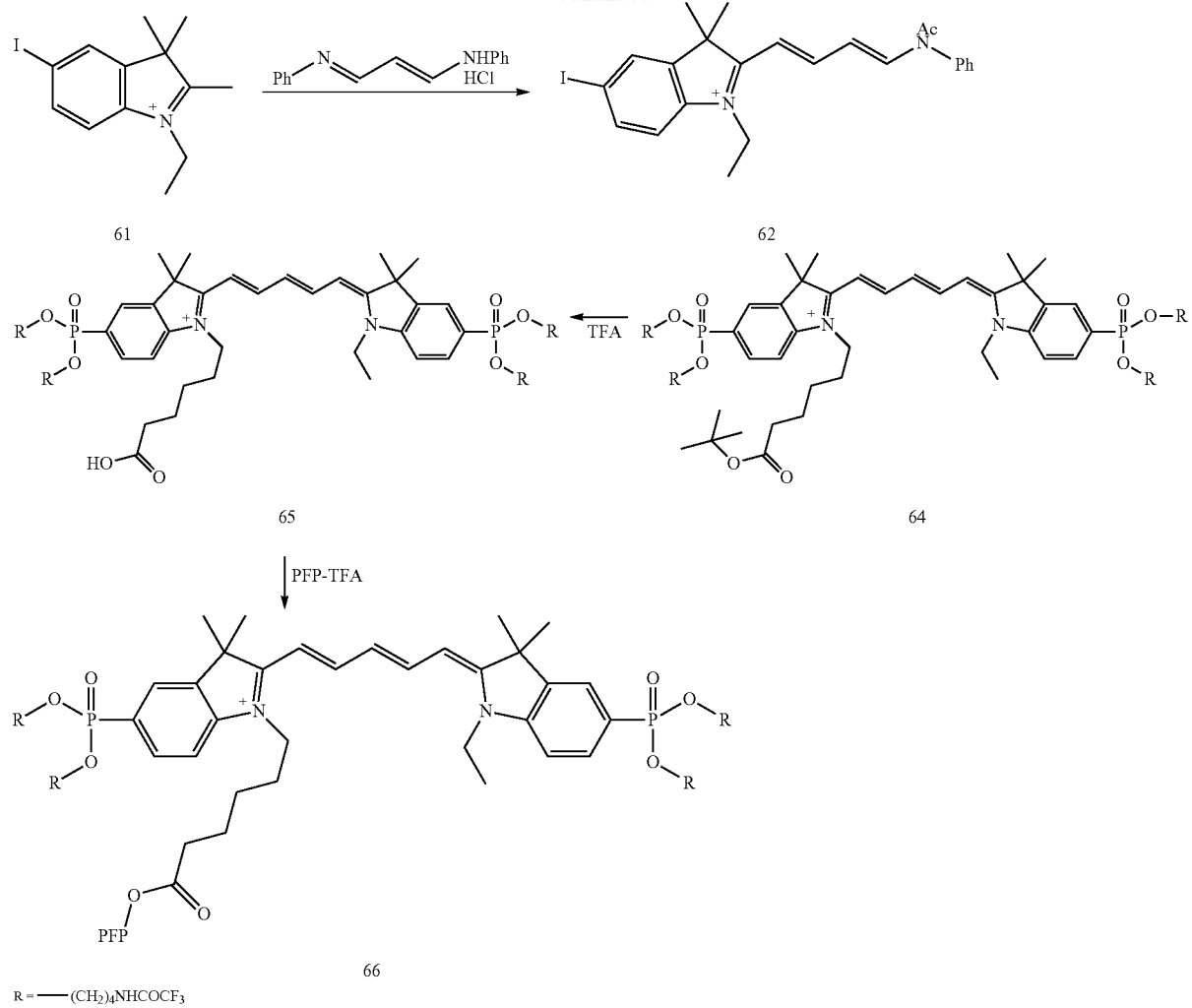

In Reaction Scheme 11, 5-iodo-2,3,3-trimethyl-3H-indolenine was reacted with either tert-butyl 6-iodohexanoate or with ethyl iodide to give indolinum salts 60 and 61, respectively. Compound 61 was then converted to intermediate 62 by reaction with malonaldehyde bis(phenylamino)monohydrochloride in the presence of acetyl chloride and acetic anhydride. Condensation of 61 and 62 resulted in the 63 which was then phosphonylated by reaction with phosphite 3 in the presence of tetrakis(triphenylphosphine)palladium and N-ethylmorpholine to give phosphonate dye 64. To remove the protective, tert-butyl group, compound 64 was treated with trifluoroacetic acid. The resultant acid 65 was then converted into PFP ester 66 by reaction with pentafluorophenyl trifluoracetate.

TABLE 3

Preferred Cyanine Phosphoramidites

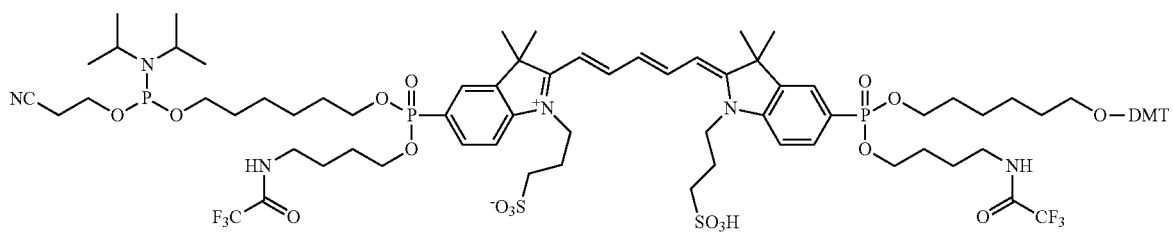

TABLE 3-continued
Preferred Cyanine Phosphoramidites
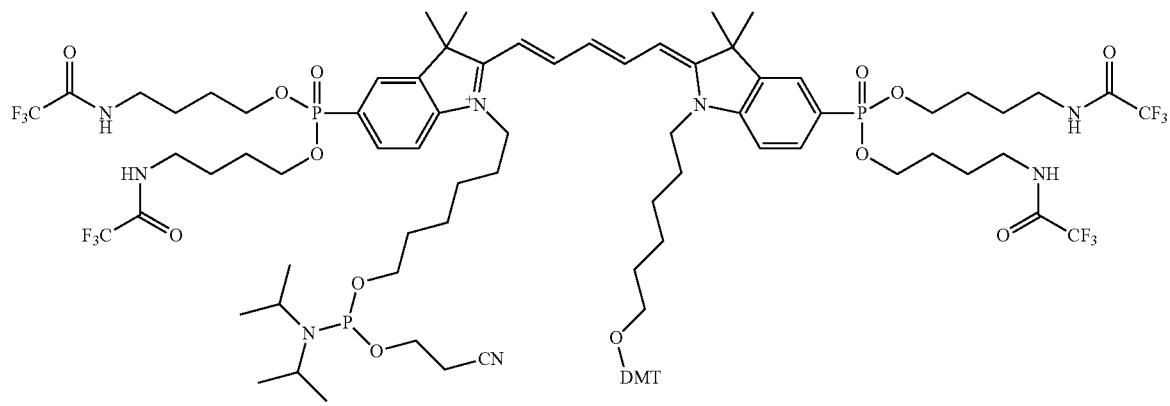
68
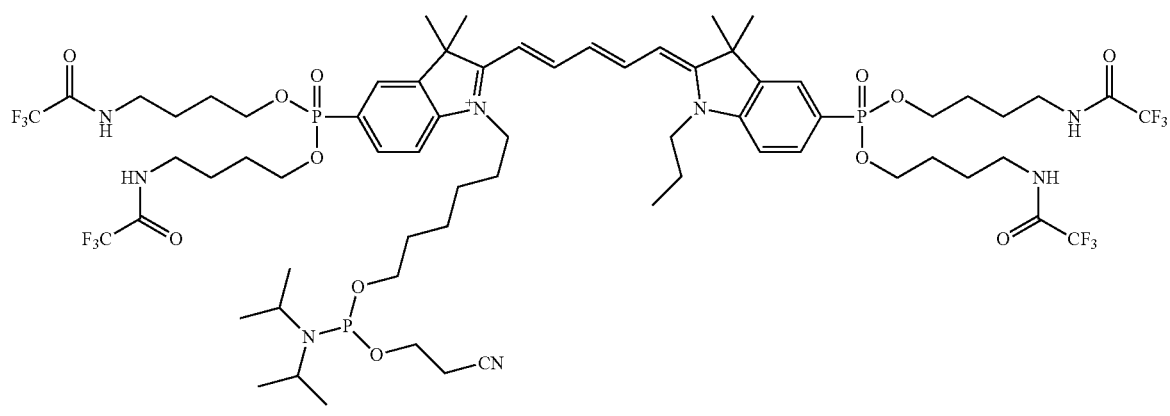
69
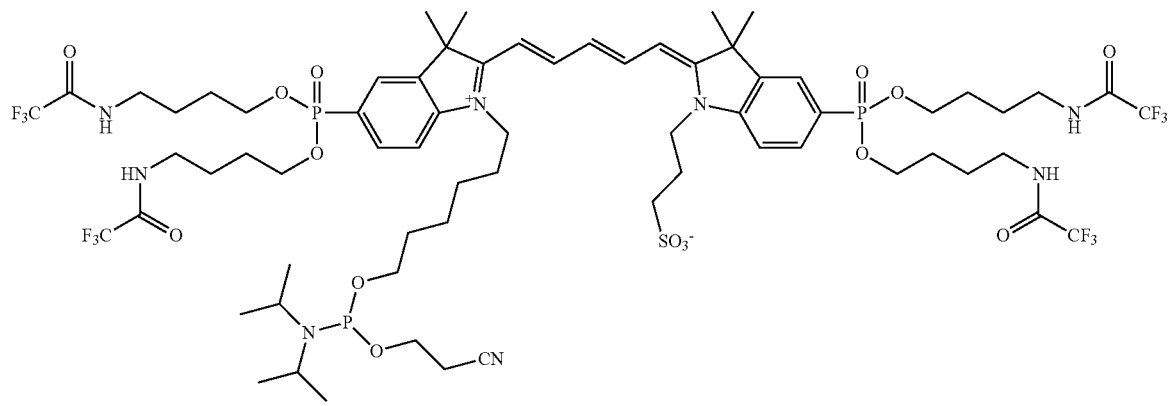
70

Reaction Scheme 13 illustrates the deprotection of the protected phosphonate dyes in a synthesized oligonucleotide.

Reaction Scheme 13

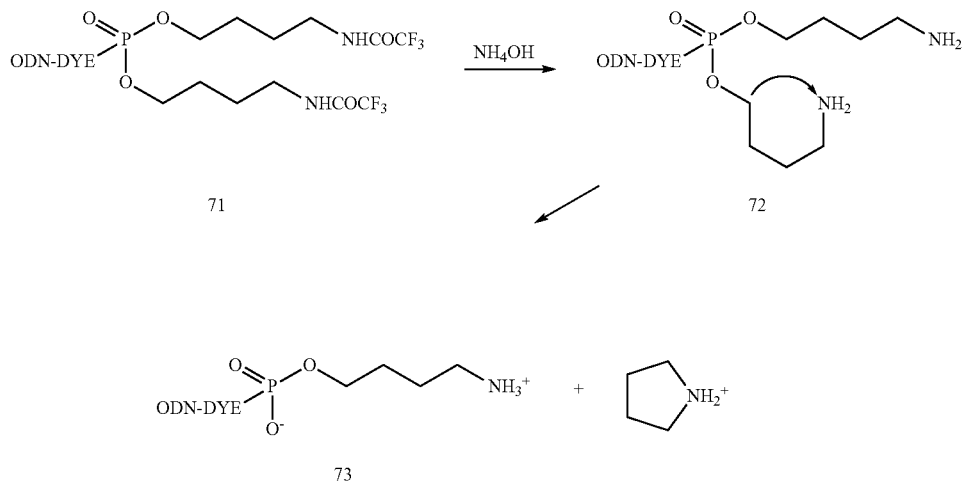

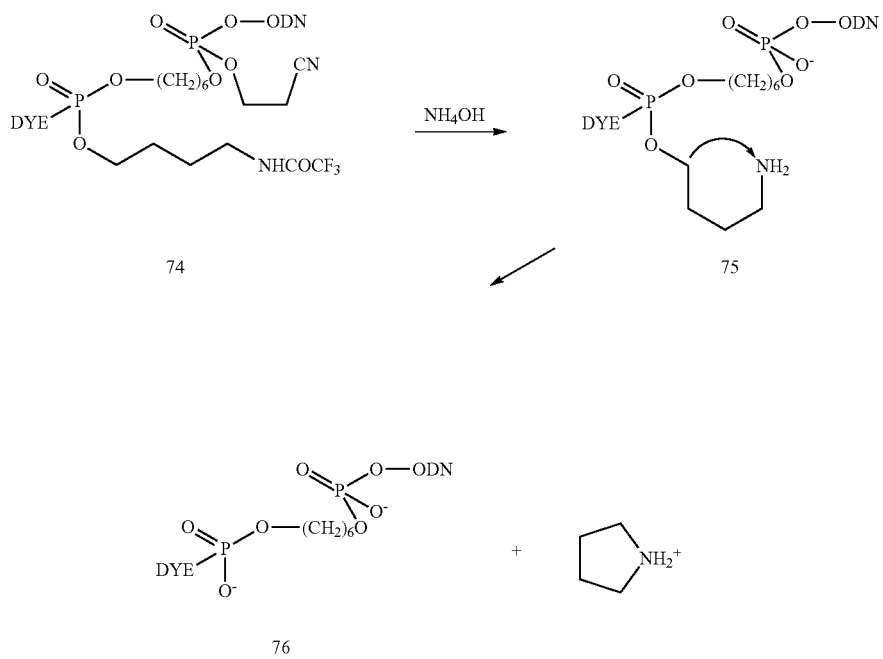

The protected oligonucleotide-dye-phosphonate conjugate (71 and 74) can be synthesized with any of the phosphoramidites of the invention. Ammonium hydroxide deprotection yields the oligonucleotide-zwitterionic phosphonate-dye conjugates (73 and 76). The structures of conjugates 73 and 76 were confirmed by mass spectrometry. Structures 72 and 74 are postulated intermediates with a suggested mechanism for hydrolysis.

The novel bis(4-(2,2,2-trifluoroacetamido)butyl)phosphite (3) reagent can be used in the synthesis of other dyes of the present invention.

In the sections below, Schemes are provided for exemplary syntheses of various dyes. One of skill in the art will appreciate that the invention is not limited to these methods. In addition, those skilled in the art will appreciate that the proposed reaction schemes may have to be modified to achieve the desired products in Reaction Schemes 14 to 19.

Reaction Scheme 14
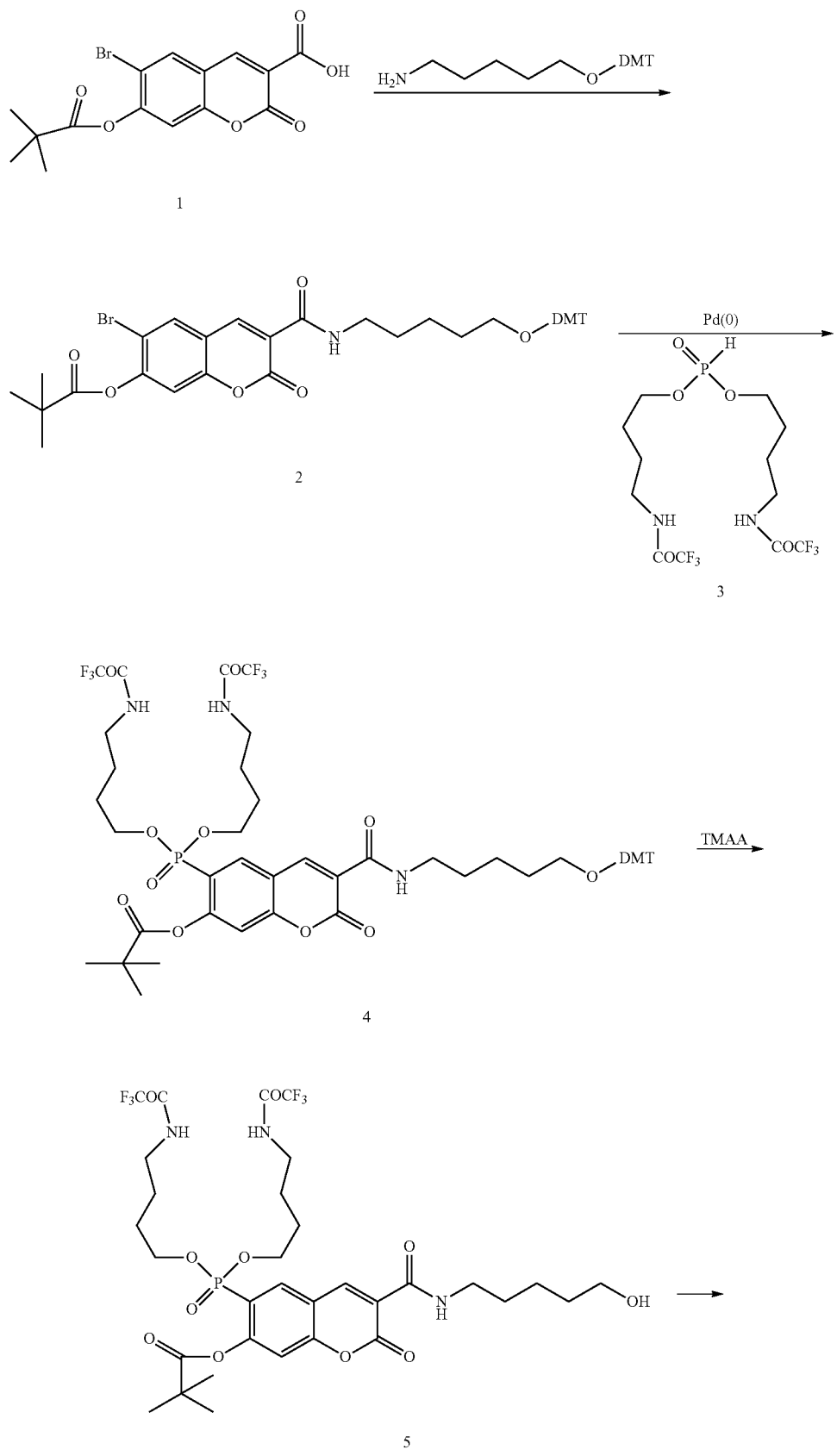

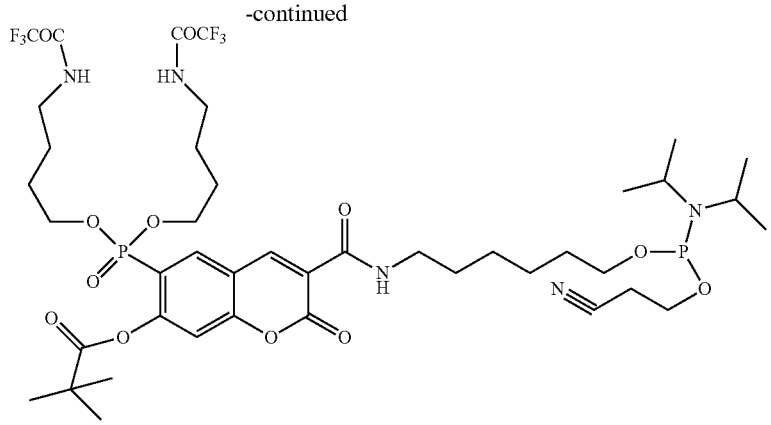

6

6-Substituted phosphonate coumarin dyes can be synthesized starting from the protected 6-bromo-7-hydroxy-2-oxo-2H-chromene-3-carboxylic acid (1) ((for synthesis see Baker, et al., *Chem. Soc.* 170-173 (1970)) as shown in Reaction Scheme 14. Compound (1) is reacted with 5-(bis(4-methoxyphenyl)(phenyl)methoxy)pentan-1-amine to yield DMT-amide analog 2. Reaction of (2) with bis(4-(2,2,2-trifluoroacetamido)butyl) phosphite (3) provides the protected phosphonate dye (4). In the next step the dimethoxytrityl protecting group is removed to yield the alcohol (5) which can be converted to the protected phosphoramidite (6).

The synthesis of 8-substituted halogen coumarin analogs was disclosed in WO03023357. The 8-bromocoumarin lactone (7) can be converted in a similar fashion described in Reaction Scheme 14 to yield the equivalent phosphoramidite (8) shown in Reaction Scheme 14a.

Reaction Scheme 14a

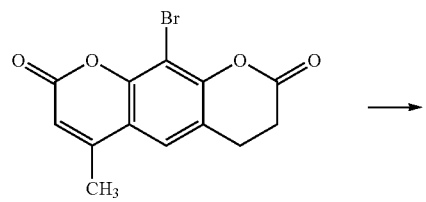

7

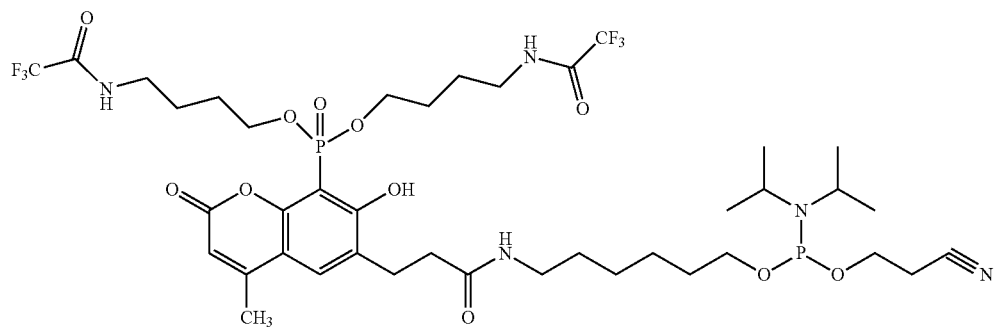

8

Reaction Scheme 15
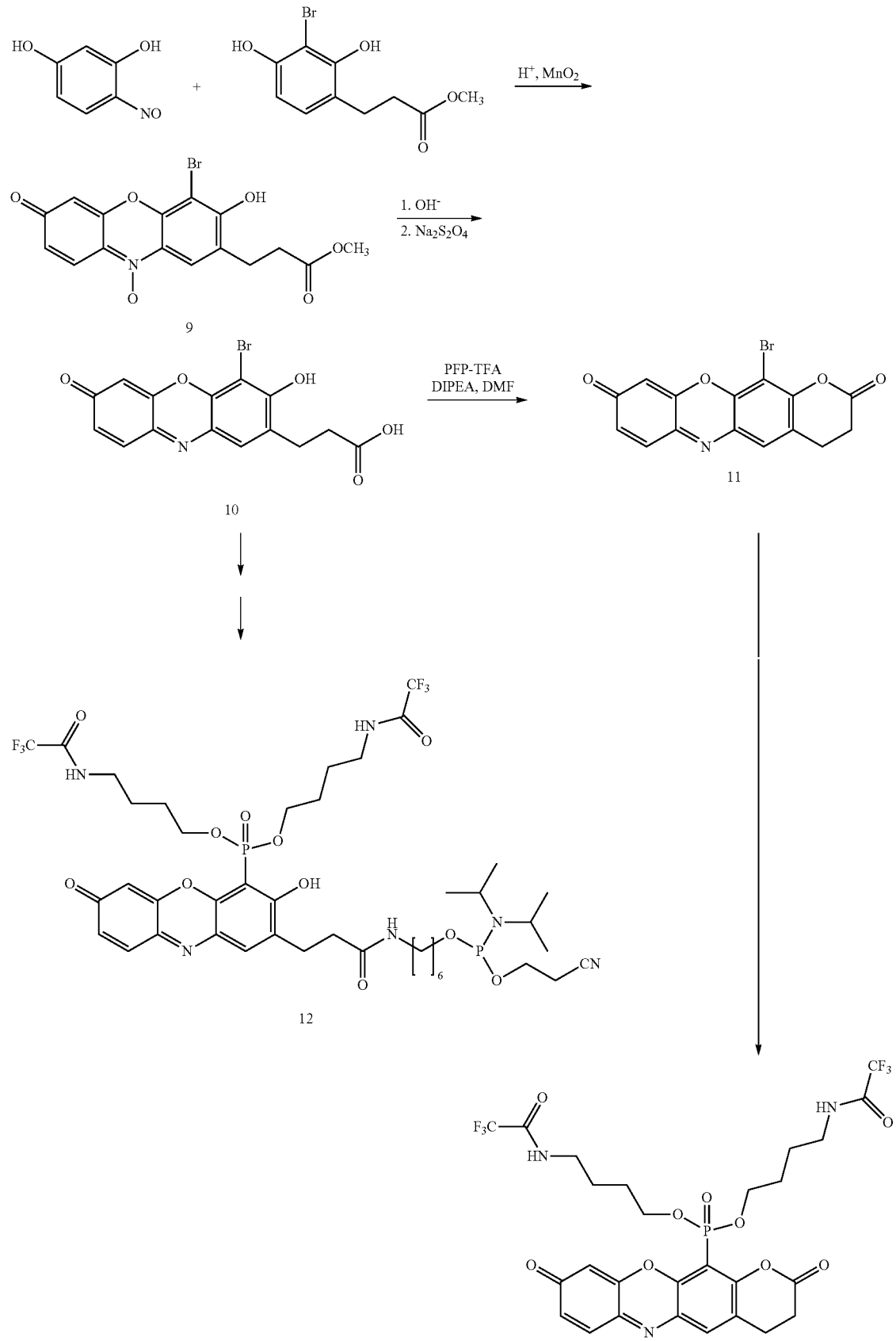

The synthesis of halogenated resorufin lactones (9) was disclosed in WO 03/023357. Briefly the reaction of nitrosobenzene-1,3-diol and methyl 3-(3-bromo-2,4-dihydroxyphenyl)propanoate in the presence of acidic $MnO_2$ yields the resorufin-N-oxide (9) which can be reduced to the bromoresorufinpropionic acid (10) (Reaction Scheme 15). This compound was lactonized (11) and can be converted to the phosphonate lactone analog 12 similarly as described in Reaction Scheme 15. The bromoacid (10) can also be converted to the phosphonate resorufin phosphoramidite 13.

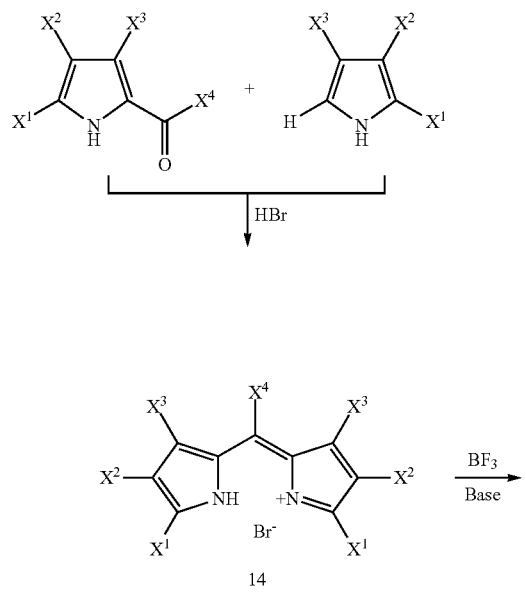

Reaction Scheme 16

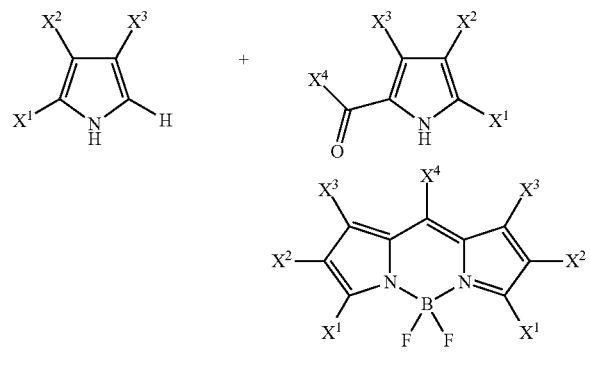

The dipyrrometheneboron difluoride parent heterocyclic compounds with a reactive group for attachment to biological materials were first disclosed in U.S. Pat. No. 4,774,339. Dipyrrometheneboron difluoride products were reported to be modifiable in a subsequent reaction by chemical techniques known to one skilled in the art including but not limited to sulfonation, nitration, alkylation, acylation, and halogenation. It was further reported that the substituents can in some cases be further modified to introduce chemically reactive functional groups. Briefly these substituted dipyrrometheneboron difluorides are prepared as shown in Reaction Scheme 16, A substituted pyrrole-5-carboxaldehyde was reacted with a substituted pyrrole in the presence of hydrobromic acid to yield the substituted dipyrromethene intermediate (14) which was converted to substituted dipyrrometheneboron difluoride dye (15). The symbols $X^1$, $X^2$, $X^3$, and $X^4$ have the same definition as described previously for this class of dyes.

Reaction Scheme 17

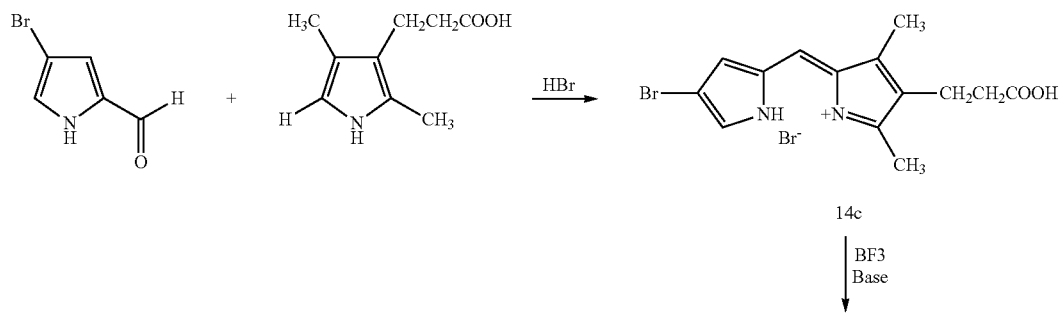

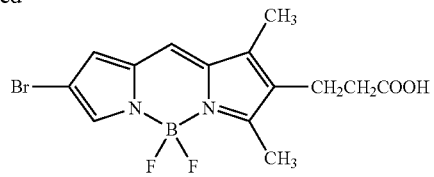

15c

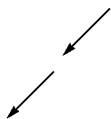

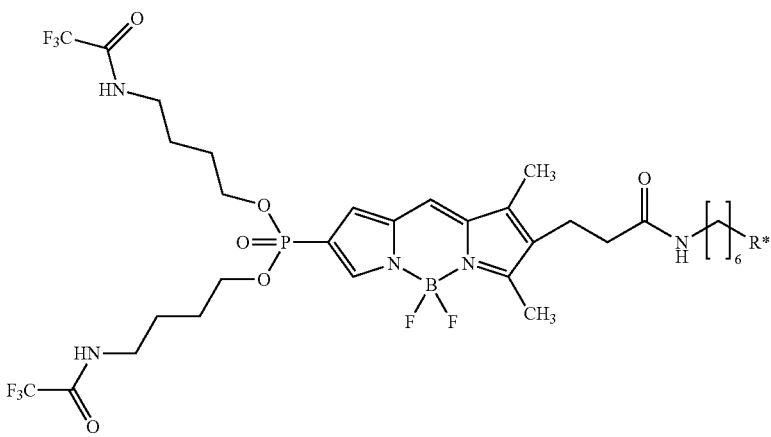

16

Dipyrometheneboron difluoride phosphonate dyes of interest can be synthesized as shown in Reaction Scheme 17. The reaction starting from 4-bromopyrrole-2-carboxaldehyde and 3-(2,4-dimethyl-1H-pyrrol-3-yl)propanoic acid yields the bromo-intermediate 14, which with $BF_3$ base yields the bromodipyrrometheneboron difluoride 15. Dye 15 can further be converted via a phosphonate intermediate to the phosphonate dipyrometheneboron difluoride intermediate (16) where R* can be a solid support or a phosphoramidite.

In another embodiment carboxylic group in intermediate 15c can be converted in to a reactive moiety such as a pentafluorophenyl- or a succinimidyl esters, Pyrrole-2-carboxaldehydes needed for the synthesis of pyrrolomethenes are either commercially available or readily prepared from the corresponding pyrroles by the Vilsmeyer Haak formylation (R. M. Silverstein, E. E. Ryskiewicz and C. Willard. ORG. SYNTH. COLL VOL IV, page 831).

Appropriately substituted pyrrole derivatives (Reaction Scheme 17) are either commercially available or may be synthesized by methods known in the ad, for example as described (R. Elderfield, HETEROCYCLIC COMPOUNDS, vol. 1, ch. 6, THE CHEMISTRY OF PYRROLE AND ITS DERIVATIVES, by Corwin (1950); Silverstein, Ryskiewicz and Willard. ORG. SYNTH. COLL VOL IV, page 831 and Korostova et al., Russ. J. Org. Chem. 34, 1691 (1998)). Pyrrole fatty acids are most conveniently prepared by the Wittig reaction (see, Wittig & Schollkopf, Ber, 87: 1318 (1954)) of pyrrole aldehydes with carboxy or protected-carboxy terminated phosphonium or phosphonate derivatives.

Ruthenium Complexed Phosphonate Dyes

The synthesis of mixed ligand ruthenium (II) complexed phosphoramidite dyes have previously been reported starting from commercially available cis-Bis(2,2'-bipyridyl)ruthenium(II) chloride dehydrate (Khan et al, Inorg. Chem. 38:3922-3925 (1999)). Starting with cis-Bis(2,2'-bipyridyl) ruthenium(II) chloride dehydrate (16) and (2,2'-bipyridine)-5-carboxylic aid, 5'-bromo-methyl ester (17; Haino et al, Chem. comm., 402-403 (2002)). The Khan et al procedure allows the synthesis of a ruthenium bipyrydyl phosphoramidite (19) as shown in Reaction Scheme 18.

Reaction Scheme 18
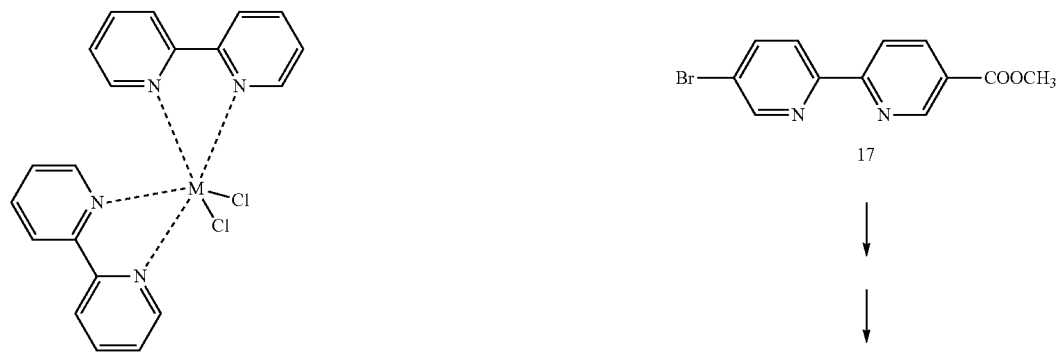
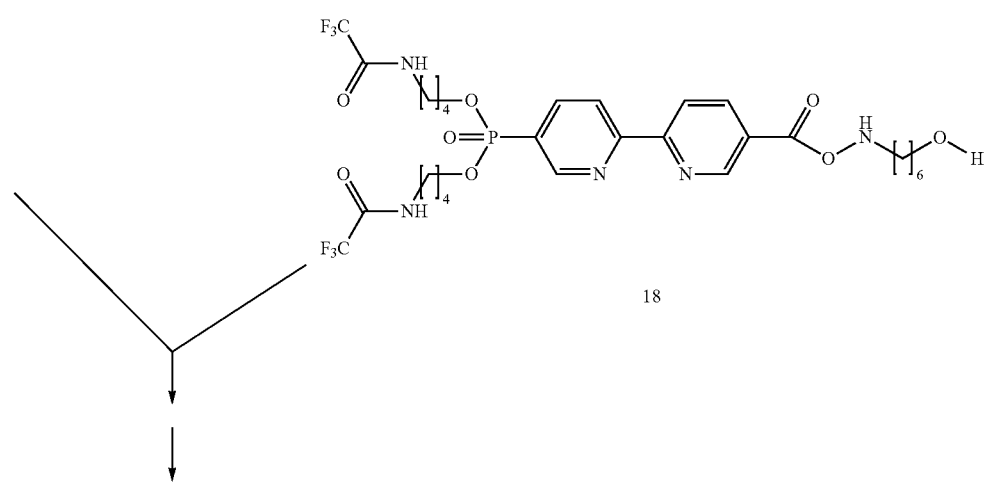
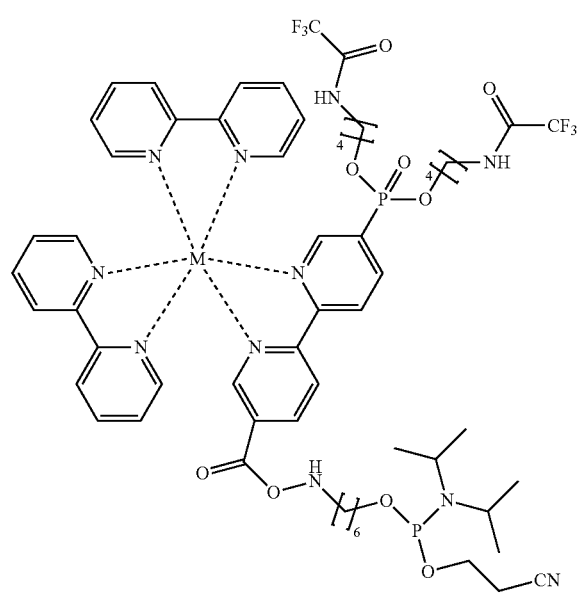

Briefly the standard procedure converts the methyl ester 17 to the blocked phosphonate bipyridyl alcohol (18), which reaction with 19 followed by the introduction of the phosphoramidite as taught by Khan et al, can provide phosphonate bipyridyl ruthenium phosphoramidite 19.

In another embodiment carboxylic group in compound 19 can be converted in to a reactive moiety such as a pentafluorophenyl- or a succinimidyl esters instead of the phosphoramidite group.

Polymethine-Based Phosphonate Dyes

The phosphonate polymethine-based dyes can be synthesized by the basic method disclosed in US 2004/0260093. The approach is briefly outlined in Reaction Scheme 19.

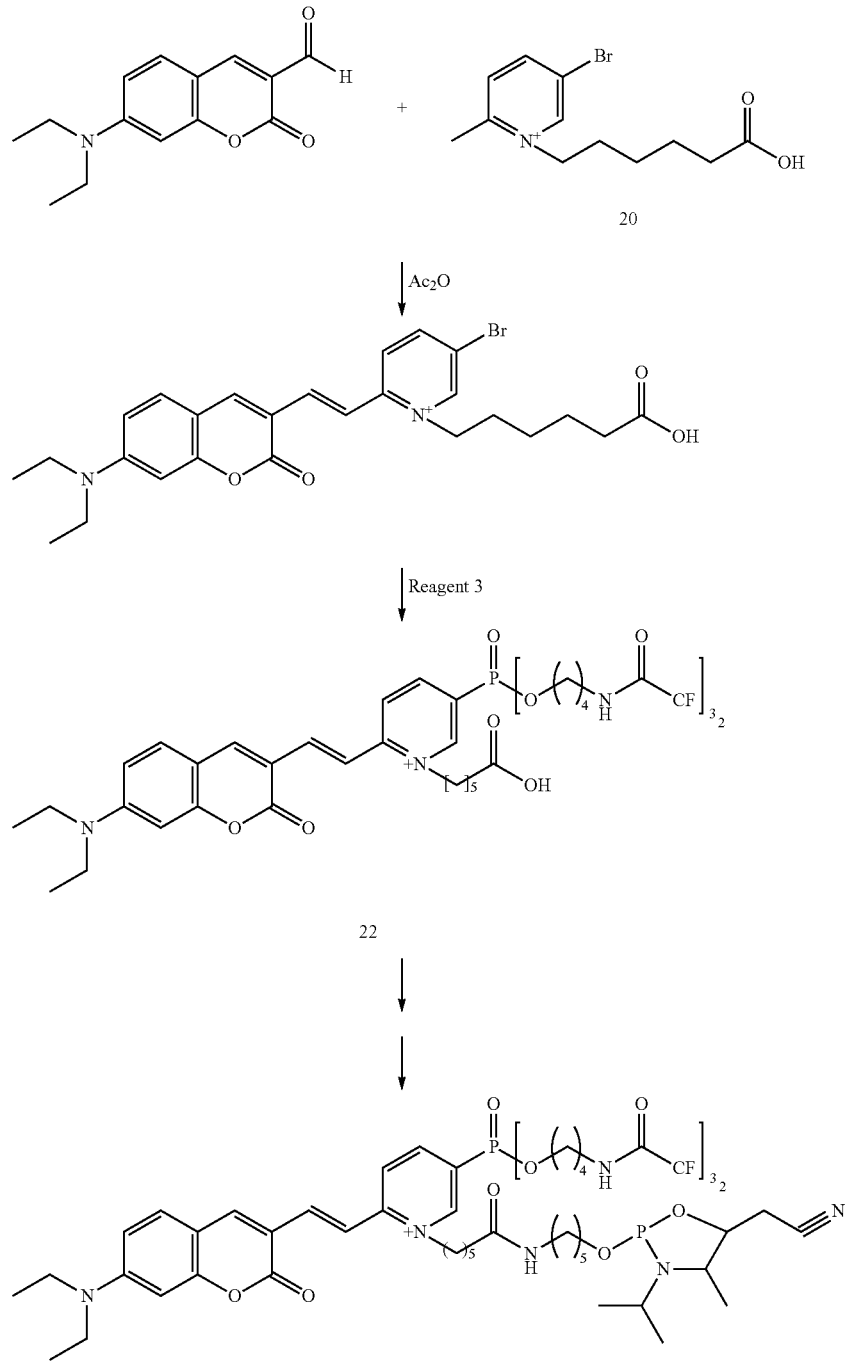

Reaction Scheme 19

The reaction of 7-(diethylamino)-2-oxo-2H-chromene-3-carbaldehyde with an active —CH compound 20 in the presence of Ac$_2$O provides a bromo-intermediate (21) which on reaction with phosphate reagent 3 provides blocked phosphonate intermediate (22). This intermediate can be converted to the phosphoramidite reagent (23) in the usual fashion.

In a related embodiment carboxylic group in intermediate 23 can be converted to a reactive moiety such as a pentafluorophenyl- or a succinimidyl esters instead of the phosphoramidite group.

In yet another embodiment starting with a halogen substituted 2-oxo-2H-chromene-3-carbaldehyde, the halogen can be substituted with the phosphonate group in any one of the sp$^2$-hybridized carbon positions.

Oligonucleotide Probes and Other Labeled Biological Agents

In another aspect, the present invention provides oligonucleotide probes and other biological agents in which one or more of the fluorescent dyes above have been attached to a nucleic acid, polynucleotide, oligonucleotide and the like. As noted above, the present invention finds broad application in labeling of nucleic acids (including nucleotides, nucleosides, DNA, RNA, PNA, locked nucleic acids, oligonucleotides and the like), peptides or proteins, oligosaccharides, glycosylated proteins, and other biological agents. Additionally, the nucleic acids can include modified bases (e.g., 5-substituted pyrimidines, 3-substituted purines, substituted deazapurines, substituted pyrazolo[3,4-d]pyrimidines, and the like). See, for example, co-pending application Ser. Nos. 09/724,988 and 09/447,936. The invention also finds utility in labeling of oligonucleotides and modified oligonucleotides having attached groups such as minor groove binders, quenching agents or quenchers, interpolators, crosslinking groups, and the like.

In one embodiment of the invention, the phosphonate dyes contain at least one group -L-R$^X$ where R$^X$ is the reactive group that is attached to the fluorophore by a covalent linkage L. In certain embodiments, the covalent linkage attaching the phosphonate dye to R$^X$ contains multiple intervening atoms that serve as a spacer. The dyes with a reactive R$^X$ group fluorescently label a wide variety of organic or inorganic substances that contain or are modified to contain functional groups with suitable reactivity, resulting in chemical attachment of the conjugated substance (R$^Y$), represented by -L-R$^Y$. The reactive group and functional group are typically an electrophile and a nucleophile that can generate a covalent linkage. Typically, the conjugation reaction between the reactive dye and the substance to be conjugated results in one or more atoms of the reactive group R$^X$ to be incorporated into a new linkage L attaching the phosphonate dye to the conjugated substance R$^Y$.

Selected examples of functional groups involved to form linkages where the reaction of an electrophilic group and a nucleophilic group yields a covalent linkage are shown below.

Examples of nucleophilic groups include —NH$_2$, —NHNH$_2$, —ONH$_2$, —NHC═(O)NHNH$_2$, —OH, —COOH, or —SH. The electrophilic groups are activated esters, acrylamides, acyl azides, acyl halides, aldehyde or ketones, alkyl halides, alkyl sulfonates, anhydrides, aryl halides, aziridines, boranates, carboxylic acids, carbodiimides, diazoalkanes, epoxides, haloacetamides, halotriazines, imidoesters, isocyanates, isothiocyanates, maleimides, phosphoramidites, silyl halides, sulfonate ester and sulfonyl halides. Additionally, a spacer can include hetero atoms in linear or acyclic portions, cyclic portions, aromatic rings or combinations thereof.

Conjugated substances include nucleic acids, oligonucleotides, oligonucleotide conjugates, proteins, peptides, drugs, immunoglobulins, receptors, toxins, organic small molecule ligands, enzyme substrates, vitamins, carbohydrates, biotin, streptavidin, solid substrate, and a solid support for oligonucleotide synthesis) described and used herein.

In one embodiment, conjugates of biological polymers such as peptides, proteins, oligonucleotides, nucleic acid polymers are also labeled with, a second fluorescent or non-fluorescent dye, including an additional dye of the present invention, to form an energy-transfer pair.

In yet another embodiment, conjugates of biological polymers such as peptides, proteins, oligonucleotides, nucleic acid polymers are also labeled with a second fluorescent or non-fluorescent dye, in addition to the dye of the present invention, to form an energy-transfer pair where the fluorescence of the latter is quenched. Binding of these conjugated to their natural receptor or complement result in conformational change or cleavage of bond with an increase in fluorescence. Preferred selected examples of dual labeled oligonucleotide probes are 5'-(MB)$_n$$^y$-Fl$^A$-oligonucleotide-Fl$^B$-3',5'-Fl$^A$-oligonucleotide-Fl$^B$-MB-3' where Fl$^A$ and Fl$^B$ are either a fluorophore or a quencher with the proviso that a probe can contain only one quencher and one fluorophore, MB is a minor groove binder and n$^y$ is 0 or 1. In one embodiment the quencher is non-fluorescent.

In a related embodiment the preferred conjugate probes are used in amplification methods to detect nucleic acid targets, nucleic acid polymorphisms and gene expression analysis. These methods are disclosed in U.S. Pat. No. 6,312,894, WO 2004/018626, Livak, K J a Schmittgen, T D, *Methods* 25: 402-408 (2001).)

Examples of minor groove binders are disclosed U.S. Pat. No. 5,801,155 and quenchers in U.S. Pat. No. 6,699,975 and WO02099141 all which are included by reference in their entireties.

In another embodiment, the conjugated substance is a nucleic acid base, nucleoside, nucleotide or a nucleic acid polymer, including those that were modified to possess an additional linker or spacer for attachment of the dyes of the invention, such as an alkynyl linkage (U.S. Pat. No. 5,047,519; U.S. RE 38,416), an aminoallyl linkage (U.S. Pat. No. 4,711,955) or other linkage.

In one embodiment a xanthenephosphonate is attached to a solid support through a cleavable linker. The linker molecule also contains a hydroxyl group protected with DMTr (or like) blocking group. After removal of the DMTr group, an oligonucleotide is synthesized on an automated oligonucleotide synthesizer by step-wise attachment of nucleotide units to the hydroxyl group. A quencher is introduced at the 5'-end with the appropriate phosphoramidite, or post-synthetically with a quencher containing a reactive group, to yield an ODN having an attached xanthenephosphonate moiety (XP) and a quencher (Q). A solid support compatible with oligonucleotide synthesis includes controlled pore glass, polystyrene, plastic, nylon, gold and the like.

In one embodiment a xanthenephosphonate (X$^P$) is attached to a solid support through a cleavable linker. The linker molecule also contains a hydroxyl group protected with DMTr (or like) blocking group. After removal of the DMTr group, an oligonucleotide is synthesized on an automated oligonucleotide synthesizer by step-wise attachment of nucleotide units to the hydroxyl group. A X$^P$ fluorophore is introduced at the 3'-end with the appropriate phosphoramidite, or post-synthetically with a X$^P$ fluorophore containing a reactive group, to yield an ODN having an attached X$^P$ moiety, or alternatively a X$^P$ and a quencher (Q) or in addition to the $X^P$ and Q also a MB (MB-Q-ODN-L-Fl). In this connection it is noted that the synthesis of MBs and their attachment to ODNs is well known (see for example U.S. Pat. No. 5,801, 155, Ser. Nos. 09/539,097 and 9/141,764; all of which are expressly incorporated herein by reference).

EXAMPLES

General Experimental

All air and water sensitive reactions were carried out under a slight positive pressure of argon. Anhydrous solvents were obtained from Aldrich (Milwaukee, Wis.). Flash chromatography was performed on 230-400 mesh silica gel. Melting points were determined on a Mel-Temp melting point, apparatus in open capilla$R^Y$ and are uncorrected. Elemental analysis was performed by Quantitative Technologies Inc. (Boundbrook, N.J.). UV-visible absorption spectra were recorded in the 200-400-nm range on a UV-2100 (Shimadzu) or a Lambda 2 (Perkin Elmer) spectrophotometers. $^1$H NMR spectra were run at 20° C. on a Varian 300 spectrophotometer; chemical shifts are reported in ppm downfield from Me$_4$Si. Thin-layer chromatography was run on silica gel 60 F-254 (EM Reagents) aluminum-backed plates.

In the examples below, compound numbering refers to those numbers provided in Reaction Schemes 1-13.

Example 1 bis(4-(2,2,2-trifluoroacetamido)butyl)phosphite (3)

This example demonstrates the synthesis of the novel phosphonylation reagent (3) as shown in Reaction Scheme 1.

A 250 mL flask was charged with magnetic stirring bar, compound 1 (see, *J. Org. Chem.* 62 (20): 6712-6713 (1997)) (9.455 g, 51 mmol), pyridine (100 mL), and diphenylphosphide (2) (7.035 g, 25.5 mmol). The mixture was stirred for 1 h at room temperature, then concentrated on a rotary evaporator, diluted with ethyl acetate (200 mL) and washed with 10% citric acid (2×150 mL). Aqueous phase was re-extracted with ethyl acetate (100 mL) and organic phases were combined, washed with brine (100 mL), dried eve Na$_2$SO$_4$ and concentrated in vacuo. Residue was chromatographed on silica eluting, first, with ethyl acetate to separate phenol and, second, with acetone to elute the desired phosphite 3. Concentration of the pure product fractions gave 8.0 g, (75%) of the phosphite 3 as viscous liquid. $^1$H NMR (dmso-d$_6$): 9.44 (brs, 2H), 6.82 (d, J=695 Hz; 1H), 4.0 (m, 4H), 3.21 (q, J=6.2 Hz; 4H), 1.70-1.50 (m, 8H). $^{31}$P NMR (dmso-d$_6$): 9.02 (d, J=695 Hz), $^{19}$F NMR: 086 (s).

Example 2

This example illustrates the synthesis of a protected 4',4,5, 6,7-pentachloro-7'-phosphonate fluorescein analog (11) as shown in Reaction Scheme 2.
Compound 5

A 0.5 L round bottom flask equipped with magnetic stirring bar was charged with 4-bromoresorcinol (3.62 g, 19.2 mmol), compound (4) (8.264 g, 16.0 mmol, prepared as described in WO 03/023357) and trifluoroacetic acid (50 mL). Methanesulfonic acid (50 mL) was added and resultant mixture was stirred at +80° C. for 3 h. Resultant red solution was cooled and poured onto ice (~400 g). Obtained red solid was collected by filtration on sintered glass funnel, washed with water (3×40 mL) and dissolved in a mixture of water (300 mL) and triethylamine (10 mL). The solution was heated to boiling point with stirring, then cooled and acidified to pH~2 by adding aqueous hydrochloric acid. The resultant fine suspension was extracted with ethyl acetate, washed twice with brine, dried over MgSO$_4$. Concentration afforded crude product 5, which was contaminated with its debrominated analog formed during the condensation reaction. The mixture was separated by silica gel chromatography eluting with a gradient of methanol (0 to 15%) in 3% triethylamine in dichloromethane. Fractions containing pure compound 5 (triethylammonium salt) were collected and concentrated. Residue was suspended in 1N hydrochloric acid and extracted with ethyl acetate. The organic solution was separated, washed twice with brine, dried over MgSO$_4$, filtered, concentrated and dried in vacuo to give pure desired product 5 (5.37 g, 51%).
Compound 7.

A 0.5 L round bottom flask was charged with compound 5 (2.1 g, 2.29 mmol), trifluoroacetic acid (10 mL), CH$_2$Cl$_2$ (10 mL), and trifluoroacetic anhydride (10 mL). After being kept at room temperature for 10 min, the solution was concentrated. Residual TFA was removed by co-evaporation with dichloromethane. Drying under vacuum gave lactone 6 as an off-white solid. A solution of 6-aminohexanol (0.75 g, 6.44 mmol) and triethylamine (2.1 mL, 1.53 g, 15.0 mmol) in DMF (30 mL) was added to the lactone and resultant mixture was stirred for 20 min. Triethylamine (4.2 mL, 3.03 g, 30.0 mmol) was added followed by dimethoxytrityl chloride (13.47 g, 9.625 mmol. Reaction mixture was stirred overnight, diluted with ethyl acetate (300 mL) and washed with 10% citric acid (100 mL) and water (4×30 mL). The organic phase was separated, dried over Na$_2$SO$_4$, filtered and concentrated in vacuo. Residue was chromatographed on silica eluting with ethyl acetate to afford 2.2 g (91%) of desired product 7 as a red solid.
Compound 9.

A 25 mL flask was charged with magnetic stirring bar, compound 7 (2.10 g, 1.99 mmol), DMF (5.0 mL), triethylamine (0.50 mL, 0.362 g, 3.58 mmol) and phosphite (3) (0.873 g, 3.15 mmol). Argon was bubbled through solution during 2 min and tetrakis(triphenylphosphine) palladium(0) (0.30 g, 0.26 mmol) was added. Reaction mixture was stirred at 80° C. for 3 h. Another portion of each triethylamine (0.25 mL, 0.181 g, 1.8 mmol) and phosphite 3 (0.426 g, 1.57 mmol) and Pd(PPh$_3$)$_4$ (0.15 g, 0.13 mmol) was added to complete the reaction to yield (8). After being stirred at 80° C. for additional 1 h, the reaction was cooled and treated with triethylamine (2.23 mL, 1.618 g, 16.0 mmol), 1-methylimidazole (0.1 mL, 0.104 g, 1.26 mmol) and trimethylacetic anhydride (1.622 mL, 1.49 g, 4.0 mmol). Reaction was allowed to proceed at room temperature overnight and then concentrated. The oil obtained was dissolved in ethyl acetate (200 mL), washed with saturated sodium bicarbonate (50 mL), brine (2×30 mL), dried over Na$_2$SO$_4$, filtered from drying agent and concentrated. Residue was chromatographed on silica (eluent 30% DOA in ethyl acetate) to give pure desired product (9) (1.27 g, 0.81 mol, yield=41%) as an amorphous solid.
Compound 10.

A solution of compound 9 (1.20 g, 0.83 mmol) in methanol (50 mL) was treated with trifluoroacetic acid (0.5 mL, 0.74 g, 6.5 mmol). After being kept for 1 h at room temperature, the solution was neutralized by adding triethylamine (1.0 mL, 0.726, 7.2 mol), then concentrated in vacuo and re-dissolved in ethyl acetate (100 mL). The solution was washed with 10% citric acid (30 mL), brine (2×30 mL), dried over Na$_2$SO$_4$, filtered from drying agent and concentrated. Chromatography on silica gel eluting with ethyl acetate followed by concentration of the pure product fractions afforded 0.37 g (38%) of compound 10 as an amorphous solid.

Compound 11.

To a solution of compound 10 (0.35 g, 0.28 mmol), diisopropylammonium tetrazolide (53 mg, 0.31 mmol) in anhydrous $CH_2Cl_2$ (10 mL) was added 2-cyanoethyl N,N,N',N'-tetraisopropylphosphorodiamidite (0.169 g, 0.56 mmol). The reaction was stirred for 2 h and diluted with $CH_2Cl_2$ (80 mL). The solution was washed with saturated aqueous sodium bicarbonate (30 mL), brine (10 mL) and dried over $Na_2SO_4$. The extract was filtered and concentrated. The crude product was chromatographed on silica gel, which had been pre-washed with $CH_2Cl_2/Et_3N$ followed by $CH_2Cl_2$, using gradient (50-100%) of ethyl acetate in hexane to afford desired phosphoramidite 11 (0.22 g, 54%) as a white, amorphous solid.

Example 3

Protected 4' chloro-6-phosphonate benzo fluorescein analog (19)

This example illustrates the synthesis of a protected 4'-chloro-6-phosphonate benzofluorescein analog (19) as outlined in Reaction Scheme 3.

Compound 12

To a suspension of 4-bromophthalic anhydride (2.27 g, 10 mmol) in 30 mL of anhydrous 1,2-dichloroethane was added 3.3 g (25 mmol) of $AlCl_3$ followed by methyl 3-(3-chloro-2,4-dihydroxyphenyl)propionate (WO03023357)(2.3 g, 10 mmol). The mixture was stirred for several minutes to give a tan solution. The reaction was refluxed for 30 min, then cooled and concentrated. The resultant gelatinous material was partitioned between cold 1N hydrochloric acid (70 mL) and ethyl acetate (100 mL). The organic phase was washed with saturated NaCl, dried over $Na_2SO_4$ and concentrated. The resultant oil was suspended in dichloromethane and cooled to initiate crystallization. The crystals were collected by filtration, washed with cold dichloromethane and dried to afford 2.3 g (51%) of isomeric mixture of benzophenone 12.

Compound 13

1,3-Dihydroxynaphthalene (4.0 g, 25 mmol), benzophenone 12 (7.5 g, 16.3 mmol) and trifluoroacetic acid (20 mL) were combined and stirred until a solution was formed. To this solution was added methanesulfonic acid (20 mL) and the reaction was heated at 80° C. for 7 h. The reaction was cooled and poured into a mixture of ice and water. Precipitated solid was collected by filtration and washed with water. Drying in vacuo afforded 9.0 g (97%) of dye 13 (mixture of two isomers).

Compound 14

To a solution of compound 13 (2.75 g, 4.84 mmol) of trifluoroacetic acid (20 mL) was added 20 mL of trifluoroacetic anhydride. After being kept at room temperature for 1 h, the reaction was evaporated and the residue dried by co-evaporation with ethyl acetate. The solid residue was suspended in ethyl acetate (25 mL) and filtered. Washing with a small amount of ethyl acetate/hexane mixture (50%/50%) and drying under vacuum afforded 2.35 g (75%) of the desired lactone 14 as an off-white solid.

Compound 16

To a solution of 6-(O-DMT)-hexylamine (3.07 g, 7.25 mmol) (*Tetrahedron Letters* (2004), 45 (2), 317-320) and triethylamine (1.5 mL, 10.8 mmol) in 25 mL of anhydrous DMF was added 2.3 g (3.6 mmol) of solid lactone 14. After stirring for 1 h, N-methylimidazole (4 mL, 50 mmol) and trimethylacetic anhydride (4 mL, 19.7 mmol) were added. The reaction was allowed to proceed overnight. DMF was evaporated on a rotary evaporator and the resultant oil was partitioned between water and ethyl acetate. The organic phase was washed with brine and dried over $Na_2SO_4$. The material obtained after solvent evaporation was chromatographed on silica eluting with a gradient of ethyl acetate (30 to 50%) in hexane to remove excess DMT by-products (fastest moving components) and separate isomers. Minor, 5-isomer was eluted first followed by the major, 6-isomer. Fractions containing the 6-isomer were combined and concentrated. Drying under vacuum afforded 1.77 g (43%) of compound 16 as a pale yellow, amorphous solid.

Compound 17

Compound 16 (2.5 g, 2.2 mmol), phosphite 3 (1.63 g, 3.9 mmol) and triethylamine (0.82 mL, 5.9 mmol) were dissolved in a mixture of DMF (1.5 mL) and toluene (1.5 mL). To this solution was added 0.163 g (0.14 mmol) of tetrakis(triphenylphosphine)palladium (0). The mixture was warmed to ~50° C. to dissolve the catalyst and placed into an oil bath at 80° C. Heating with stirring was continued for 50 min. The reaction was cooled and diluted with ethyl acetate (30 mL). This mixture was loaded onto a silica gel column and eluted with ethyl acetate. Concentration of the pure product fractions and drying under vacuum afforded 2.2 g (68%) of the desired phosphonate 17 as a pale yellow, amorphous solid, Compound 18

To a solution of compound 17 (2.1 g, 1.43 mmol) in a mixture of MeOH (30 mL) and $CH_2Cl_2$ (60 mL) was added 0.6 mL of trifluoroacetic acid. After being kept at room temperature for 30 min, the reaction was neutralized with triethylamine (0.9 mL) and concentrated. The resultant oil was chromatographed on silica eluting, first, with ethyl acetate and, second, with 5% MeOH in ethyl acetate. The pure product fractions were concentrated and dried to afford 1.5 g (90%) of compound 18 as a pale yellow, amorphous solid.

Compound 19

2-Cyanoethyl tetraisopropylphosphorodiamidite (0.57 g, 1.9 mmol) was added dropwise to a solution of compound 18 (1.4 g, 1.2 mmol) and diisopropylammonium tetrazolide (0.27 g, 1.56 mmol) in 20 mL of anhydrous $CH_2Cl_2$. After being kept at room temperature overnight, the reaction was diluted with ethyl acetate and washed with saturated $NaHCO_3$. The organic phase was washed with brine, dried over $Na_2SO_4$ and concentrated to oil. This material was chromatographed on silica, which had been pre-washed with a mixture of triethylamine and ethyl acetate followed by ethyl acetate, eluting with ethyl acetate. Concentration of the product containing fractions and drying under vacuum afforded 1.2 g (73%) of the desired phosphoramidite 19 as a pale yellow, amorphous solid.

Example 4

This example illustrates the synthesis of a rotated 6-phosphonate rhodol analog (27) as outlined in Reaction Scheme 4.

Compound 23

4-Bromophthalic anhydride (647 g, 28 mmol) was dissolved in 7 mL of anhydrous DMF. To this solution was added 19 mL of toluene followed by 3.58 (18.9 mmol) of 8-hydroxyjulolidine. The reaction was heated with stirring at 110° C. for 30 min, then cooled to room temperature and concentrated. Obtained material was partitioned between water and $CH_2Cl_2$ (200 mL). The organic phase was dried over $Na_2SO_4$ and concentrated to give a dark oily material. It was chromatographed on silica eluting with $CH_2Cl_2$ followed by 5% MeOH in $CH_2Cl_2$. The product containing fractions were combined and concentrated. Drying under vacuum afforded 7.5 g (95%) of desired benzophenone 20 (mixture of isomers) as yellow amorphous solid.

Compound 21

Compounds 20 (4.16, 10 mmol) and methyl 3-(3-chloro-2,4-dihydroxyphenyl)propionate (2.31 g, 10 mmol) were suspended in 21 mL of methanesulfonic acid and heated slightly to dissolve the solids. When a solution was obtained it was placed into an oil bath and heated at 80° C. for 1 h. The reaction was cooled, mixed with ice (300 mL) and treated with 13.5 g of NaOH. The resultant mixture was heated to 65° C. and allowed to slowly cool to room temperature. Concentrated hydrochloric acid (2 mL) was added to acidify the solution to pH of 2. Precipitated material was collected by filtration and washed with water. Drying under vacuum at 50° C. over $P_2O_5$ afforded 5.3 g (89%) of the desired dye 21 (mixture of isomers) as a dark-red solid.

Compound 24

To a solution of compound 21 (3.0 g, 5 mmol) in 30 mL of trifluoroacetic acid was added 30 mL of trifluoroacetic anhydride. After being kept at room temperature for 30 min, the reaction was concentrated and the residue was dried by co-evaporation with $CH_2Cl_2$ (2×100 mL) to give lactone 22 as a viscous syrup. It was dissolved in 40 mL of $CH_2Cl_2$ and treated with a solution of O-DMT-6-aminohexanol (2.5 g, 5.9 mmol) and triethylamine (10 mL) in 10 mL of $CH_2Cl_2$. After being stirred at room temperature for 2 h, to the reaction was added triethylamine (3 mL), 1-methylimidazole (3 mL) and 6 mL of trimethylacetic anhydride. In order to expedite the reaction, the mixture was concentrated to an oil form and heated at 45° C. for 8 h. Water and ethyl acetate were added to partition components of the reaction. Organic phase was washed with 10% citric acid, saturated $NaHCO_3$, brine and dried over $Na_2SO_4$. The material obtained after solvent evaporation was chromatographed on silica eluting with 50% ethyl acetate in hexane to remove excess DMT by-products (fastest moving components) and separate isomers. Minor, 5-isomer was eluted first followed by the major, 6-isomer. Pure 6-isomer containing fractions were combined and concentrated. Drying under vacuum afforded 1.1 g (20%) of compound 24 as a pale-pink, amorphous solid.

Compound 25

Compounds 24 (0.8 g, 0.72 mmol), 7 (0.6 g, 1.7 mmol) and triethylamine (0.3 mL, 2.1 mmol) were dissolved in a mixture of DMF (0.7 mL) and toluene (0.7 mL). To this solution was added 70 mg (0.06 mmol) of tetrakis(triphenylphosphine) palladium (0). The mixture was slightly warmed (~50° C.) to dissolve the catalyst and placed into an oil bath at 80° C. Heating with stirring was continued for 30 min. The reaction was cooled and diluted with ethyl acetate (10 mL). This mixture was loaded onto a silica gel column and eluted, first, with ethyl acetate to remove by-products followed by 5% MeOH in $CH_2Cl_2$ to elute the product. Concentration of the pure product fractions and drying under vacuum afforded 0.9 g (88%) of the desired phosphonate 25 as a light-pink, viscous syrup.

Compound 26

To a solution of compound 25 (0.9 g, 0.63 mmol) in a mixture of MeOH (15 mL) and $CH_2Cl_2$ (30 mL) was added 0.3 mL of trifluoroacetic acid. After being kept at room temperature for 30 min, the reaction was neutralized with triethylamine (0.45 mL) and concentrated. Obtained red residue was chromatographed on silica eluting with a gradient of MeOH (5-15%) in dichloromethane. The pure product fractions were concentrated and dried to afford 0.5 g (71%) of compound 26 as a pale yellow, amorphous solid.

Compound 27

2-Cyanoethyl tetraisopropylphosphorodiamidite (0.21 g, 0.7 mmol) was added dropwise to a solution of compound 26 (0.45 g, 0.45 mmol) and diisopropylammonium tetrazolide (90 mg, 1.56 mmol) in 10 mL of anhydrous $CH_2Cl_2$. After being kept at room temperature for 3 h, the reaction was diluted with ethyl acetate and washed with saturated $NaHCO_3$. The organic phase was washed with brine, dried over $Na_2SO_4$ and concentrated to oil. This material was precipitated from small amount of ethyl acetate into anhydrous pentane to initially give an oily precipitate, which eventually solidified upon trituration with a fresh portion of pentane. The solid was collected by filtration and dried in vacuo to afford 0.4 g (74%) of phosphoramidite 27 as a light-pink, amorphous solid.

Example 5

This example illustrates the preparation of resorcinol 31 and dye reagent 39 as provided in Reaction Schemes 5 and 6.

4-(4-Nitrophenyl)-2,4-methoxybenzene (28). To a degassed solution of 4-bromonitrobenzene (24.37 g, 120.63 mmol) and 2,4-dimethoxyphenylboronic acid (20.95 g, 115.07 mmol) in 600 mL of 1,4-dioxane was added tetrakis(triphenylphosphine) palladium (0) (8.0 g, 7 mmol) followed by a solution of potassium carbonate (17.06 g, 124.3 mmol) in 120 mL of water. The reaction was stirred with heating at 80° C. for 24 h, cooled, filtered and concentrated. The resultant material was partitioned between ethyl acetate and water. The organic layer was washed with saturated $NaHCO_3$, brine, dried over $MgSO_4$ and concentrated. The resultant solid material was re-crystallized from hexane-ethyl acetate to afford 23.56 g of the desired product 28 as yellow crystals. $^1H$ NMR (dmso-$d_6$): δ 8.22 (d, J=8.8 Hz, 2H), 7.73 (d, J=8.8 Hz, 2H), 7.34 (d, J=8.5 Hz, 1H), 6.71 (d, J=2.2 Hz, 1H), 6.67 (dd, J=8.5, 2.2 Hz, 1H), 3.82 (s, 3H), 3.80 (s, 3H).

4-(4-Aminophenyl)-2,4-methoxybenzene (29). A solution of 28 (23.2 g, 89.5 mmol) in 300 mL of THF was hydrogenated at 50 psi in the presence of 2.0 g of 10% Pd/C for 8 h. The catalyst was removed by filtration through Celite. The filtrate was concentrated to afford crude amine 29 (20.8 g) which was used in the next reaction without additional purification. $^1H$ NMR (dmso-$d_6$): δ 7.10 (d, J=8.3 Hz, 3H), 6.60-6.50 (m, 4H), 5.04 (bs, 2H), 3.77 (s, 3H), 3.72 (s, 3H).

4-(4-Iodophenyl)-2,4-methoxybenzene (30). To a solution of crude amine 29 (20.8 g) in 80 mL of 1,4-dioxane was added a mixture of conc. HCl (347 mL) and ice (172 g). The reaction was placed in an ice/water bath and allowed to cool to 0-3° C. A solution of $NaNO_2$ in 420 mL of water was added with stirring over 20 min and stirring was continued for another 1 h. A solution of potassium iodide (150.5 g) was added with stirring over 10 min. The reaction was allowed to warm up to room temperature (~2 h) and extracted with ethyl acetate (1.2 L), The organic layer was washed with saturated $NaHCO_3$, $Na_2SO_3$ and brine and dried over $Na_2SO_4$. The crude product was chromatographed on silica eluting with 20% ethyl acetate in hexane. Concentration of the pure product fractions and drying under vacuum afforded 15.83 g (51.3%) of 30. $^1H$ NMR (dmso-$d_6$): δ 7.72 (d, J=8.3 Hz, 2H), 7.24 (d, J=8.3 Hz, 2H), 7.20 (d, J=8.5 Hz, 1H), 6.66 (d, J=2.2 Hz, 1H), 6.61 (dd, J=8.5, 2.2 Hz, 1H), 3.80 (s, 3H), 3.75 (s, 3H).

4-(4-Iodophenyl)resorcinol (31). To a solution of 30 (15.83 g, 46.54 mmol) in 150 mL of anhydrous dichloromethane at −70° C. was added dropwise 13.63 mL (144.3 mmol) of boron tribromide. After 40 min, the solution was allowed to warm to room temperature and slowly quenched by pouring into 500 g of ice. The mixture was diluted with 1 N (~390 mL) to pH of ~10 and extracted with ethyl acetate (300 mL). The organic layer was washed with brine and dried over $Na_2SO_4$. Evaporation of the solvent and drying under vacuum afforded pure 31 (14.4 g, 99%) as a pale pink solid $^1H$ NMR (dmso-$d_6$):

δ 9.48 (s, 1H), 9.39 (s, 1H), 7.68 (d, J=8.3 Hz, 2H), 7.29 (d, J=8.3 Hz, 2H), 7.04 (d, J=8.5 Hz), 6.40 (d, J=2.2 Hz, 1H), 6.29 (dd, J=8.5, 2.2 Hz, 1H).

6-Chloro-2-({3-chloro-2,4-dihydroxy-5-[2-(methoxycarbonyl)ethyl]phenyl}carbonyl)benzoic acid (32). To a solution of 3-chlorophthalic anhydride (3.7 g, 20 mmol) ((*J. Org. Chem.*, 1987, 52, 129-134) in 60 mL of anhydrous 1,2-dichloroethane was added 6.6 g (50 mmol) of $AlCl_3$ followed by 4.6 g (20 mmol) of methyl 3-(3-chloro-2,4-dihydroxyphenyl) propanoate (WO 03/023357). The reaction was heated at reflux for 30 min, cooled and concentrated, The resultant gelatinous material was partitioned between cold 2 N HCl (100 mL) and ethyl acetate (100 mL). The organic layer was washed with 1 N HCl, brine, dried over $Na_2SO_4$ and concentrated to afford an oily material (mixture of 6- and 2-chloroisomers). The oil was dissolved in dichloromethane (~40 mL) and briefly sonicated (ultrasound bath) to initiate crystallization. The mixture was cooled (ice/water bath) and allowed to crystallize for 30 min (extended crystallization time will result in co-crystallization of undesired 2-chloro isomer). The crystals were collected by filtration washed with cold dichloromethane. Drying under vacuum afforded 4.01 g of desired 6-chloro isomer (32). $^1$H NMR (DMSO-d6) δ 12.47 (br s, 1H), 10.78 (br s, 1H), 8.06 (d, J=7.7 Hz, 1H), 7.89 (d, J=7.9 Hz, 1H), 7.71 (t, J=7.9 Hz, 1H), 6.76 (s, 1H), 3.46 (s, 3H), 2.27 (m, 2H), 2.41 (t, J=6.6 Hz, 2H).

3-(7,13-Dichloro-16-(4-iodophenyl)-12,15-dihydroxy-1-oxospiro[3-hydroisobenzofuran-3,9'-xanthene]-11-yl)propanoic acid (33). A suspension of 32 (2.45 g, 7.8 mmol) and 31 (2.48 g, 6.0 mmol) in a mixture of TFA (12 mL) and methanesulfonic acid (12 mL) was heated at 80° C. with stirring for 3 h. The reaction was cooled and diluted with water (200 mL). The resultant solid was collected by filtration, washed with water and dried. The crude material was crystallized from ethyl acetate/hexane to afford 3.2 g (78%) of the desired dye 33 as an orange solid, $^1$H NMR (dmso-$d_6$): δ 12.07 (br s, 1H), 10.64 (s, 1H), 10.06 (s, 1H), 8.03 (d, J=7.2 Hz, 1H), 7.84 (d, J=7.6 Hz, 1H), 7.76 (t, J=-7.6 Hz, 1H), 7.68 (d, J=8.2 Hz, 2H), 7.13 (d, J=8.2 Hz, 2H), 6.93 (s, 1H), 6.63 (s, 1H), 6.62 (s, 1H), 2.68 (m, 2H), 2.35 (t, J=7 Hz, 2H).

Compound 34.

To a solution of the dye acid 33 (3.4 g, 5 mmol) in 30 mL of anhydrous DMF was added 3 mL of trimethylacetic anhydride followed by 3 mL of N-methylimidazole. After 1 h the reaction was concentrated and re-dissolved in ethyl acetate. The solution was washed with 10% citric acid, brine and dried over $Na_2SO_4$. Evaporation of the solvent afforded the crude product which was further purified by silica gel column chromatography eluting with 50% ethyl acetate in hexane. Concentration of the pure product fractions afforded 1.6 g (43%) of the desired lactone 34 as an off-white solid. $^1$H NMR (dmso-$d_6$): δ 8.07 (d, J=7.2 Hz, 1H), 7.87 (d, J=7.7 Hz, 1H), 7.79 (t, J=7.7 Hz, 1H), 7.73 (d, J=8.2 Hz, 2H), 7.55 (s, 1H), 7.03 (s, 1H), 7.02 (d, J=8.2 Hz, 1H), 7.00 (s, 1H), 2.97 (m, 2H), 2.83 (t, J=7 Hz, 2H), 1.13 (s, 9H).

Compound 36

A solution of the lactone 34 (1.6 g, 2.16 mmol) in 15 mL of anhydrous DMF was added to a cold (0° C., ice/water bath) solution of 6-(O-DMT)-hexylamine (1.1 g, 2.6 mmol) (*Tetrahedron Letters* (2004), 45 (2), 317-320) and triethylamine (0.3 mL) in 20 mL of anhydrous DMF. After being stirred at 0° C. for 2 h, the reaction was warmed to room temperature and treated with 1 mL of trimethylacetic anhydride and 0.44 mL N-methylimidazole. The reaction was allowed to proceed for 2 h and then concentrated. The residue was dissolved in ethyl acetate (~75 mL), washed with saturated $NaHCO_3$, brine and dried over $Na_2SO_4$. The solvent was evaporated and the resultant material chromatographed on silica eluting with 2:1 ethyl acetate:hexane. Concentration of the pure product fractions afforded 2.3 g (85%) of 36 as an amorphous, white solid, $^1$H NMR (dmso-$d_6$): δ 8.06 (d, J=7.4 Hz, 1H), 7.86 (d, J=7.7 Hz, 1H), 7.78 (t, J=7.7 Hz, 1H), 7.73 (d, J=8.2 Hz, 2H), 7.65 (br t, 1H), 7.53 (s, 1H), 7.4-7.2 (m, 9H), 7.01 (d, J=8.2 Hz, 2H), 6.99 (s, 1H), 6.91 (s, 1H), 6.87 (d, J=8.8 Hz, 4H), 3.72 (s, 6H), 2.92 (t, J=6.3 Hz, 2H), 2.86 (m, 2H), 2.58 (m, 2H), 2.15 (m, 2H), 1.15 (m, 2H), 1.38 (s, 9H), 1.25 (m, 4H), 1.51 (m, 2H), 1.12 (s, 9H).

Compound 37

To a solution of 36 (2.3 g, 1.85 mmol), bis-(4-trifluoroacetamidobutyl)phosphite (1.15 g, 1.5 eq.), triethylamine (0.75 mL) in 4 mL of toluene was added tetrakis(triphenylphosphine)palladium (0) (130 mg, 0.11 mmol). The reaction was stirred at 80° C. for 1 h and cooled to room temperature. The mixture was chromatographed on silica eluting with a gradient of acetone (40 to 60%) in hexane. The pure product fractions were concentrated and dried under vacuum to afford 2.66 g (94%) of the desired phosphonate 37 as a white, amorphous solid. $^1$H NMR (dmso-$d_6$): δ 9.42 (br t, 2H), 8.05 (d, J=7.4 Hz, 1H), 7.86 (d, J=7.8 Hz, 1H), 7.78 (t, J=7.9 Hz, 1H), 7.67 (m, 3H), 7.57 (s, 1H), 7.4-7.2 (m, 11H), 7.10 (s, 1H), 6.91 (s, 1H), 6.87 (d, J=8.8 Hz, 4H), 3.93 (m, 4H), 3.72 (s, 6H), 3.18 (m, 4H), 2.92 (t, J=6.3 Hz, 2H), 2.86 (m, 2H), 2.58 (m, 2H), 2.15 (m, 2H), 1.55 (m, 10H), 1.42 (s, 9H), 1.27 (m, 4H), 1.15 (m, 2H), 1.07 (s, 9H). $^{31}$P NMR (dmso-$d_6$) δ18.14 (s).

Compound 38

To a solution of 37 (2.4 g, 1.56 mmol) in a mixture of dichloromethane (50 mL) and methanol (50 mL) was added 0.6 mL of TEA. The solution was kept at room temperature for 30 min and neutralized by adding 0.9 mL of triethylamine. The reaction was concentrated and chromatographed on silica eluting with a gradient of methanol (0 to 5%) in ethyl acetate. Concentration of the pure product fractions afforded 1.86 g (97%) of compound 38 as a white, amorphous solid. $^1$H NMR (dmso-$d_6$): δ9.41 (br t, 2H), 8.08 (d, J=7.4 Hz, 1H), 7.87 (d, J=7.8 Hz, 1H), 7.80 (t, J=7.9 Hz, 1H), 7.67 (m, 3H), 7.58 (s, 1H), 7.38 (dd, J=13 Hz, 6 Hz, 2H), 7.10 (s, 1H), 6.91 (s, 1H), 4.33 (t, J=5 Hz, 1H), 4.11 (m, 4H), 3.37 (t, J=6 Hz, 2H), 3.18 (m, 4H), 2.88 (m, 2H), 2.58 (m, 2H), 2.16 (m, 2H), 1.55 (m, 10H), 1.40 (s, 9H), 1.34-1.16 (m, 6H), 1.03 (s, 9H), $^{31}$P NMR (dmso-$d_6$) δ 18.05 (s).

Compound 39

Diisopropylammonium tetrazolide (0.26 g, 1.5 mmol) was added to a solution of 38 (1.79 g, 1.46 mmol) in 20 mL of anhydrous dichloromethane. The reaction was stirred for 5 min to dissolve the tetrazolide. To the resultant solution was added 0.7 g (2.3 mmol) of 2-cyanoethyl N,N,N',N'-tetraisopropylphosphordiamidite. After being stirred for 5 h, the reaction was diluted with ethyl acetate (100 mL), washed with saturated $NaHCO_3$, brine and dried over $Na_2SO_4$. The extract was concentrated and re-dissolved in a small amount of ethyl acetate (~2 mL). Ether (10 mL) was added to precipitate the product. The mixture was further diluted with anhydrous heptane (200 mL) and the resultant emulsion was allowed to settle (~10 min). The residue, obtained after decanting the liquid phase, was dried under vacuum to afford 1.69 g (81%) of phosphoramidite 39 as an off white, amorphous solid. $^1$H NMR (dmso-$d_6$): δ 9.41 (hr t, 2H), 8.08 (d, J=7.4 Hz, 1H), 7.87 (d, J=7.8 Hz, 1H), 7.80 (t, Hz, 1H), 7.67 (m, 3H), 7.58 (s, 1H), 7.38 (dd, J=13 Hz, 6 Hz, 2H), 7.10 (s, 1H), 6.91 (s, 1H), 3.93 (m, 4H), 3.72 (m, 2H), 3.54 (m, 4H), 3.18 (m, 4H), 2.88 (m, 2H), 2.92 (t, J=6.3 Hz, 2H), 2.58 (m, 2H), 2.16 (m, 2H), 1.55 (m, 10H), 1.40 (s, 9H), 1.34-1.16 (m, 6H), 1.12 (t, J=6 Hz, 12H), 1.03 (s, 9H). $^{31}$P NMR (dmso-d$_6$) δ 146.73 (s), 18.05 (s).

Example 6

This example illustrates the preparation of an asymmetric mono-DMT-mono-trifluoroacetamidobutyl phosphite reagent (41) as an example of alternative phosphonylation reagent. A schematic representation of the reactions is provided in Reaction. Scheme 7.

Compound 41

To a solution of mono-DMT-1,6-hexanediol (40) (*Nucleic Acids Research* (1993), 21 (1), 145-150) (4.0 g, 9.5 mmol) and compound 5 (1.76 g, 9.5 mmol) in 40 mL of anhydrous pyridine was added 2.5 g (~10 mmol, contained 10-15% phenol) of diphenylphosphide. After being kept at room temperature for 1 h the reaction was concentrated and dissolved in ethyl acetate (100 mL). The solution was washed with 10% citric acid, saturated NaCl and dried over Na$_2$SO$_4$. Material, which was obtained after concentration, was chromatographed on silica eluting with a gradient of ethyl acetate (60-100%) in hexane. Bis-DMT by-product was eluted first followed by desired mono-DMT-mono-trifluoroacetamido derivative (41). Appropriate fractions were combined, concentrated and dried in vacuo to afford 2.0 g (32%) of phosphite 41 as a colorless, viscous liquid. $^1$H NMR (dmso-d6) δ 9.44 (br t, 1H), 7.4-7.1 (m, 9H), 6.88 (d, J=8 Hz, 4H), 6.79 (d, J=694 Hz, 1H), 3.96 (m, 4H), 3.73 (s, 6H), 3.21 (m, 2H), 2.94 (t, J=6 Hz, 2H), 1.57 (m, 8H), 1.30 (m, 4H), $^{31}$P NMR (dmso-d$_6$) δ 9.01 (d, J=694 Hz).

Example 7

This example illustrates the preparation of a hydroxyhexyl-6-phosphonofluorescein and its phosphoramidite (36) according to methods outlined in Reaction Scheme 8.

Compound 42

A suspension of 4-bromophthalic anhydride (6.8 g, 30 mmol) and resorcinol (8.8 g, 80 mmol) in 50 mL of methanesulfonic acid was heated with stirring at 80° C. for 5 h. The reaction was cooled and poured into a mixture of ice and water (300 mL). Solid precipitate was collected by filtration and washed with water. Drying under vacuum gave 12.1 g (98%) of bromofluorescein 42 (mixture of 5- and 6-isomers) as an orange solid.

Compound 43

A solution of compound 42 (4.1 g, 10 mmol), 1-methylimidazole (1 mL) and trimethylacetic anhydride (8 mL, 40 mmol) was heated at 50° C. for 2 h. TLC analysis (20% EtOAc in hexane) showed complete conversion of starting material into two new products (5- and 6-isomers). MeOH (5 mL) was added to quench excess anhydride. After being kept at room temperature for 1 h, the reaction was concentrated and re-dissolved in ethyl acetate. The solution was washed with 10% citric acid, saturated NaHCO$_3$, saturated NaCl and dried over Na$_2$SO$_4$. After solvent evaporation, the mixture was chromatographed on silica eluting with 20% ethyl acetate in hexane. Three groups of fractions were collected. First one contained the faster eluting, 5-isomer, Second group was a mixture of 5- and 6-isomers, and, the third group of fractions contained pure 6-isomer, slower eluting product (compound 43). Evaporation of the solvent and drying under vacuum afforded 1.6 g of 5-isomer, 1.6 g of isomeric mixture and 1.9 g (33%) of the desired, 6-isomer (compound 43). $^1$H NMR (dmso-d6) δ 7.99 (m, 2H), 7.78 (s, 1H), 7.26 (d, 1.8 Hz, 2H), 6.95 (m, 4H), 1.31 (s, 18H).

Compound 44

A solution of compound 43 (1.16 g, 2.0 mmol), compound 41 (1.9 g, 2.9 mmol), triethylamine (0.8 mL, 5.75 mmol) and tetrakis(triphenylphosphine)palladium(0) (140 mg, 0.12 mmol) in 3 mL of toluene was heated at 80° C. for 1 h. The reaction was cooled and diluted with 20 mL of 66% ethyl acetate in hexane. Precipitated triethylammonium bromide was filtered off. The filtrate was loaded onto a silica gel column. Elution with a gradient (50 to 80%) of ethyl acetate in hexane followed by concentration and drying in vacuo afforded 1.95 g (85%) of phosphonate 44 as an amorphous, white solid material. $^1$H NMR (dmso-d$_6$) δ 9.34 (t, 1H), 8.20 (dd, J$_1$=8 Hz, J$_2$=3 Hz, 1H), 8.04 (dd, J$_1$=12.3 Hz, J$_2$=8 Hz, 1H), 7.66 (d, J=12.9 Hz, 1H), 7.4-71 (m, 11H), 6.8 (m, 8H), 3.92 (m, 4H), 3.71 (s, 6H), 3.07 (q, J=6 Hz, 2H), 2.89 (t, 6 Hz, 2H), 1.46 (m, 8H), 1.28 (s, 18H), 1.28-1.05 (m, 4H). $^{31}$P NMR (dmso-d$_6$) δ 15.35 (s).

Compound 45

To a solution of compound 44 (1.85 g, 1.6 mmol) in a mixture of MeOH (30 mL) and CH$_2$Cl$_2$ (60 mL) was added 0.6 mL of trifluoroacetic acid. After being kept at room temperature for 30 min, the reaction was neutralized with triethylamine (1 mL) and concentrated. Obtained red residue was chromatographed on silica eluting with a gradient of MeOH (0-5%) in ethyl acetate. The pure product fractions were concentrated and dried to afford 1.05 g (77%) of compound 45 as an amorphous, white solid. $^1$H NMR (dmso-d$_6$) δ 9.35 (br t, 1H), 8.22 (dd, J$_1$=8 Hz, J$_2$=3 Hz, 1H), 8.06 (dd, J$_1$=12.6 Hz, J$_2$=8 Hz, 1H), 7.67 (d, J=12.9 Hz, 1H), 7.27 (s, 2H), 6.94 (m, 4H), 4.31 (t, J=5.4 Hz, 1H), 3.95 (m, 4H), 3.31 (t, 6 Hz, 2H), 3.07 (q, J=6 Hz, 2H), 1.46 (m, 8H), 1.31 (s, 18H), (m, 4H), $^{31}$P NMR (dmso-d6) δ 15.27 (s).

Compound 46

2-Cyanoethyl N,N,N'N'-tetraisopropylphosphorodiamidite (0.57 g, 1.9 mmol) was added dropwise to a solution of compound 45 (1.0 g, 1.18 mmol) and diisopropylammonium tetrazolide (0.2 g, 1.17 mmol) in 20 ml., of anhydrous CH$_2$Cl$_2$. After being kept at room temperature overnight, the reaction was diluted with ethyl acetate and washed with saturated NaHCO$_3$. The organic phase was washed with brine, dried over Na$_2$SO$_4$ and concentrated. The residue was chromatographed on silica, which had been pre-washed with a mixture of triethylamine and ethyl acetate followed by ethyl acetate, eluting with ethyl acetate. Concentration of the product containing fractions and drying under vacuum afforded 0.72 g (58%) of the desired phosphoramidite 46 as a white, amorphous solid.

Example 8

This example illustrates the synthesis of phosphonate cyanine phosphoramidite (51) using methods outlined in Reaction Scheme 9.

1-(sulfobutyl)-2,3,3-trimethylindolinum, inner salt (47). A mixture of 2,3,3-trimethylindolenine (6.3 g, 40 mmol) and 1,4-butane sultone (5.4 g, 40 mmol) was heated at 100° C. for 5 h. The resultant dark semi-solid was suspended in dichloromethane and cooled to inforce product crystallization. The crystals were collected by filtration, washed with cold dichloromethane and ether. Drying under vacuum afforded 9.9 g (83%) of the desired indolinum salt 47 as a pale pink, hydroscopic solid.

1-(Sulfobutyl)-2,3,3-trimethyl-5-bromoindolinum, inner salt (49) was prepared as described above for non-brominated analog starting from 5-bromo-2,3,3-trimethylindolenine (*J. Heterocycle Chem.* 2002, 39(2), 263-269).

Compound 48

A suspension of 47 (6.0 g, 20.3 mmol) and N,N'-diphenylformamidine (4.0 g, 20.4 mmol) in 25 mL of acetic anhydride was heated at 110° C. with stirring for 1.5 h. The resultant solution was cooled to room temperature and left for product crystallization overnight. The crystals were collected by filtration washed with small amount of dichloromethane and plenty of ether. Drying under vacuum afforded 6.66 g (7 of compound 48 as an orange-red solid.

Compound 50

A suspension of 49 (3.7 g, 9.9 mmol) and 48 (4.0 g, 10 mmol) in 7 mL of acetic anhydride was heated at 110° C. with stirring for 1 h and cooled to room temperature. The insoluble material was collected by filtration and washed with small amount of acetic anhydride and plenty of ether. Drying under vacuum afforded 4.0 g (61%) of compound 50. The crude material was utilized in the next reaction without additional purification.

Compound 51

A mixture of 50 (0.68 g, 1.0 mmol), triethylamine (0.5 mL, 3.75 mmol), phosphite 41 (0.96 g, 1.46 mmol) in 1.5 mL of DMF was degassed under vacuum. To this suspension was added 70 mg (0.06 mmol) of tetrakis(triphenylphosphine) palladium (0). The reaction was heated at 80° C. with stirring for 1 h and then cooled to room temperature. The mixture was chromatographed on silica eluting with a gradient of MeOH (0-15%) in 5% triethylamine in dichloromethane. Concentration of the product containing fractions and drying under vacuum afforded 1.2 g (89%) of the desired phosphonate 51 as an amorphous, red solid.

Compound 52

To a solution of 51 (1.1 g, 0.81 mmol) in a mixture of dichloromethane (50 mL) and MeOH (50 mL) was added 0.1 mL of TFA. After being kept at room temperature for 1 h, the reaction was neutralized with 0.2 mL of triethylamine and concentrated. The residue was then chromatographed on silica eluting with a gradient of MeOH (0-15%) in dichloromethane (plus 10% triethylamine). The pure product fractions were concentrated and dried to give 0.62 g (77%) of compound 52.

Compound 53

To a solution of 52 (0.6 g, 0.6 mmol) and diisopropylethylamine (1 mL) in 10 mL of anhydrous dichloromethane was added dropwise with stirring 0.2 mL (0.9 mmol) of 2-cyanoethyl N,N-diisopropylchlorophosphoramidite. After being kept at room temperature, the reaction was diluted with ether (100 mL). The liquid phase was decanted and the residue washed with more ether. The residual syrupy material was foamed up to afford 0.7 g of the unstable phosphoramidite 53 as a purple, amorphous solid. Due to the instability the phosphoramidite had to be utilized for DNA synthesis within one day after preparation. From a practical consideration, the phosphoramidte (53) was synthesized daily from intermediate 52 in quantities sufficient for oligonucleotide synthesis requirement for the day.

Example 9

This example illustrates the preparation of a phosphonate Cy5 CPG reagent 59 as outlined in Reaction Scheme 10, Compound 54

A mixture of 5-iodo-2,3,3-trimethyl-3H-indolenine (*Eur. J. Med. Chem. Chim. Ther.* 1974, 9(3), 274-280) (4.74 g, 16.6 mmol) and propanesultone (2.0 g, 16.4 mmol) was heated at +100° C. for 30 min. The reaction mixture was cooled and triturated with ether. Solid material was filtered off, washed with ether, dichloromethane and dried in vacuum to give desired product (5.5 g, 82%) as off-white solid.

Compound 55

To a solution of 54 (2.3 g, 5.6 mmol) and malonaldehyde bis(phenylimino)monohydrochloride (0.72 g, 2.8 mmol) in 20 ml of pyridine was added acetic anhydride (3.4 g, 33.6 mmol). The reaction was stirred at room temperature for 4 h and concentrated. The resultant material was chromatographed on silica eluting with a gradient of methanol (0-10%) in dichloromethane (plus 5% pyridine). Yield of the desired dye 55 was 56% (purple solid).

Compound 56

A mixture of 55 (0.46 g, 0.49 mmol), phosphite 41 (1.0 g, 1.53 mmol), N-ethylmorpholine (0.3 ml) and DMF (1 ml) was degassed under vacuum for 1 min. Tetrakis(triphenylphosphine)palladium (0) (0.1 g, 0.086 mmol) was added, and the mixture was stirred at 80° C. for 1 h. The reaction mixture was cooled and chromatographed on silica eluting with a gradient of methanol (0-10%) in dichloromethane (plus 5% pyridine). Concentration of the pure product fractions and drying under vacuum afforded 0.8 g (82%) of the desired phosphonate dye 56.

Compound 57

To a solution of 56 (0.7 g, 0.35 mmol) in 20 ml of dichloromethane was added methanol (0.0115 g, 0.35 mmol) followed by TFA (0.05 ml). The reaction was allowed to proceed for 10 min and neutralized with triethylamine (0.1 ml), Solvent was evaporated and the resultant material was chromatographed on silica eluting with a gradient of methanol (0-20%) in dichloromethane (plus 5% pyridine). Concentration of the pure product fractions and drying under vacuum afforded 0.12 g (20%) of the desired product 57, Compound 58

A solution of 57 (0.11 g, (0.065 mmol), N-methylimidazole (5 mg, 0.065 mmol), triethylamine (80 mg, 0.78 mmol) and succinic anhydride (40 mg, 0.39 mmol) in 1.5 ml of anhydrous DMF was stirred at room temperature for 20 h. Pentafluorophenyl trifluoroacetate (0.22 g, 0.78 mmol) was added. After being kept at room temperature for 1 h, the reaction was concentrated and triturated with ether followed by ethyl acetate. Drying under vacuum afforded crude (contaminated with TFA salts) product 58 which was used in the next reaction without additional purification.

Preparation of Controlled Pore Size Support (CPG) 59

Long chain aminoalkyl CPG, 500 A (1.5 g, 105 μmol/g) was added to a solution of 58 (90 mg, ~45 μmol) and triethylamine (50 mg, 49 mmol) in 8 ml of anhydrous DMF. The suspension was stirred using an orbiter shaker for 3 h and then treated with pyridine (1 ml) and acetic anhydride (1 ml) to cap unreacted amino groups. After being stirred for another 1 h, the CPG was collected by filtration, washed with DMF, ethyl acetate and dried in vacuo.

DMT loading: 18 μmol/g.

Example 10

This example illustrates the preparation of a phosphonate Cy5 PFP ester reagent 66 as outlined in Reaction Scheme 11.

Compound 60

A mixture of 5-iodo-2,3,3-trimethyl-3H-indolenine (*Eur. J. Med. Chim. Ther.* 1974, 9(3), 274-280) (1.0 g, 3.5 mmol) and tert-butyl 6-iodohexanoate (1.382 g, 4.6 mmol) was heated at +90° C. for 9 h. The reaction mixture was cooled and triturated with ether. Solid material was filtered off, washed with ether and dried in vacuum to give desired product (1.2 g, 59%) as pale pink solid. NMR (dmso-$d_6$): δ 8.31 (s, 1H), 8.00 (d, J=8.4 Hz, 1H), 7.80 (d, J=8.4 Hz, 1H), 4.42 (t, J=7.4 Hz, 2H), 3.91 (bs, 2H), 2.81 (s, 3H), 2.19 (t, J=7.2 Hz, 2H), 1.80 (qn, J=7.0 Hz, 2H), 1.53 (s, 6H), 1.50 (qn, J=7.2 Hz, 2H), 1.36 (s, 9H).

Compound 61

A mixture of 5-iodo-2,3,3-trimethyl-3H-indolenine (2.0 g, 7.0 mmol) and ethyl iodide (1.76 ml, 3.42 g, 22 mmol) was heated at +90° C. for 3 h. The reaction mixture was cooled and triturated with ether. Solid material was filtered off, washed with ether and dried in vacuum to give desired product (2.45 g, 79%) as pink solid. NMR (dmso-$d_6$): δ 8.31 (s, 1H), 8.00 (d, J=8.4 Hz, 1H), 7.80 (d, J=8.4 Hz, 1H), 4.46 (q, J=7.4 Hz, 2H), 2.80 (s, 3H), 1.52 (s 6H), 1.41 (t, J=7.2 Hz, 3H).

Compound 62

A mixture of 61 (1.5 g, 3.4 mmol), malonaldehyde bis(phenylimino)monohydrochloride (1.76 g, 6.8 mmol), acetyl chloride (2.5 ml), and acetic anhydride (25 ml) was heated at +120° C. for 1.5 h. The reaction mixture was cooled and added dropwise to stirred ether. Solid material was filtered off, washed with ether, EtOAc and dried in vacuum to give crude product (1.87 g, 90%) as brown solid, which was used further without purification.

Compound 63

A mixture of 62 (1.25 g, 2.04 mmol), 60 (1.162 g, 2.0 mmol), acetic anhydride (2 ml), and pyridine (20 ml) was magnetically stirred at room temperature for 1.5 h. The reaction mixture was concentrated in vacuum, residue was dissolved DCM/MeOH (9:1) mixture, and solution was added dropwise to stirred ether. The precipitate was filtered off, washed with ether, and dried in vacuum to give crude product, which was purified on silica column (10% MeOH/DCM) to give desired product (0.94 g, 50%) as purple solid. $^1$H NMR (dmso-d6): δ 8.34 (t, J=13.0 Hz, 2H), 8.06 (s, 2H), 7.75-7.71 (m, 2H), 7.24 (d, J=8.5, 1H), 7.23 (d, 1H), 6.57 (t, J=12.2 Hz, 1H), 6.30 (d, J=13.3 Hz, 2), 4.10 (m, 4H), 2.15 (t, J=7.2 Hz, 2H), 1.67 (s, 12H), 1.60 (m, 2H), 1.50 (m, 2H), 1.33 (s, 9H), 1.30 (m, 2H), 1.23 (t, J=7.2 Hz, 3H).

Compound 64

A 25 ml flask was charged with compound 63 (0.84 g, 0.9 mmol), phosphite 3 (2.24 g, 5.4 mmol), DMF (2 ml), toluene (2 ml), and ethylmorpholine (0.859 ml, 0.777 g, 6.75 mmol). The flask was flushed with argon and argon was bubbled through solution during 2 min. Tetrakis(triphenylphosphine)palladium (0) (208 mg, 0.18 mmol) was added and reaction mixture was magnetically stirred at +80° C. for 2 h. The reaction mixture was cooled to room temperature and added dropwise to stirred methyl 1-butyl ether. The solution was decanted and residual oily material was rinsed with ether, dissolved in MeOH/DCM (9:1) mixture and separated on silica column (10-15% MeOH in DCM) to give desired product (250 mg, 19%) as a purple solid, $^1$H NMR (dmso-d6): δ 9.42 (t, J=4.8 Hz, 4H), 8.46 (t, J=13.0 Hz, 2H), 7.95 (d, J=12.6 Hz, 2H), 7.80-7.70 (m, 2H), 7.54-7.52 (m, 2H), 6.67 (t, J=12.4 Hz, 1H), 6.41 (d, J=13.5 Hz, 2H), 4.15 (m, 4H), 3.95 (m, 8H), 3.17 (qr, J=6.1 Hz, 8H), 2.18 (t, J=7.2 Hz, 2H), 1.71 (s, 12H), 1.65-1.45 (m, 20H), 1.33 (s, 9H), 1.30-1.20 (m, 5H). $^{31}$P NMR (dmso-d6): δ 18.72.

Compound 65

A mixture of 64 (0.25 g, 0.16 mmol), dichloromethane (5 ml), and trifluoroacetic acid (5 ml) was magnetically stirred at room temperature for 1 h. The reaction mixture was concentrated in vacuum and co-evaporated with DMF. The residue was dissolved in acetone and diluted with ether. The resultant solution was decanted, and the remaining oily residue was rinsed with ether and dried in high vacuum to give desired product (0.20 g, 88%) as purple solid. $^1$H NMR (dmso-$d_6$): δ 9.42 (t, J=4.7 Hz, 4H), 8.45 (t, J=13.0 Hz, 2H), 7.95 (d, J=12.6 Hz, 2H), 7.78-7.70 (m, 2H), 7.53 (d, J=7.7 Hz, 2H), 6.68 (t, J=12.4 Hz, 1H), 6.42 (d, J=13.5, 1H), 6.41 (d, J=13.5, 1H), 4.15 (m, 4H), 3.98 (m, 8H), 3.55 (bs, 1H), 3.17 (qr, J=6.1 Hz, 8H), 2.20 (t, J=7.2 Hz, 2H), 1.71 (s, 12H), 1.65-1.45 (m, 20H), 1.40 (m, 2H), 1.27 (t, J=7.2 Hz, 3H). $^{31}$P NMR (dmso-d6): δ 18.72.

Compound 66

Pentafluorophenyl trifluoroacetate (0.18 g, 0.64 mmol) was added to a mixture of 65 (0.20 g, 0.14 mmol), DMF (3 ml), and N,N-diisopropylethylamine (0.082 g, 0.64 mmol). The resultant mixture was magnetically stirred at room temperature for 10 min. The reaction mixture was then concentrated under reduced pressure and the residue was dissolved in acetonitrile and diluted with ether. The resultant solution was decanted from the oily residue. The operation was repeated, and the oily residue was then rinsed with ether and dried under high vacuum to give desired product (0.15 g, 56%) as purple solid. $^1$H NMR (dmso-d6): δ 9.43 (bs, 4H), 8.45 (t, J=13.0 Hz. 2H), 7.96 (d, J=12.4 Hz, 2H), 7.78-7.69 (m, 2H), 7.54 (d, J=6.2 Hz, 2H), 6.65 (t, J=12.3 Hz, 1H), 6.40 (d, J=12.9 Hz, 2H), 4.15 (m, 4H), 3.98 (m, 8H), 3.17 (qr, J=5.9 Hz, 8H), 2.80 (t, J=6.9 Hz, 2H), 1.8-1.7 (m, 2H), 1.71 (s, 12H), 1.65-1.40 (m, 18H), 1.3-1.2 (m, 5H). $^{31}$P NMR (dmso-d6): δ 18.72.

Example 11

Comparison of Reverse Phase HPLC Retention Times for Phosphonate and Non-Phosphonate Dye-Octathymidylates This example demonstrates a) the oligonucleotide synthesis with a protected xanthene phosphonate phosphoramidite h) the deblocking of the oligonucleotide conjugate and c) the increased polarity of the xanthene phosphonate oligonucleotide conjugate.

Oligonucleotide synthesis was performed on a AB 3900 DNA Synthesizer (Applied Biosystems, Foster City, Calif.). The protected oligonucleotide conjugates was treated under standard conditions (10% ethanol in concentrated NH$_4$OH for 2 hours at 70° C.) to yield the pure unprotected oligonucleotide conjugates.

The purified oligonucleotide conjugates in Table 4 were analyzed by C18 reverse phase chromatography. JINX conditions were: C18 reverse phase, Luna, 4.6×100 mm column, gradient of acetonitrile (0-45%) in 30 min, 0.1 M triethylammonium acetate, pH 7.5 with a flow/rate of 1 mL/min.

As shown in Table 4, the retention times of the phosphonate xanthenes is much faster than the non-phosphonate xanthenes confirming their more polar nature.

TABLE 4

Comparison of reverse phase HPLC retention times, absorption and fluorescence properties for phosphonate and non-phosphonate dye-octathymidylates

| | Retention time (min) | Abs max (nm) | Fluor max (nm) | Relative brightness |
|---|---|---|---|---|
| [structure 1; R = H / R = PO(OH)(O(CH$_2$)$_4$NH$_2$)] | 17.6<br>11.6 | 520.5<br>523 | 550<br>554 | 1.0<br>1.1 |
| [structure 2; R = H / R = PO(OH)(O(CH$_2$)$_4$NH$_2$)] | 20.7<br>14.6 | 552<br>554 | 576<br>577 | 1.0<br>1.0 |
| [structure 3; R = H / R = PO(OH)(O(CH$_2$)$_4$NH$_2$)] | 17.5<br>15.7 | | 540<br>548 | |
| [structure 4] | 12.8<br>11.4 | 495<br>494 | 516<br>515 | 1.0<br>1.0 |

TABLE 4-continued

Comparison of reverse phase HPLC retention times, absorption and fluorescence properties for phosphonate and non-phosphonate dye-octathymidylates

| | Retention time (min) | Abs max (nm) | Fluor max (nm) | Relative brightness |
|---|---|---|---|---|

R = (phosphate group structure: —P(=O)(OH)—O—)

$T_8$ = (octathymidylate structure shown)

Example 12

The Oligonucleotide Synthesis of a MB-Q-Oligonucleotide-XP Conjugate

This example demonstrates a) the synthesis of a MB-Q-oligonucleotide-XP conjugate, b) the removal of protecting groups and c) the purification of the conjugate.

Figure 3:
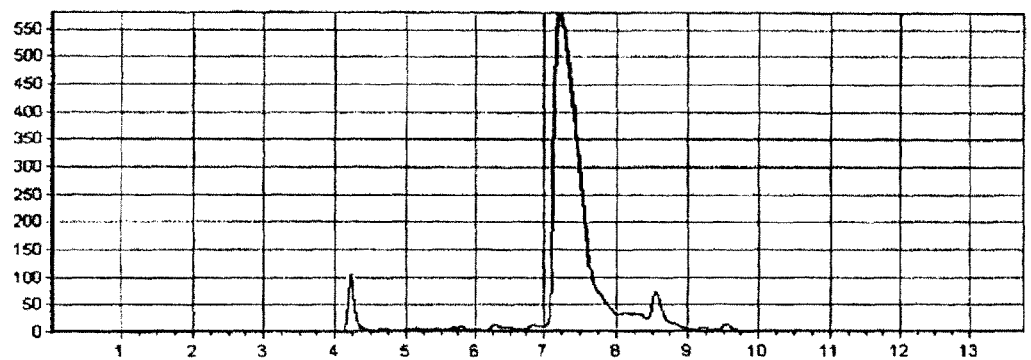
FIG. 3 illustrates an HPLC chromatogram of a MB-Q-oligonucleotide-XP (see Example 9).

FIG. 3 shows a example of oligonucleotide synthesis of 5'-minor groove binder-quencher DNA probes labeled at the 3' end with a phosphonate xanthene dye using phosphoramidite reagent 22. This example demonstrates the successful and reproducible phosphoramidite coupling chemistry and efficient removal of protecting groups during the deprotection. The oligonucleotide was synthesized as described in Kutyavin et al, *Nucl. Acids Res.*, 28:655-661 (2000). The conjugate was purified on a Wave System, Transgenomic, Inc., Omaha, Nebr. The retention time of the conjugate corresponded to a position observed for similar fully deprotected conjugates.

Example 13

This example demonstrates the use of a phosphonate-labelled MGB Eclipse probe in a multiplexed hybridization-based detection assay, where the HSV 1,2 probe is labeled with FAM and the internal control is labeled with a phosphonate dye (14).

Real-Time PCR Using MGB Eclipse XP-Labeled Probe

Real-time PCR was conducted on either an ABI Prism® 7900 Sequence Detection System (SDS) (Applied Biosystems, Foster City, Calif.), or on a MJ Research PTC-200 Peltier Thermal Cycle (Waltham, Mass.) (Afonina, et al., *J. Clin. Ligand Assay*, Vol. 25, Vol. 23, pp. 268). On both instruments, 50 cycles of a three step PCR (95° C. for 5 s, 58° C. for 20 s and 76° C. for 30 s) profile was run, after an initial 2 min at 95° C. If necessary, fluorescent data were collected at 58° C. with an ABI 7900 SDS. Commercially available 2× Jump Start™ Taq Ready Mix™ for Quantitative PCR with 2 mM final Mg++ concentration (Sigma #D 74403) supplemented with JumpStart Taq Polymerase (Sigma Catalog #90 4184) to a final amount of 0.37 U/µl was used. Final concentration of both probes was 2 µM. Each 5 µl reaction concentration of limiting primer was 0.1 µM and excess primer was 2 µM. Each 5 µl reaction contained 10 ng of genomic DNA lyophilized in 96 or 384 well plates with a speed vac prior to reaction set up. A Biomek® 2000 Laboratory Automation Station (Beckman Coulter, USA) was used to setup PCR reactions.

HSV 1,2 Detection

Successful multiplexing requires that the amplification of both the target and internal control are close to 100% efficient (Livak, K J and Schmittgen, T D. 2001. *Methods* 25: 402-408). When such PCR efficient reactions are multiplexed in a single reaction the real-time data from a titration curve of $C_t$ against concentration should give a slope of −3.333 with $R^2$ value of greater than 0.99. In the case where the HSV 1,2 FAM-labeled probe and the phosphonate-labeled internal control were multiplexed, the slope is −3.14 with a $R^2$ of 0.996, an acceptable value to proceed with the detection of unknown samples.

Figure 4:
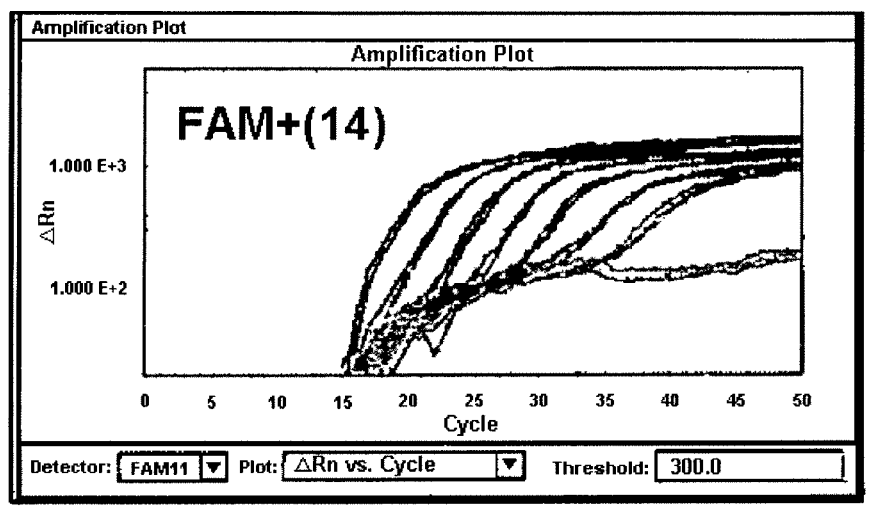
FIG. 4 illustrates the titration of a HSV 1,2 MGB Eclipse probe assay wherein the FAM labeled probe is multiplexed with a XP labeled probe (Example 13).
Figure 4:
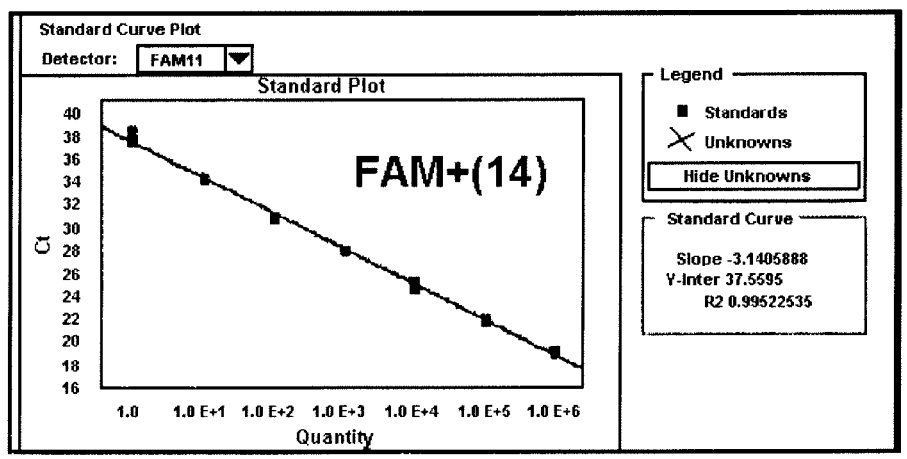

FIG. 4 illustrates the titration of a HSV 1,2 MGB Eclipse probe assay wherein the FAM-labeled probe is multiplexed with either an internal control (IC) probe labeled with PY. The titration real-time data for the multiplexed FAM and PY probes is shown in a). The titration is performed with cloned HSV 1,2 plasmid target with 10 fold concentrations from $10^0$ to $10^6$ copies. 1000 copies of IC were used in all HSV dilutions, while the IC primer concentrations were 0.3 µM in all HSV dilutions. The sequences for HSV 1,2 assay are MGB-Q-CCCAGGTTZ*TCCTCGCT-FAM (SEQ ID NO: 1) (probe), MGB-O-GCAAAGTCCCATCGTT-(14) (SEQ ID NO:2) (internal control probe), CCGTCCAGTCGTT-TATCTTC (SEQ ID NO:3) (limiting primer) and CGAACG-CAGCCCCGCTGGA (SEQ ID NO:4) (excess primer). MGB ligand is DPI$_3$; Q is the Eclipse Dark Quencher and Z is a universal base.

One of ordinary skill in the art will recognize from the provided description, figures, and examples, that modifications and changes can be made to the various embodiments of the invention without departing from the scope of the invention defined by the following claims and their equivalents. Additionally, all references, patents, patent publications and the like are expressly incorporated herein by reference.

What is claimed is:

1. A fluorescent dye reagent having the formula:

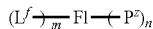

wherein

Fl is a fluorescent dye component;

$L^f$ is a linking group having an attached member selected from the group consisting of a protected or unprotected functional group, a reactive group, a polyfunctional linking moiety, a phosphoramidite moiety and a solid support;

the subscript m is an integer of from 0 to 1;

$P^z$ is a zwitterionic phosphonate group having the formula (a) or a protected phosphonate group having formula (b) or (c):

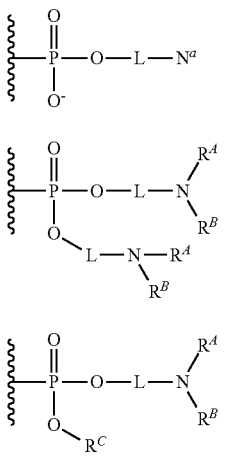

wherein the wavy line indicates the direct attachment to a $sp^2$ carbon of said fluorescent dye component; L is a linking group; $N^a$ is an ammonium ion group; each of $R^A$ and $R^B$ is independently selected from the group consisting of H, $(C_1-C_8)$alkyl, and a labile protecting group; $R^C$ is selected from the group consisting of H, $(C_1-C_8)$alkyl, aryl, aryl$(C_1-C_4)$alkyl, a labile protecting group or an alkylene linking group having a distal hydroxy or protected hydroxy group;

the subscript n is an integer of from 1 to 2:

and salts thereof.

2. A fluorescent dye reagent of claim 1, wherein said fluorescent dye component is selected from the group consisting of coumarin dyes, resorufin dyes, dipyrromethenboron difluoride dyes, ruthenium bipyridyl dyes, energy, transfer dyes, thiazole orange dyes, polymethines and N-aryl-1,8-naphthalimide dyes.

3. A fluorescent dye reagent of claim 1, having formula I:

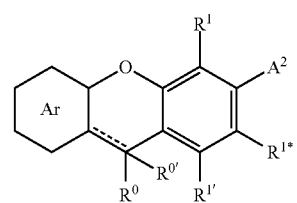

wherein,
the symbol ===, represents a single or double bond;
the Ar ring, represented by the symbol

is selected from the group consisting of:

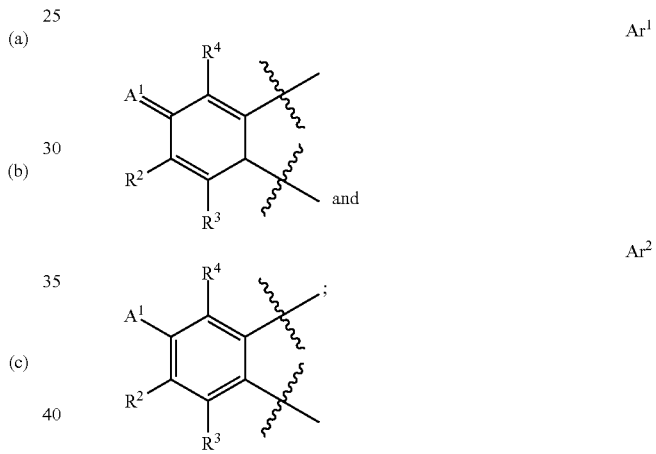

$A^1$ in $Ar^1$ represents O, N—Z, or $N^+(Z)_2$, and $A^1$ in $Ar^2$ represents OR, or $N(Z)_2$, wherein at each occurrence Z is independently hydrogen, $(C_1-C_8)$alkyl, aryl-$(C_1-C_8)$alkyl, aryl or a protecting group; wherein the aliphatic or aryl portions of the Z group are optionally substituted with halogen, $(C_1-C_4)$alkyl, aryl, $L^f$ or $P^z$; or optionally the Z group, at each occurrence, independently is combined with $R^2$ or $R^4$ to form a fused 5- to 7-membered ring, and the resultant fused 5- to 7-membered ring is optionally fused to an aryl ring, and is optionally substituted with halogen, $(C_1-C_4)$alkyl, $L^f$ or $P^z$; R, is selected from H, $(C_1-C_8)$alkyl, aryl, aryl$(C_1-C_4)$alkyl, protecting group and $L^f$;

$A^2$ represents OR or $N(Z)_2$, wherein each Z is independently hydrogen, $(C_1-C_8)$alkyl, aryl$(C_1-C_8)$alkyl, aryl or a protecting group; wherein the aliphatic or aryl portions of the Z group are optionally substituted with halogen, $(C_1-C_4)$alkyl, aryl, $L^f$ or $P^z$; or optionally the Z group, at each occurrence, independently is combined with $R^1$ or $R^{1''}$ to form a fused 5- to 7-membered ring wherein the resultant fused 5- to 7-membered ring is optionally fused to an aryl ring, and is optionally substituted with halogen, $C_1-C_4$ alkyl, aryl, $L^f$ or $P^z$; and the substituent R is selected from H, $(C_1-C_8)$alkyl, aryl, aryl$(C_1-C_4)$alkyl, a protecting group and $L^f$;

$R^{1'}$, $R^{1'''}$, $R^1$, $R^2$, $R^3$ and $R^4$ are each independently selected from the group consisting of H, halogen, cyano, $CF_3$, sulfo, ($C_1$-$C_8$)alkyl, ($C_1$-$C_8$)alkylthio, ($C_1$-$C_8$)alkoxy, aryl, heteroaryl, $L^f$ and $P^z$, wherein said aryl or heteroaryl group is optionally substituted with $P^z$; or optionally any two of the $R^{1'}$, $R^{1'''}$, $R^1$ and $R^3$ substituents that are attached to adjacent ring atoms are combined to form a five or six membered fused ring that is aromatic, non-aromatic or heteroaromatic, and is optionally substituted with $P^z$; and the alkyl portions of any of $R^{1'}$, $R^{1'''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; the aryl or heteroaryl portions of any $R^{1'}$, $R^{1'''}$ and $R^1$ through $R^4$ are optionally substituted with from one to four substituents selected from the group consisting of halogen, cyano, carboxy, sulfo, hydroxy, amino, mono- or di($C_1$-$C_6$)alkylamino, ($C_1$-$C_6$)alkyl, ($C_1$-$C_6$)alkylthio, ($C_1$-$C_6$)alkoxy, $L^f$ and $P^z$;

$R^0$ is halogen, cyano, $CF_3$, ($C_1$-$C_8$)alkyl, ($C_2$-$C_8$)alkenyl, ($C_2$-$C_8$)alkynyl, substituted or unsubstituted heteroaryl or aryl having the formula:

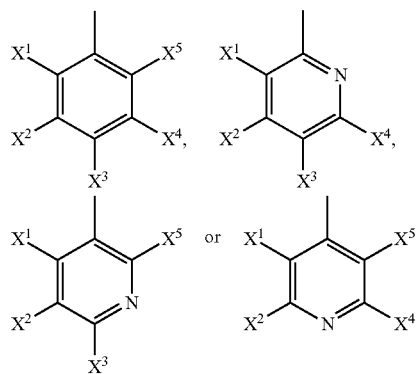

wherein $X^1$, $X^2$, $X^3$, $X^4$ and $X^5$ are each independently selected from the group consisting of H, halogen, cyano, $CF_3$, ($C_1$-$C_8$)alkyl, ($C_1$-$C_8$)alkoxy, ($C_1$-$C_8$)alkylthio, ($C_2$-$C_8$)alkenyl, ($C_2$-$C_8$)alkynyl, aryl, heteroaryl, $SO_3H$, $PO_3H_2$, $CO_2H$, $L^f$ and $P^z$ and optionally, any two adjacent substituents of $X_1$ to $X_5$ are combined to form an aromatic or heteroaromatic ring; wherein the aryl or heteroaryl portions of $R^0$ are optionally substituted with from one to four substituents selected from the group consisting of halogen, cyano, carboxy, sulfo, hydroxy, amino, mono- or di($C_1$-$C_6$)alkylamino, ($C_1$-$C_6$)alkyl, ($C_1$-$C_6$)alkylthio, ($C_1$-$C_6$)alkoxy, $L^f$ and $P^z$;

$R^{0'}$ in formula I is absent or is ($C_1$-$C_6$)alkoxy, hydroxy, ($C_1$-$C_6$)alkylamino, or, di($C_1$-$C_6$)alkylamino, or optionally, the $R^0$ and $R^{0'}$ groups are combined to form a 5- to 6-membered heterocyclic ring;

and wherein in formula I, there will be from 0 to 1 $L^f$ groups and from 1 to 4 $P^z$ groups, preferably 1 to 2 $P^z$ groups.

4. A fluorescent dye reagent of claim 3, having formula I(a) or I(b):

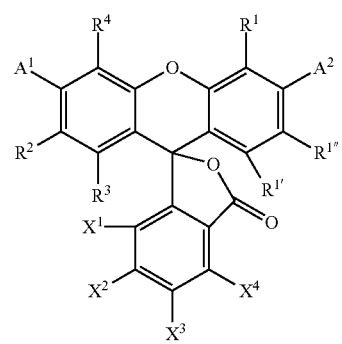

(Ia)

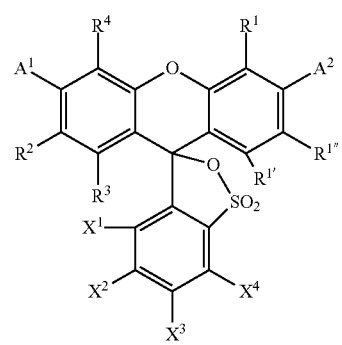

(Ib)

wherein each $A^1$ and $A^2$ are each independently OR or $N(Z)_2$, wherein R and Z are as set forth in claim 3;

$R^{1'}$, $R^{1'''}$, $R^1$, $R^2$, $R^3$ and $R^4$ are each independently selected from H, halogen, cyano, sulfo, aryl, heteroaryl, $CF_3$, ($C_1$-$C_8$)alkyl, ($C_1$-$C_8$)alkylthio, ($C_1$-$C_8$)alkoxy, $L^f$ and $P^z$, or optionally two adjacent members of $R^{1'}$, $R^{1'''}$, $R^2$ and $R^3$ are combined to form a five or six membered fused ring that is aromatic, non-aromatic or heteroaromatic and with is optionally substituted with $P^z$, wherein the alkyl portions of any of $R^{1'}$, $R^{1'''}$ and $R^1$ through $R^4$ are optionally substituted with halogen, carboxy, sulfa, amino, mono- or dialkylamino, alkoxy, cyano, haloacetyl or hydroxy, and the alkyl portions of the substituents have from 1 to 6 carbon atoms and the aryl or heteroaryl portions of any of $R^{1'}$, $R^{1'''}$ and $R^1$ through $R^4$ are optionally substituted with from one to four substituents selected from the group consisting of halogen, cyano, carboxy, sulfo, hydroxy, amino, mono- or di($C_1$-$C_6$)alkylamino, ($C_1$-$C_6$)alkyl, ($C_1$-$C_6$)alkylthio, ($C_1$-$C_6$)alkoxy, $L^f$ and $P^z$;

$X^1$, $X^2$, $X^3$ and $X^4$ are each independently selected from the group consisting of H, halogen, cyano, $CF_3$, ($C_1$-$C_8$)alkyl, ($C_1$-$C_8$)alkoxy, ($C_1$-$C_8$)alkylthio, ($C_1$-$C_8$)alkenyl, ($C_1$-$C_8$)alkynyl, $SO_3H$, $PO_3H$, $CO_2H$, $L^f$ and $P^z$ and optionally, any two adjacent $X^1$ through $X^4$ are combined to form an aromatic or heteroaromatic ring that is optionally further substituted with from one to four substituents selected from halogen cyano, carboxy, sulfo, hydroxy, amino, mono- or di($C_1$-$C_6$)alkylamino, ($C_1$-$C_6$)alkyl, ($C_1$-$C_6$)alkylthio, ($C_1$-$C_6$)alkoxy, $L^f$ and $P^z$.

5. A fluorescent dye reagent of claim 3, having formula Ic:

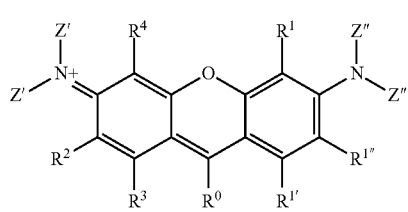

(Ic)

wherein the group Z' or Z", at each occurrence, is independently hydrogen, $(C_1-C_8)$alkyl, aryl-$C_1$-$C_8$ alkyl or aryl, wherein the aliphatic or aryl portions of the Z' or Z" groups are optionally substituted with halogen, $(C_1-C_4)$ alkyl, $L^f$ or $P^z$; optionally the Z' group, at each occurrence is independently combined with $R^2$ or $R^4$ to form a fused 5- or 6-membered ring, and optionally, the Z" group, at each occurrence is independently combined with $R^1$ or $R^{1''}$ to form a fused 5- or 6-membered ring; wherein if present, said fused 5- or 6-membered ring is optionally fuse to an aryl ring and is substituted with halogen, $C_1$-$C_4$ alkyl, $L^f$ or $P^z$; and the $R^{1'}$, $R^{1''}$, $R^1$, $R^2$, $R^3$, $R^4$ and $R^0$ groups in formula Ic are as described in claim 3.

6. A fluorescent dye reagent of claim 1, having formula:

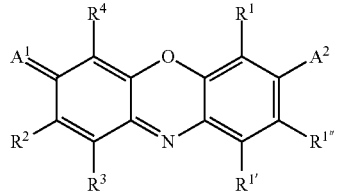

(IX)

wherein
$A^1$ represents O, N—Z or $N^+(Z)_2$ in which Z is independently H, $(C_1-C_8)$alkyl, $C_8$-alkyl, a protecting group or aryl, wherein the aliphatic or aryl portions of the Z group are optionally substituted with halogen, $(C_1-C_4)$alkyl, aryl, $L^f$ or $P^z$; wherein the Z group, at each occurrence, is optionally combined with $R^2$ or $R^4$ to form a 5- to 7-membered ring, wherein the resultant 5- to 7-membered ring is optionally fused to an aryl ring and is optionally substituted with halogen, $(C_1-C_4)$alkyl, aryl, $L^f$ or $P^z$;

A' represents OR or $N(Z)_2$ in which Z is independently H, $(C_1-C_8)$alkyl, aryl-$(C_1-C_8)$-alkyl, a protecting group or aryl, wherein the aliphatic or aryl portions of the Z group are optionally substituted with halogen, $(C_1-C_4)$alkyl, aryl $L^f$ or $P^z$; wherein the Z group, at each occurrence, is optionally combined with $R^1$ or $R^{1''}$ to form a 5- to 7-membered ring, wherein the resultant 5- to 7-membered ring is optionally fused to an aryl ring and is optionally substituted with halogen, $(C_1-C_4)$alkyl, aryl, $L^f$ or $P^z$; and R is selected from the group consisting of H, a protecting group, $(C_1-C_8)$alkyl, aryl, aryl$(C_1-C_4)$alkyl and $L^f$, or is optionally combined with $R^1$ or $R^{1''}$ to form a fused 5- to 7-membered ring;

$R^{1'}$, $R^{1''}$, $R^1$, $R^2$, $R^3$ and $R^4$ are each independently selected from H, halogen, cyano, $CF_3$, sulfo, $(C_1-C_8)$alkyl, $(C_1-C_8)$alkylthio, $(C_1-C_8)$alkoxy, aryl, heteroaryl, $L^f$ and $P^z$;

wherein the alkyl portions of any of $R^{1'}$, $R^{1''}$ and $R^1$ through $R^4$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$, $R^{1''}$ and $R^1$ through $R^4$ are optionally substituted with from one to four substituents selected from the group consisting of halogen, cyano, carboxy, sulfo, hydroxy, amino, mono- or di($C_1$-$C_6$)alkylamino, $(C_1-C_6)$alkyl, $(C_1-C_6)$alkylthio, $(C_1-C_6)$alkoxy, $L^f$ and $P^z$.

7. A fluorescent the reagent of claim 1, having formula:

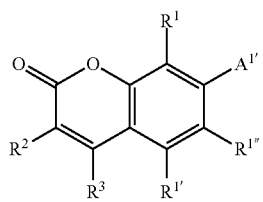

(V)

wherein
$R^1$, $R^{1'}$, $R^{1''}$, $R^2$ and $R^3$ are each independently selected from the group consisting of H, halogen, cyano, sulfo, $CF_3$, $(C_1-C_8)$alkyl, $(C_1-C_8)$alkylthio, $(C_1-C_8)$alkoxy, aryl, heteroaryl, $L^f$ and $P^z$;

wherein the alkyl portions of any of $R^{1'}$, $R^{1''}$ and $R^1$ through $R^3$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$, $R^{1''}$ and $R^1$ through $R^4$ are optionally substituted with from one to four substituents selected from the group consisting of halogen, cyano, carboxy, sulfo, hydroxy, amino, mono- or di($C_1$-$C_6$)alkylamino, $(C_1-C_6)$alkyl, $(C_1-C_6)$alkylthio, $(C_1-C_6)$alkoxy, $L^f$ and $P^z$; and $A^1$ represents OR, $N(Z)_2$, in which Z is independently hydrogen, $(C_1-C_8)$alkyl, aryl-$(C_1-C_8)$alkyl, aryl or a protecting group; wherein the aliphatic or aryl portions of the Z group are optionally substituted with halogen, $(C_1-C_4)$alkyl, $L^f$ or $P^z$; or optionally the Z group at teach occurrence is independently combined with $R^1$ or $R^{1''}$ to form a 5- to 7-membered ring, wherein the resultant 5- to 7-membered ring is optionally substituted with halogen, $(C_1-C_4)$alkyl, $L^f$ or $P^z$, and is optionally fused with an aryl or heteroaryl ring wherein the aryl or heteroaryl ring is optionally substituted with halogen, $(C_1-C_4)$alkyl, $L^f$ or $P^z$; and the R substituent in $A^1$ is hydrogen, $(C_1-C_8)$ alkyl, aryl, aryl$(C_1-C_4)$alkyl, a protecting group or $L^f$.

8. A fluorescent dye reagent of claim 1, having the formula:

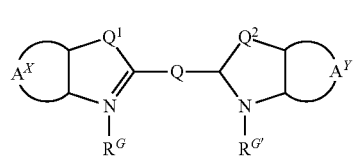

(VII)

wherein
$Q^1$ and $Q^2$ are independently selected from O, S, N and $CR^aR^b$ or —C(=$CH_2$)— wherein $R^a$ and $R^b$ are independently selected from the group consisting of H, methyl, ethyl and $L^f$;

the rings, $A^x$ and $A^y$, each independently represents a condensed substituted or unsubstituted aryl or heteroaryl rings wherein said rings are optionally substituted with halogen, CN, CF, $(C_1-C_8)$alkyl, $(C_1-C_8)$alkoxy, $(C_1-C_8)$alkylthio, $(C_1-C_8)$alkylamino, di$(C_1-C_8)$alkylamino, an aryl or heteroaryl that is optionally substituted with $L^f$ or $P^z$;

Q represents a conjugated linking system;

$R^G$ and $R^{G'}$ are independently selected from the group consisting of H, $C_1-C_8$ alkyl, heteroalkyl, alkylene sulfonic acid, alkylene phosphoric acid, alkylene phosphonic acid, alkylene aryl, substituted alkylene aryl, alkylene carboxylic acid, $L^f$ and $P^z$, wherein said aryl group in $R^G$ or $R^{G'}$ is optionally substituted with from about one to two $P^z$ groups and from about 0 to about 2 $L^f$ groups.

9. A fluorescent dye reagent of claim 1, having the formula:

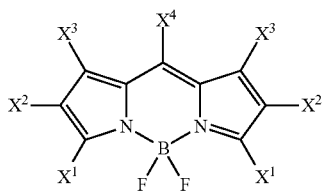
(VIII)

wherein $X^1$, $X^2$, $X^3$ and $X^4$ are each independently selected from the group consisting of H, halogen, cyano, $CF_1$, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$, $PO_3H$, $CO_2H$, $L^f$ and $P^z$; and optionally, any two adjacent $X^1$ through $X^4$ are combined to form a non-aromatic, aromatic or heteroaromatic five or six-membered ring that is optionally further substituted with from one to four substituents selected from halogen, cyano, carboxy, sulfo, hydroxy, amino, mono- or di$(C_1-C_6)$alkylamino, $(C_1-C_6)$alkyl, $(C_1-C_6)$alkylthio, $(C_1-C_6)$alkoxy, $L^f$ and $P^z$; and wherein there is present from 0 to 1 $L^f$ groups and from 1 to 2 $P^z$ groups.

10. A fluorescent dye reagent having the formula:

Fl-$P^1$ wherein

Fl is a fluorescent dye component; and $P^1$ is functionalized phosphonate group having the formula:

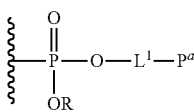

wherein the wavy line indicates the direct attachment to a sp$^2$ carbon said fluorescent dye component;

$L^1$ is a linking group;

R is a member selected from the group consisting of H, $C_1-C_8$ alkyl, aryl, aryl$C_1-C_4$ alkyl, -$L^a$-$N^a$, and -$L^a$-$NR^AR^B$;

wherein $L^a$ is an alkylene linking group; $N^a$ is an ammonium ion group; and each of $R^A$ and $R^B$ is independently selected from the group consisting of H, $(C_1-C_8)$alkyl, and a labile protecting group; and $P^a$ is a functional group component selected from the group consisting of a phosphoramidite moiety, a mono-, di- or tri-functional linking group having at least one terminal functional group or protected functional group, a solid support and a reactive group;

and salts thereof.

11. A fluorescent dye reagent of claim 10, wherein said fluorescent dye component is selected from the group consisting of coumarin dyes, resorufin dyes, dipyrromethenboron difluoride dyes, ruthenium bipyridyl dyes, energy transfer dyes, thiazole orange dyes, polymethines and N-aryl-1,8-naphthalimide dyes.

12. A conjugated substance comprising one or more phosphonylated fluorescent dyes coupled through a linking group to a conjugated substance or biological agent, wherein the phosphonylated fluorescent dyes have structures selected from the group of consisting of:

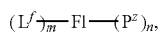

wherein

Fl is a fluorescent dye component;

$L^f$ is a linking group connecting said conjugated substance and said phosphonylated fluorescent dye;

the subscript m is an integer of from 0 to 1;

$P^z$ is a zwitterionic phosphonate group having the formula (a) or a protected phosphonate group having formula (b) or (c):

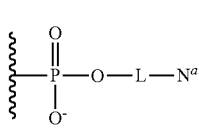
(a)

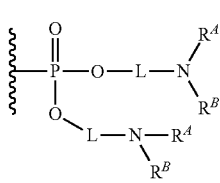
(b)

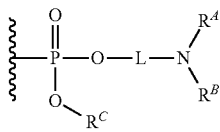
(c)

wherein the wavy line indicates the direct attachment to a sp$^2$ carbon of said fluorescent dye component; L is a linking group; $N^a$ is an ammonium ion group; each of $R^A$ and $R^B$ is independently selected from the group consisting of H, $(C_1-C_8)$alkyl, and a labile protecting group; $R^C$ is selected from the group consisting of H, $(C_1-C_8)$alkyl, aryl, aryl$(C_1-C_4)$alkyl, a labile protecting group or an alkylene linking group having a distal hydroxy or protected hydroxy group;

the subscript n is an integer of from 0 to 4; or

wherein

Fl is a fluorescent dye component; and $P^1$ is functionalized phosphonate group having the formula:

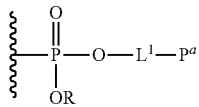

wherein the wavy line indicates the direct attachment to a $sp^2$ carbon of said fluorescent dye component;
$L^1$ is a linking group;
R is a member selected from the group consisting of H, $C_1$-$C_8$ alkyl, aryl, aryl$C_1$-$C_4$ alkyl, -$L^a$-$N^a$, and -$L^a$-$NR^AR^B$;
  wherein $L^a$ is an alkylene linking group; $N^a$ is an ammonium ion group; and each of $R^A$ and $R^B$ is independently selected from the group consisting of H, ($C_1$-$C_8$)alkyl, and a labile protecting group; and
$P^a$ is a conjugated substance;
and salts thereof.

* * * * *

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:HSV 1,2
      assay FAM-labeled probe
<220> FEATURE:
<221> NAME/KEY: modified_base
<222> LOCATION: (1)
<223> OTHER INFORMATION: n = c conjugated to Eclipse Dark Quencher (Q)
      and minor groove binder (MGB) DPI-3
<220> FEATURE:
<221> NAME/KEY: modified_base
<222> LOCATION: (9)
<223> OTHER INFORMATION: n = universal base (Z)
<220> FEATURE:
<221> NAME/KEY: modified_base
<222> LOCATION: (17)
<223> OTHER INFORMATION: n = t conjugated to FAM

<400> SEQUENCE: 1
nccaggttnt cctcgcn                                                   17

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:HSV 1,2
      assay phosphonate dye-labeled internal control probe
<220> FEATURE:
<221> NAME/KEY: modified_base
<222> LOCATION: (1)
<223> OTHER INFORMATION: n = g conjugated to Eclipse Dark Quencher (Q)
      and minor groove binder (MGB) DPI-3
<220> FEATURE:
<221> NAME/KEY: modified_base
<222> LOCATION: (16)
<223> OTHER INFORMATION: n = t conjugated to phosphonate dye compound
      (14)

<400> SEQUENCE: 2
ncaaagtccc atcgtn                                                    16

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:HSV 1,2
      limiting primer

<400> SEQUENCE: 3
ccgtccagtc gtttatcttc                                                20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:HSV 1,2
      excess primer

<400> SEQUENCE: 4
cgaacgcagc cccgctgga                                                 19
```